United States Patent
Porschewski

(10) Patent No.: US 10,407,713 B2
(45) Date of Patent: Sep. 10, 2019

(54) REAGENT USABLE FOR THE ISOLATION AND/OR PURIFICATION OF NUCLEIC ACIDS

(75) Inventor: Peter Porschewski, Langenfeld (DE)

(73) Assignee: QIAGEN GmbH, Hilden (DE)

( * ) Notice: Subject to any disclaimer, the term of this patent is extended or adjusted under 35 U.S.C. 154(b) by 809 days.

(21) Appl. No.: 14/130,436

(22) PCT Filed: Jul. 4, 2012

(86) PCT No.: PCT/EP2012/062953
§ 371 (c)(1),
(2), (4) Date: Dec. 31, 2013

(87) PCT Pub. No.: WO2013/004710
PCT Pub. Date: Jan. 10, 2013

(65) Prior Publication Data
US 2014/0154693 A1    Jun. 5, 2014

Related U.S. Application Data

(60) Provisional application No. 61/597,469, filed on Feb. 10, 2012.

(30) Foreign Application Priority Data

Jul. 4, 2011    (EP) .................................... 11172557

(51) Int. Cl.
*C12Q 1/6806* (2018.01)
*C12N 15/10* (2006.01)

(52) U.S. Cl.
CPC ....... *C12Q 1/6806* (2013.01); *C12N 15/1003* (2013.01)

(58) Field of Classification Search
CPC .......................... C12Q 1/6806; C12N 15/1003
(Continued)

(56) References Cited

U.S. PATENT DOCUMENTS 5,234,809 A    8/1993    Boom et al.
6,355,792 B1 *  3/2002    Michelsen ......... C12N 15/1006
                                                536/25.4
(Continued)

FOREIGN PATENT DOCUMENTS

DE    10 2008 026058 A1    12/2009
EP       1 074 616 B1     2/2008
(Continued)

OTHER PUBLICATIONS

Kreader Applied and Environmental Microbiology, Mar. 1996, p. 1102-1106.*
(Continued)

*Primary Examiner* — Jezia Riley
(74) *Attorney, Agent, or Firm* — Seed IP Law Group LLP

(57) ABSTRACT

The present invention provides a special reagent for the pretreatment of sample materials. The pretreatment with the reagent according to the invention enables the isolation of nucleic acids by a uniform method from very diverse sample materials, in particular different bioprocess samples, even if the nucleic acids are only present in small amounts in the sample materials. The reagent used for the pretreatment comprises, as key component, at least one compound comprising an amino group. The invention further relates to methods of purification of nucleic acids, in which the sample material is pretreated correspondingly, and suitable kits.

70 Claims, 9 Drawing Sheets

(58) Field of Classification Search
USPC .................................... 536/25.4; 435/6.12
See application file for complete search history.

(56) References Cited

U.S. PATENT DOCUMENTS

| | | |
|---|---|---|
| 6,677,440 B1 | 1/2004 | Roemisch et al. |
| 2001/0018513 A1 | 8/2001 | Baker |
| 2002/0010145 A1 | 1/2002 | Willson, III et al. |
| 2002/0197637 A1 | 12/2002 | Willson, III et al. |
| 2003/0229222 A1 | 12/2003 | Kojima |
| 2009/0325175 A1 | 12/2009 | Anderson et al. |

FOREIGN PATENT DOCUMENTS

| | | |
|---|---|---|
| WO | 93/11221 A1 | 6/1993 |
| WO | 95/01359 A1 | 1/1995 |
| WO | WO 99/29703 * | 6/1999 |
| WO | 03/102184 A1 | 12/2003 |
| WO | 2004/013155 A2 | 2/2004 |
| WO | 2006/084753 A1 | 8/2006 |
| WO | 2006/103094 A2 | 10/2006 |
| WO | 2008/039668 A1 | 4/2008 |
| WO | 2009/144182 A1 | 12/2009 |
| WO | 2011/151428 A1 | 12/2011 |

OTHER PUBLICATIONS

Wang et al., "Residual DNA Analysis in Biologics Development: Review of Measurement and Quantitation Technologies and Future Directions," *Biotechnology and Bioengineering* 109(2):307-317, 2012.

Wolter et al., "Assays for Controlling Host-Cell Impurities in Biopharmaceuticals," *BioProcess International* 3(2):40-46, 2005. (5 pages).

* cited by examiner

REAGENT USABLE FOR THE ISOLATION AND/OR PURIFICATION OF NUCLEIC ACIDS

The present invention relates to a reagent, as well as several methods and a kit suitable for the isolation and/or purification of nucleic acids, in particular from a sample material comprising a low concentration of the target nucleic acids to be isolated.

BACKGROUND OF THE INVENTION

A great number of methods are known in the prior art for isolating nucleic acids, such as DNA and RNA, which allow an isolation from sample materials of quite various origin. These include sample materials of natural origin, for example complex samples that can be obtained from humans, animals, plants and the environment, and sample materials from a laboratory culture, such as microorganisms and cell culture materials.

The fundamental principle of nucleic acid isolation is generally independent of the type of sample material and can be divided into a few steps: an optional digestion of the sample material, for example in form of a lysis, the actual nucleic acid isolation and optionally the purification of the isolated nucleic acids. The isolation of the target nucleic acids from the contaminating sample constituents such as for example cell fragments and molecules different from nucleic acids, as well as the purification of the nucleic acids can be divided into two types of methods, which differ mainly in the number of separation steps and the separating agent:

In a classical method, often a chaotropic agent-containing aqueous buffer is first added to the sample material for lysis of the cells respectively digestion of the sample, said buffer usually containing a guanidinium salt. This is often followed by the denaturation of contaminating proteins and extraction of the nucleic acids by mixing with an organic extractant, which usually contains phenol and/or chloroform. After separating the nucleic acid-containing aqueous phase from the organic phase, for example an alcohol precipitation is carried out to purify the nucleic acids from water-soluble contaminants and phenol/chloroform components.

This extraction method has the disadvantage that a small portion of the organic extractant may always remain in the aqueous phase, so that several time-consuming steps of purification of the nucleic acid phase are required, which have an adverse influence on the yield of the target nucleic acids. Even after several purification steps, the purified nucleic acid samples often do not have the necessary purity for subsequent applications, in particular with regard to residuals of the extractant phenol.

An alternative multi-step method avoids the use of toxic organic solvents by using a solid mineral carrier material, which is based for example on a silicon dioxide compound. Owing to the generally mainly selective binding of the nucleic acids to the carrier material, the nucleic acids are isolated in the form of nucleic acid-carrier material complexes. The initial step in this method is usually also cell lysis, unless the nucleic acids to be isolated are already present in free form. For degrading cell constituents and/or other sample constituents, for example proteins, usually a chaotropic agent-containing aqueous buffer and usually a protein-degrading enzyme are added to the sample material. The nucleic acids released from the used sample material are then contacted with the carrier material under suitable binding conditions, usually in the presence of alcohol. The first required isolation step is usually based on selective adsorption of the nucleic acids to the carrier material, usually followed by a separation of the resulting nucleic acid-carrier material complexes from the surrounding liquid. This can either take place almost simultaneously in a filtration process, if the carrier material functions for example as filter matrix, or in a subsequent step for separating the complexes from the suspension. Optionally this is followed by a purification of the bound nucleic acids in one or more washing steps. Usually an elution follows as a final step of the isolation process, in which the bound nucleic acids are released from the carrier material with an aqueous reagent. This step is optional, since in some subsequent applications, for example the polymerase chain reaction, the binding of the carrier materials to the target nucleic acids is not disturbing. This multi step isolation method has become established owing to its advantages, such as improved yield and purity of the nucleic acids, compared to other classical methods.

A number of similar isolation methods that are based on the multi-step method described above are described in the prior art (see for example U.S. Pat. No. 5,234,809, WO 93/11221, WO 95/01359 and WO 2006/084753), which are characterized for example by the use of different carrier materials, different mechanisms for separating the nucleic acid-carrier material complexes from the sample and/or different reagent compositions.

Furthermore, WO 2009/144182 (Fabis et al.) discloses a universal composition for a lysis, binding and washing reagent for the isolation and purification of nucleic acids, which comprises at least one chaotropic compound, at least one buffer compound and at least one non-ionic surfactant. This reagent has various advantages, as it is more stable in storage than the Tween-containing formulations known in the prior art, used for example for cell lysis, as it increases the nucleic acid yield and/or produces nucleic acid eluates without turbidity.

All manual or automated methods known in the prior art, including the aforementioned examples, show a continuous further development of the isolation and purification of nucleic acids from various sample materials, among other things for increasing yield, purity, speed and/or sample throughput. The sample materials used in the prior art generally have in common that they contain the nucleic acids to be isolated in quite large amounts and/or they are similar with respect to their nature and/or composition, that the type of sample material has little if any influence on the efficiency of nucleic acid purification. Furthermore, the methods known in the prior art are as a rule also optimized in relation to one sample material or to similar sample materials (for example blood and blood products). However, the methods known in the prior art are as a rule not designed for and/or are not capable of also quantitatively purifying small amounts of nucleic acids from very different sample materials, which for example differ considerably with respect to their pH, their composition, their protein content and in particular their salt content, in high purity and for a high sample throughput. In particular the known methods are not intended for purifying nucleic acids quantitatively from bioprocess samples, such as for example aqueous buffer solutions with different compositions. Such a method would be of interest for example in the area of the production of biotechnological products, in particular for biopharmaceuticals.

Biopharmaceuticals include in particular proteins and peptides (for example antibodies, antigens, growth hormones), nucleic acids (for example DNA, RNA, plasmids, siRNA), viruses and/or vaccines. Biopharmaceuticals are produced using the means of modern biotechnology, in particular with the aid of natural or genetically modified organisms. Production usually employs eukaryotic or prokaryotic host cells, which are often modified by genetic engineering so that they are able to produce the desired biopharmaceutical. Respective genetic engineering techniques are well known in the prior art and include but are not limited to recombinantly introducing a gene encoding the product of interest such as e.g. a protein into a cell. For this purpose, a vector may be used. The respectively modified cell is then capable of producing the product of interest. In particular, for this it is possible to use cell lines from mammals and insects, recombinant microorganisms in bacterial or yeast cultures, viruses, as well as plant meristems and genetically modified plants. Biopharmaceuticals are applied inter alia for the prevention, diagnosis and treatment of diseases. Furthermore, biotechnological products, including biopharmaceuticals can also be produced by biotransformation. For this purpose, genetically modified or unmodified cells, such as in particular bacteria or yeast cells, are contacted with a chemical precursor and the cells transform said precursor to a desired product using their enzymatic machinery.

In the prevention of diseases, various immunization techniques for the prevention of bacterial and viral diseases have become established, and thereby biotechnologically produced vaccines are becoming increasingly important. These include viruses, antigenic components of viral envelopes in conjugated or unconjugated form, or pure DNA components of viruses, bacteria or other organisms. Parts of a viral envelope or recombinant viruses can also be used for preventive vaccination against diseases that are caused by a viral infection. For example, this technique are applied for HPV (human papillomavirus) vaccination for preventing cervical cancer. Mainly monoclonal antibodies are applied for molecular diagnostics, and are used for example for immunophenotyping, immunohistological determinations or ELISA. Treatment of diseases is another constantly growing field of application for biopharmaceuticals. Treatments are carried out using recombinant proteins, hormones, recombinant organisms, viruses, recombinant immune cells or also using genes.

Biotechnological products, such as biopharmaceuticals in particular, usually go through a multistage purification process. To obtain the biotechnological product, the producing host may for example be lysed, or the biotechnological product can be isolated from the culture supernatant. Purification of the biotechnological product from the culture supernatant and/or the lysate is generally carried out using chromatographic methods. The purpose of this purification is usually to remove contaminants, for example cell fragments, cellular molecules, culture medium and salts from the resultant biotechnological product and to enrich it. Moreover, especially in the case of biopharmaceuticals, it is of particular interest to achieve a considerable reduction in the content of nucleic acid contaminants (in particular host cell nucleic acids), as these contaminants may, for example depending on the concentration and the host, impart a potential oncogenic risk to the final biopharmaceutical.

Usually, for purification of biotechnological products, such as biopharmaceuticals in particular, purification steps are applied by means of standard chromatographic techniques, for example ion exchange chromatography, protein A/G affinity chromatography, hydrophobic interaction chromatography and/or hydrophilic interaction chromatography, which are generally selected specifically for the biopharmaceutical agent to be purified in each case. The eluates from these purification methods, which are here preferably encompassed by the term bioprocess samples, are as a rule aqueous purification fractions, corresponding to these purification methods. Depending on the selected chromatographic technique, they are usually characterized by a wide range of different compositions of ingredients, for example with respect to the purification buffer used (for example acetate, phosphate, citrate or maleate buffer), to the salt concentrations, pH values, the phosphate components and/or the protein content. Bioprocess samples of successive purification steps usually display an increasing degree of purity of the biotechnological product, for example of the biopharmaceutical, which as the end product of the purification process must fulfil the purity criteria of regulatory authorities, so that it can be authorized for example as a medicinal product or diagnostic product.

A number of quality guidelines for medicinal product testing and authorization for the use on human beings are issued by national and international authorities. These include the ICH guidelines (EU, USA, Japan), the EMEA guidelines (EU) and the FDA guidelines (USA) and WHO guidelines. These guidelines define, for medicinal products, among other things the maximum permissible residual amounts of various molecules that originate from host organisms, including the amount of endotoxins, the amount of proteins and the permissible amount of prokaryotic or eukaryotic DNA. With respect to the DNA of the host organisms, according to the WHO decision of 1987, an amount of 100 pg per dose of medicinal product to be administered must not be exceeded. Ideally, and advised by the FDA, a much lower residual amount of host DNA of only 10 pg at most per dose to be administered is to be achieved, to ensure greater safety for the patient.

Similar rules also apply to other biotechnology products, for which nucleic acid contaminations, for example with viral nucleic acids, can represent a problem.

A trend that is seen in the determination of these nucleic acid contaminants is the use of very sensitive molecular detection techniques, for example the quantitative polymerase chain reaction (qPCR). Corresponding methods are known in the prior art and form the subject matter of various patent applications (see for example US2009/325175). However, to perform said detection it is first necessary to isolate effectively the small amounts of contaminating nucleic acids (for example from the host) from the bioprocess samples. This use is not only of interest for nucleic acid analysis in the finally purified end product, it is in particular also of great importance for the purification fractions arising continuously one after another in the purification process, as analysis of these purification fractions enables monitoring and assessing the successful outcome of purification. In this way, it is also possible to detect faults in the purification process more quickly. Therefore it is common in the prior art, at various points of the purification process and preferably at each stage of the purification process, to determine the amount of target nucleic acid (for example of a contamination, in particular with host DNA) in the respective purification fraction. This use imposes particular challenges on the nucleic acid purification method to be used, because—as explained—the various purification fractions, as a rule differ considerably from each other with respect to their chemical composition and their pH. Here, owing to the high sample throughput, it is desirable, despite the very different sample materials, to be able to use a uniform method of nucleic acid purification, that can ideally be automated, and by which even very small amounts of nucleic acids can be isolated as quantitatively and consistently as possible. Methods for isolation of nucleic acids being commercially available for this purpose so far do not fulfil these requirements satisfactorily, as they have various disadvantages.

The DNA Extractor Kit from the company WAKO (#295-50201) is a manual method, in which contaminating proteins are denatured by the use of a chaotropic salt (NaI) and an anionic detergent (sodium N-lauryl-sarcosine). After adding alcohol and glycogen, the nucleic acids in the sample are precipitated, wherein the precipitate can also contain entrained contaminants, which can be disturbing in a subsequent PCR reaction. Furthermore, the method is time-consuming and cannot easily be automated.

The PrepSEQ Residual DNA Sample Preparation Kit from the company ABI is a method that uses magnetic silica particles and is suitable for automation. A disadvantage of this method is that the sample material first requires laborious preparation, in that the samples must be treated individually in the sequence 1.) adjustment to an optimum pH and 2.) adjustment of NaCl concentration in the sample to >0.5 M. This preparation is necessary because of the varying nature/composition of the bioprocess samples, as otherwise the subsequent isolation operation, in particular with small amounts of nucleic acids in the sample material, would not function efficiently. This preparation is time-consuming, because often it can only be done manually, so that this method does not permit high sample throughput. Automation of subsequent steps of nucleic acid isolation would not be useful in this case, as the step of individual sample preparation would still be included.

Other methods, which are based on the automated use of magnetic particles, are for example the methods of isolating nucleic acids with the laboratory automate QIAsymphony using the correspondingQIAsymphony Kits from the company QIAGEN GmBH. These applications enable isolating and purify nucleic acids quantitatively from a number of different sample types such as tissue, whole blood, plasma, serum, urine, forensic sample materials etc., but they are not originally designed to fulfil the special requirements on sample materials such as bioprocess samples and in particular purification fractions. The special nature of these samples arises, as explained, from the use of a large number of specific chromatographic techniques, which often result in aqueous bioprocess samples with very different chemical composition and different pH values, which contain inter alia inhibitors for known methods of nucleic acid isolation and purification. Furthermore, generally they only contain small amounts of the target nucleic acid (for example host DNA).

The disadvantages of the commercially available methods of nucleic acid isolation, including the methods given above as examples, emphasize the existing demand in the pharmaceutical and biotechnology industry for a suitable method for isolating nucleic acids, which allows even small amounts of nucleic acids, such as for example contaminating nucleic acids (which originate for example from host organisms or host cells) to be purified, wherein the method should preferably represent a quantitative, consistent solution that can be automated.

Besides the pharmaceutical and biotechnology industry, there are yet other fields of application in which detection of nucleic acids that are present at very low concentrations, in various sample materials, is of considerable interest. These include molecular medical diagnostics, in which it is for example of interest to detect, from body materials, foreign nucleic acids, such as fetal, viral, and microbial nucleic acids, which are present in small amounts. Obtaining freely circulating fetal nucleic acid from maternal blood samples is often crucially important in prenatal diagnostics, as it represents a genetic method for analysing the fetus, which does not require amniocentesis and therefore holds no risk for the unborn offspring. In the diagnosis of infections, the isolation of microbial nucleic acids that are present in small amounts provides early evidence about an infection and permits early treatment of the patient. Furthermore, if there is a risk of infection, rules of conduct can be apprehended early, for example temporary quarantine of the patient, in order to limit or even prevent spread of the infection. Very early pathogen detection is of great importance especially in the case of aggressive, highly infectious pathogens, which even in very small numbers cause an infection with a serious and barely treatable course of disease. This applies, for example, to Shiga toxin producing *Escherichia coli* (STEC) bacteria, infection with which leads not infrequently to the death of the patient, as a classical antibiotic therapy cannot be used. Early recognition of the infection, as well as treatment and early isolation of the patient, can save lives. Endogenous nucleic acids that occur in small amounts are also of interest in molecular diagnostics. These include for example small non-coding RNAs such as in particular microRNA (miRNA) molecules, which regulate gene expression at the posttranscriptional level. They are used for example as marker molecules in the area of oncological diagnostics.

Forensics is another field of application in which nucleic acid diagnostics plays an important role, because often only that way the decisive evidence for clarifying forensic questions can be provided. Forensic sample materials are generally characterized by an especially wide variety, which in principle encompasses all materials and fluids that can carry or contain human nucleic acids. In particular, however, they are sample materials that often only contain very small traces of the nucleic acids to be detected. A molecular detection system therefore requires a very efficient and effective method of isolating nucleic acids, in which there are only minimal or ideally no losses of the nucleic acids that are only present in small amounts, in order to enable subsequent detection at all.

Molecular nucleic acid detections are also very important in food and environmental diagnostics, for example for detecting contaminations by bacteria, viruses, fungi and/or protozoa in the area of food production, foodstuff inspection, breeding and monitoring of plant developments and/or also in the analysis of water, soil and air quality. Also in this case the sample materials can have a very diverging composition and may only contain very small amounts of the nucleic acids of interest. Molecular detection based on microbial nucleic acids, instead of a method of detection by means of cultures of microorganisms, is a method that is conceivably more time-saving and more specific.

In basic research, synthetically produced nucleic acids, for example small interfering RNA (siRNA), are used in genome analysis. The chemical production of nucleic acids requires purification processes that are generally carried out by means of chromatographic techniques. Also in this case, a molecular method of nucleic acid isolation and/or purification would be of interest, which permits a quantitative isolation of the nucleic acids and allows to obtain the product in a low-salt solution. Consequently here as well, the composition of the purification fractions must not have any disturbing effect on the method of nucleic acid isolation and/or purification.

The present invention is therefore based among other things on the problem of providing a method of isolation and/or purification of nucleic acids that are present in small amounts in sample materials of varying composition, which in particular permits the quantitative detection of the isolated nucleic acids. Moreover, in particular a problem to be solved by the present invention is to provide a respective method, which enables the preferably quantitative isolation of nucleic acids from various bioprocess samples, in particular from various purification fractions obtained in a chromatographic purification process, even if these only contain a small amount of the nucleic acids to be isolated.

SUMMARY OF THE INVENTION

The present invention is based on the surprising finding that an unexpectedly simple pretreatment of the sample material with a special reagent enables isolating nucleic acids by means of a uniform method from very diverse sample materials, even if the nucleic acids are only present in the sample material in very small amounts. Advantageously, the pretreatment according to the invention therefore enables to omit individual adaptations or adjustments of the sample material (for example of pH or salt concentration) or the subsequent method of purification, even if very diverse sample materials are being processed. According to the invention, the sample material is pretreated with a special reagent; afterwards the actual isolation of the contained nucleic acids can occur. For this purpose, owing to the pretreatment according to the invention, even conventional standard methods can be used. If the sample material is pretreated according to the invention with the special reagent, differences between different sample materials can surprisingly be compensated respectively overcome, and it thus becomes possible to isolate the nucleic acids contained in the sample material by means of a uniform isolation method. Without the pretreatment according to the invention this would not be possible, would not be sufficiently efficient or would be less efficient. Thus, the present invention offers not only an effective, but also a surprisingly simple solution of the underlying problem. The solution according to the invention also offers the advantage of being automatable, because among other things individual adaptation or adjustment steps of the sample materials and/or of the subsequent isolation method can be omitted.

Owing to these important advantages, the present invention is suitable in particular for the isolation of nucleic acids from bioprocess samples, such as in particular from a purification fraction obtained in a purification process for biopharmaceuticals. As a rule these special sample materials often differ considerably in their composition (for example in the comprised buffer and the protein and/or salt content) and their pH, what significantly impedes nucleic acid isolation by means of a uniform method. Sometimes nucleic acid isolation from bioprocess samples is even impossible without special measures. Surprisingly, existing differences between individual bioprocess samples can, however, be effectively compensated by the pretreatment according to the invention. Even if the composition of the bioprocess samples differs, a uniform nucleic acid isolation method can be used and even small amounts of contained nucleic acids can be purified with the method according to the invention efficiently, effectively and reliably. The low limits of detection that are achieved with the method according to the invention are particularly important for bioprocess samples, because with these sample materials the nucleic acids that are to be purified often represent contaminants (for example host DNA or viral nucleic acids), which correspondingly are only present in small amounts in the sample material. The advantages of the invention in this field of use, which is especially demanding because of the usually very diverse nature of the sample material, are also clearly demonstrated by the examples. They demonstrate that sometimes it is only the pretreatment according to the invention which enables nucleic acid isolation at all, and furthermore provides an efficient, effective and reliable isolation of even minimal amounts of nucleic acids from various bioprocess samples. Moreover, the method according to the invention provides a quantitative isolation and in addition is it automatable, which are also valuable advantages in this special field of application.

However, besides as the application in the area of bioprocess samples and biopharmaceutics in particular, the present invention offers decisive advantages in the purification of nucleic acids from other sample materials, which for example contain only small amounts of nucleic acids and/or are of very diversed nature. Corresponding fields of application are also explained below.

Therefore, among other things, the present invention provides various methods for isolation and/or purification of nucleic acids from various sample materials, a special reagent for the pretreatment of the sample materials and a suitable kit for carrying out the method according to the invention. Details of these various aspects of the present invention are explained subsequently.

DETAILED DESCRIPTION OF THE INVENTION

Figure 1:
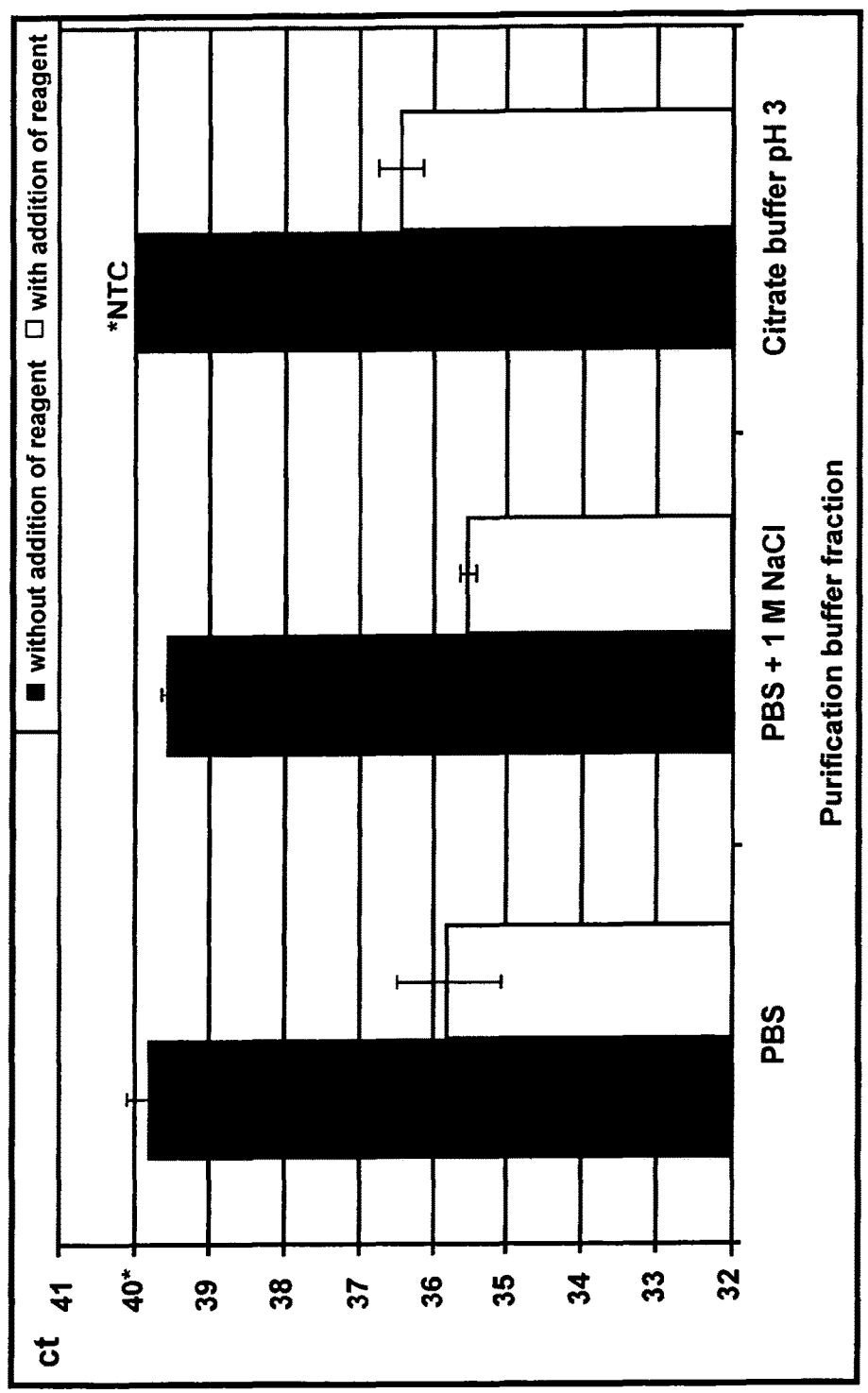
FIG. 1 is a graph showing Ct values of quantitative real-time PCR performed with DNA isolated using different purification buffers with or without addition of an exemplary reagent according to Example 1.

According to a first aspect of the present invention, a method is provided for the isolation and/or purification of nucleic acids from a sample material, which comprises the following steps:
a. Adding a reagent to the sample material, wherein the reagent comprises at least one or more compounds comprising an amino group, selected from one or more of the following groups:
  i. polar-neutral proteinogenic α-aminocarboxylic acids, preferably asparagine, cysteine, glutamine, glycine, threonine and serine, ii. nonpolar-hydrophobic proteinogenic α-aminocarboxylic acids, preferably alanine, leucine, isoleucine, methionine, proline and valine,
iii. basic α-aminocarboxylic acids, preferably arginine, lysine and ornithine,
iv. non-proteinogenic aminocarboxylic acids, selected from the group comprising β-alanine, D-alanine, L-homoserine and D-valine,
v. aminocarboxylic acid polymers comprising at least one of the aminocarboxylic acids mentioned in (i.) to (iv.), preferably with a size from 0.5 kDa to 300 kDa, preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine, preferably the aminocarboxylic acid polymers consist of the aminocarboxylic acids mentioned in (i.) to (iv.),
vi. peptides from 2 to 4 aminocarboxylic acids, comprising at least one of the aminocarboxylic acids mentioned in (i.) to (iv.), preferably selected from identical or different aminocarboxylic acids mentioned in (i.) to (iv.), preferably glycine dimers, glycine trimers and glycine tetramers, preferably the peptides consist of the aminocarboxylic acids mentioned in (i.) to (iv.),
vii. a compound of the general formula $R^3R^4N-CR^1R^2-COOH$ (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, wherein the alkyl component has a chain length from C1 to C5, is branched or unbranched, is saturated or unsaturated, and wherein at least one of $R^1$, $R^2$, $R^3$ and $R^4$ is not hydrogen. One, two, three, four or five hydroxyl groups can be present in the hydroxyalkyl group. Di(hydroxyalkyl) groups and tri(hydroxyalkyl) groups are also suitable. The compound of general formula (I) is preferably selected from the group N-(tri(hydroxymethyl)methyl)glycine (tricine) and N,N-bis(2-hydroxyethyl)glycine (bicine).
viii. a compound of the general formula $R^3R^4N-CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated. One, two, three, four or five hydroxyl groups can be present in the hydroxyalkyl group. Di(hydroxyalkyl) groups and tri(hydroxyalkyl) groups are also suitable. Compound (II) is preferably Tris(hydroxymethyl)-aminomethane (Tris),
b. preferably mixing this reagent with the sample material,
c. isolating and/or purifying nucleic acids from the sample material, which has been contacted with and/or mixed with the reagent,
d. optionally quantitative and/or qualitative detection of at least a portion of the isolated nucleic acids, preferably quantitative detection by amplification of a nucleic acid segment to be detected,
wherein the method preferably also comprises one of the following features:

I. the reagent that according to step (a.) is added to the sample material does not contain a chaotropic agent or
II. if in step (c.) at least one chaotropic agent-containing reagent is added, the addition of a chaotropic agent-containing reagent occurs for the first time in the absence of a branched or unbranched alkanol with 1 to 5 carbon atoms.

In all the cases mentioned above and subsequently, the further defined "alkyl component" means, unless stated otherwise, both that in the pure alkyl group and that in the aminoalkyl, thioalkyl, hydroxyalkyl, di(hydroxyalkyl) and/or tri(hydroxyalkyl), wherein these can in each case have the stated specification independently of one another. Examples of suitable saturated, branched or unbranched C1 to C5 alkyl groups in the "alkyl component" are methyl, ethyl, 1-propyl (=n-propyl), 1-methylethyl (=isopropyl), 1-butyl (=n-butyl), 1-methylpropyl (=sec-butyl), 1,1-dimethylethyl (=tert-butyl), 2-methylpropyl (=isobutyl), 1-pentyl (=n-pentyl), 2-pentyl (=sec-pentyl), 3-pentyl, 2-methylbutyl, 3-methylbutyl (=isopentyl), 3-methylbut-2-yl, 2-methylbut-2-yl and 2,2-dimethylpropyl (=neopentyl). Methyl, ethyl, 1-propyl and 2-propyl are especially preferred.

Examples of suitable unsaturated, branched or unbranched C3 to C5 alkyl groups in the "alkyl component" are 2-propenyl, 3-butenyl, 1-methyl-2-propenyl, cis-2-butenyl, trans-2-butenyl, 2-methyl-2-propenyl, n-pentenyl, 1-methyl-3-butenyl, 1-ethyl-2-propenyl, trans-2-pentenyl, cis-2-pentenyl, 1-methyl-trans-2-butenyl, 1-methyl-cis-2-butenyl, trans-3-pentenyl, cis-3-pentenyl, 3-methyl-3-butenyl, 1,2-dimethyl-2-propenyl, 2-ethyl-2-propenyl, 2-methyl-trans-2-butenyl, 2-methyl-cis-2-butenyl, 3-methyl-trans-2-butenyl, 3-methyl-cis-2-butenyl, 2-methyl-3-butenyl, 1,1-dimethyl-2-propenyl and 2-methyl-3-butenyl.

According to an embodiment III., in step (c.) at least one lysis reagent is added to the sample material pretreated according to step (a.), prior to binding of the nucleic acids to a carrier material. The lysis reagent can actually bring about lysis, but need not necessarily always do so, depending on the requirements of the starting material. Preferred embodiments are described below.

According to an embodiment IV., the reagent used for the pretreatment in step (a.) does not have any lysing properties.

The features of embodiments I. to IV. can also be combined with one another in the method according to the invention.

According to embodiments I. to IV., and embodiments resulting from combining the features of these embodiments, the sample material comprising the nucleic acids that are to be isolated and/or purified, which is contacted with the reagent according to the invention in step (a.), is selected from one of the following groups:
A. an aqueous composition, preferably a purification fraction from a purification process, comprising biomolecules and/or organisms, wherein the biomolecules and/or organisms have at least one of the following features:
   i. the biomolecules and/or organisms are selected from the group comprising proteins, nucleic acids (preferably DNA, RNA, plasmids, small interfering RNA (siRNA)), viruses and/or vaccines,
   ii. the biomolecules and/or organisms are pharmaceutically active substances,
   iii. the biomolecules are produced synthetically or biotechnologically, and/or
   iv. the biomolecules are biotechnologically produced molecules, which are produced by genetically modified or unmodified organisms, B. human or animal body constituents selected from the group comprising body fluids, body cells and/or body tissues, preferably blood, blood constituents, serum, cerebrospinal fluid, liquor mucosal smears, sputum, urine, stool, semen and tissue samples, wherein said body constituents comprise one or more of the following molecules and/or organisms:
  i. freely circulating human or animal nucleic acids, preferably freely circulating fetal nucleic acids, nucleic acids from malignant and/or non-malignant tumours, nucleic acids from apoptotic cells, small non-coding RNA, microRNA (miRNA) and siRNA,
  ii. freely circulating nucleic acids from microorganisms, preferably from pathogens, especially preferably from bacteria and viruses, and/or
  iii. microorganisms, preferably pathogens, especially preferably bacteria and viruses,
C. forensic sample materials containing cells and/or nucleic acids and/or organisms, wherein the cells and/or nucleic acids and/or organisms are present in a liquid sample material or in a liquid extracted from the sample material, and/or
D. a composition comprising a sample component and optionally organisms, wherein the sample component is selected from the group comprising foodstuffs or constituents thereof, and constituents of the environment, preferably soil, water and vegetation, and optionally is resuspended.

Owing to the pretreatment according to the invention in step (a.), the method has the advantages described above. As a result of the pretreatment of the sample material with a special reagent, the isolation and/or purification of the nucleic acids in step (c.) is significantly improved or for some sample materials even becomes possible at all. Moreover, for example nucleic acids that are only present in the sample material in very small amounts can be isolated efficiently, effectively and even quantitatively. Thus, with the method according to the invention, nucleic acids can be isolated even if they are contained in an amount of only 1 pg or less in the sample material (isolation is possible even with amounts of 0.1 pg or 0.01 pg). Furthermore, the pretreatment according to the invention has the effect that also very different sample materials can be processed in an identical fashion, without any significant differences with respect to the efficiency of nucleic acid isolation. Experiments have shown that the method according to the invention can isolate nucleic acids efficiently, effectively and reliably even if they are present in very diverse sample materials, which for example have varying pH values in the range from 3 to 9, have a very different chemical composition and/or have different salt concentrations. Even if the method according to the invention is used with such different sample materials, due to the pretreatment according to the invention the method provides reliably good isolation results. Therefore the method according to the invention opens up fields of use that so far have not been served satisfactorily by the prior art. In particular, a quantitative isolation of nucleic acids also becomes possible, even if they are only present in small amounts in the sample material. Furthermore, the method according to the invention is suitable for manual and for automated performance, which is advantageous especially when processing a large number of samples.

An important feature of the method is in step (a.) the use of a special reagent before performing the steps for nucleic acid isolation and/or purification that are known from the prior art. This pretreatment has the effect that the nucleic acids present in the sample material can then be purified efficiently and effectively, even if they are only present in small amounts in various sample materials and/or are isolated from sample materials which, owing to their composition, do not allow an isolation without further, as is the case for example with bioprocess samples. Surprisingly, the reagent used in step (a.) compensates differences in the sample materials and as a result enables a reliable isolation of the nucleic acids by using a uniform method. Furthermore, it enables for nucleic acids to be isolated even from sample materials from which isolation would not be possible without the pretreatment according to the invention.

The reagent used in step (a.) of the method according to the invention for pretreating of the sample material comprises at least one or more compounds comprising an amino group from the groups (i.) to (viii.) described above. If two or more compounds with an amino group are present in the reagent, for example mixtures of the components within and/or between the groups (i.) to (viii.) can be present. The compounds can also be added separately from one another for the pretreatment in step (a.). This embodiment shall also represent a pretreatment in the sense of the invention with the reagent according to the invention according to step (a.).

The reagent used according to the invention in step (a.) is therefore suitable in various embodiments for sample preparation for subsequent nucleic acid isolation and/or purification: for example, one or more polar-neutral proteinogenic α-aminocarboxylic acids such as asparagine and/or cysteine and/or glutamine and/or glycine and/or threonine and/or serine can be comprised. Moreover, one or more nonpolar-hydrophobic proteinogenic α-aminocarboxylic acids, for example alanine and/or leucine and/or isoleucine and/or methionine and/or proline and/or valine can also be comprised in the reagent, as well as one or more basic α-aminocarboxylic acids such as for example arginine and/or lysine and/or ornithine. One or more non-proteinogenic aminocarboxylic acids, for example β-alanine and/or D-alanine and/or L-homoserine and/or D-valine can also be comprised. Aminocarboxylic acid polymers may preferably be formed from identical, or two or more different aminocarboxylic acid monomers of the group of polar-neutral proteinogenic α-aminocarboxylic acids and/or the group of nonpolar-hydrophobic proteinogenic α-aminocarboxylic acids and/or the group of basic α-aminocarboxylic acids and/or the group of non-proteinogenic aminocarboxylic acids can also be comprised in the reagent. Peptides from 2 to 4 aminocarboxylic acids, preferably selected from identical or different aminocarboxylic acids of the group of polar-neutral proteinogenic α-aminocarboxylic acids and/or the group of non-polar-hydrophobic proteinogenic α-aminocarboxylic acids and/or the group of basic α-aminocarboxylic acids and/or the group of non-proteinogenic aminocarboxylic acids can also be comprised in the reagent. One or more compounds of the general formula $R^3R^4N-CR^1R^2-COOH$ (I) can also be comprised in the reagent, wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl and hydroxyalkyl, wherein the alkyl component has a chain length from C1 to C5, is branched or unbranched, is saturated or unsaturated, and wherein at least one of the residues of $R^1$, $R^2$, $R^3$ and $R^4$ is not hydrogen. Preferably this compound is selected from the group N-(tri(hydroxymethyl)methyl)glycine (tricine) and/or N,N-bis(2-hydroxyethyl)glycine (bicine). Moreover, one or more compounds of general formula $R^3R^4N-CR^5R^6R^7$ (II) can also be comprised in the reagent, wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of the residues of $R^5$, $R^6$ and $R^7$ is a hydroxyalkyl, and wherein the alkyl component has a chain length from C1 to C5, is branched or unbranched, is saturated or unsaturated. A preferred compound corresponding to this formula is the compound Tris(hydroxymethyl)-aminomethane (Tris).

According to a preferred embodiment the pH of the reagent is in the range from pH 3 to pH 9. As shown in the examples, the reagent according to the invention can have an acidic as well as a basic pH.

According to one embodiment of the reagent according to the invention, the reagent comprises aminocarboxylic acid polymers preferably in a size from 0.5 kDa to 300 kDa. The aminocarboxylic acid polymers can be present as homopolymers from identical aminocarboxylic acid monomers or as copolymers from two or more different aminocarboxylic acid monomers, wherein the monomers are arranged in the polymer chain so that they are alternating, randomly distributed, in gradient or block form. Both polymer types are preferably formed from aminocarboxylic acid monomers of groups (i.) polar-neutral proteinogenic α-aminocarboxylic acids and/or (ii.) nonpolar-hydrophobic proteinogenic α-aminocarboxylic acids and/or (iii.) basic α-aminocarboxylic acids and/or (iv.) non-proteinogenic aminocarboxylic acids, preferably in conjunction with hydrohalides such as for example hydrobromide or hydrochloride. Compounds that are preferably selected are poly-L-lysine, poly-L-lysine hydrobromide, poly-L-lysine hydrochloride, poly(L-glutamine, L-alanine), poly(L-glutamine, L-lysine) hydrobromide, poly-L-ornithine. Moreover, polymers are also included that are formed from non-proteinogenic enantiomeric forms, such as for example poly-D-lysine, poly-D-lysine hydrobromide, poly(D-glutamine, D-lysine) hydrobromide.

If an embodiment of the reagent according to the invention contains peptides from 2 to 4 aminocarboxylic acids, these are preferably selected from identical or different aminocarboxylic acids of groups (i.) polar-neutral proteinogenic α-aminocarboxylic acids and/or (ii.) nonpolar-hydrophobic proteinogenic α-aminocarboxylic acids and/or (iii.) basic α-aminocarboxylic acids and/or (iv.) non-proteinogenic aminocarboxylic acids. Preferably, peptide compounds are formed from the preferably described molecules asparagine, cysteine, glutamine, glycine, threonine, serine, alanine, leucine, isoleucine, methionine, proline, valine, arginine, lysine, ornithine, β-alanine, D-alanine, L-homoserine and D-valine, wherein any combinations of these molecules as dimer, trimer or tetramer are possible. The following examples comprise peptide compounds from 2 aminocarboxylic acids: asparagine-asparagine, asparagine-cysteine, asparagine-glutamine, asparagine-glycine, asparagine-threonine, asparagine-serine, asparagine-alanine, asparagine-leucine, asparagine-isoleucine, asparagine-methionine, asparagine-proline, asparagine-valine, asparagine-arginine, asparagine-lysine, asparagine-ornithine, asparagine-β-alanine, asparagine-D-alanine, asparagine-L-homoserine, asparagine-D-valine, cysteine-asparagine, cysteine-cysteine, cysteine-glutamine, cysteine-glycine, cysteine-threonine, cysteine-serine, cysteine-alanine, cysteine-leucine, cysteine-isoleucine, cysteine-methionine, cysteine-proline, cysteine-valine, cysteine-arginine, cysteine-lysine, cysteine-ornithine, cysteine-β-alanine, cysteine-D-alanine, cysteine-L-homoserine, cysteine-D-valine, glutamine-asparagine, glutamine-cysteine, glutamine-glutamine, glutamine-glycine, glutamine-threonine, glutamine-serine, glutamine-alanine, glutamine-leucine, glutamine-isoleucine, glutamine-methionine, glutamine-proline, glutamine-valine, glutamine-arginine, glutamine-lysine, glutamine-ornithine, glutamine-β-alanine, glutamine-D-alanine, glutamine-L-homoserine, glutamine-D-valine, glycine-asparagine, glycine-cysteine, glycine-glutamine, glycine-glycine, glycine-threonine, glycine-serine, glycine-alanine, glycine-leucine, glycine-isoleucine, glycine-methionine, glycine-proline, glycine-valine, glycine-arginine, glycine-lysine, glycine-ornithine, glycine-β-alanine, glycine-D-alanine, glycine-L-homoserine, glycine-D-valine, threonine-asparagine, threonine-cysteine, threonine-glutamine, threonine-glycine, threonine-threonine, threonine-serine, threonine-alanine, threonine-leucine, threonine-isoleucine, threonine-methionine, threonine-proline, threonine-valine, threonine-arginine, threonine-lysine, threonine-ornithine, threonine-β-alanine, threonine-D-alanine, threonine-L-homoserine, threonine-D-valine, serine-asparagine, serine-cysteine, serine-glutamine, serine-glycine, serine-threonine, serine-serine, serine-alanine, serine-leucine, serine-valine, serine-arginine, serine-lysine, serine-ornithine, serine-β-alanine, serine-D-alanine, serine-L-homoserine, serine-D-valine, alanine-asparagine, alanine-cysteine, alanine-glutamine, alanine-glycine, alanine-threonine, alanine-serine, alanine-alanine, alanine-leucine, alanine-isoleucine, alanine-methionine, alanine-proline, alanine-valine, alanine-arginine, arginine-lysine, arginine-ornithine, alanine-β-alanine, alanine-D-alanine, alanine-L-homoserine, alanine-D-valine, leucine-asparagine, leucine-cysteine, leucine-glutamine, leucine-glycine, leucine-threonine, leucine-serine, leucine-alanine, leucine-leucine, leucine-isoleucine, leucine-methionine, leucine-proline, leucine-valine, leucine-arginine, leucine-lysine, leucine-ornithine, leucine-β-alanine, leucine-D-alanine, leucine-L-homoserine, leucine-D-valine, isoleucine-asparagine, isoleucine-cysteine, isoleucine-glutamine, isoleucine-glycine, isoleucine-threonine, isoleucine-serine, isoleucine-alanine, isoleucine-leucine, isoleucine-isoleucine, isoleucine-methionine, isoleucine-proline, isoleucine-valine, isoleucine-arginine, isoleucine-lysine, isoleucine-ornithine, isoleucine-β-alanine, isoleucine-D-alanine, isoleucine-L-homoserine, isoleucine-D-valine, methionine-asparagine, methionine-cysteine, methionine-glutamine, methionine-glycine, methionine-threonine, methionine-serine, methionine-alanine, methionine-leucine, methionine-isoleucine, methionine-methionine, methionine-proline, methionine-valine, methionine-arginine, methionine-lysine, methionine-ornithine, methionine-β-alanine, methionine-D-alanine, methionine-L-homoserine, methionine-D-valine, proline-asparagine, proline-cysteine, proline-glutamine, proline-glycine, proline-threonine, proline-serine, proline-alanine, proline-leucine, proline-isoleucine, proline-methionine, proline-proline, proline-valine, proline-arginine, proline-lysine, proline-ornithine, proline-β-alanine, proline-D-alanine, proline-L-homoserine, proline-D-valine, valine-asparagine, valine-cysteine, valine-glutamine, valine-glycine, valine-threonine, valine-serine, valine-alanine, valine-leucine, valine-isoleucine, valine-methionine, valine-proline, valine-valine, valine-arginine, valine-lysine, valine-ornithine, valine-β-alanine, valine-D-alanine, valine-L-homoserine, valine-D-valine, arginine-asparagine, arginine-cysteine, arginine-glutamine, arginine-glycine, arginine-threonine, arginine-serine, arginine-alanine, arginine-leucine, arginine-isoleucine, arginine-methionine, arginine-proline, arginine-valine, arginine-arginine, arginine-lysine, arginine-ornithine, arginine-β-alanine, arginine-D-alanine, arginine-L-homoserine, arginine-D-valine, lysine-asparagine, lysine-cysteine, lysine-glutamine, lysine-glycine, lysine-threonine, lysine-serine, lysine-alanine, lysine-leucine, lysine-isoleucine, lysine-methionine, lysine-proline, lysine-valine, lysine-arginine, lysine-lysine, lysine-ornithine, lysine-β-alanine, lysine-D-alanine, lysine-L-homoserine, lysine-D-valine, ornithine-asparagine, ornithine-cysteine, ornithine-glutamine, ornithine-glycine, ornithine-threonine, ornithine-serine, ornithine-alanine, ornithine-leucine, ornithine-isoleucine, ornithine-methionine, ornithine-proline, ornithine-valine, ornithine-arginine, ornithine-lysine, ornithine-ornithine, ornithine-β-alanine, ornithine-D-alanine, ornithine-L-homoserine, ornithine-D-valine, β-alanine-asparagine, β-alanine-cysteine, β-alanine-glutamine, β-alanine-glycine, β-alanine-threonine, β-alanine-serine, β-alanine-alanine, β-alanine-leucine, β-alanine-isoleucine, β-alanine-methionine, β-alanine-proline, β-alanine-valine, β-alanine-arginine, β-alanine-lysine, β-alanine-ornithine, β-alanine-β-alanine, β-alanine-D-alanine, β-alanine-L-homoserine, β-alanine-D-valine, D-alanine-asparagine, D-alanine-cysteine, D-alanine-glutamine, D-alanine-glycine, D-alanine-threonine, D-alanine-serine, D-alanine-alanine, D-alanine-leucine, D-alanine-isoleucine, D-alanine-methionine, D-alanine-proline, D-alanine-valine, D-alanine-arginine, D-alanine-lysine, D-alanine-ornithine, D-alanine-β-alanine, D-alanine-D-alanine, D-alanine-L-homoserine, D-alanine-D-valine, L-homoserine-asparagine, L-homoserine-cysteine, L-homoserine-glutamine, L-homoserine-glycine, L-homoserine-threonine, L-homoserine-serine, L-homoserine-alanine, L-homoserine-leucine, L-homoserine-isoleucine, L-homoserine-methionine, L-homoserine-proline, L-homoserine-valine, L-homoserine-arginine, L-homoserine-lysine, L-homoserine-ornithine, L-homoserine-β-alanine, L-homoserine-D-alanine, L-homoserine-L-homoserine, L-homoserine-D-valine, D-valine-asparagine, D-valine-cysteine, D-valine-glutamine, D-valine-glycine, D-valine-threonine, D-valine-serine, D-valine-alanine, D-valine-leucine, D-valine-isoleucine, D-valine-methionine, D-valine-proline, D-valine-valine, D-valine-arginine, D-valine-lysine, D-valine-ornithine, D-valine-β-alanine, D-valine-D-alanine, D-valine-L-homoserine, D-valine-D-valine. Analogously to the described peptide compounds, which are combined from 2 aminocarboxylic acids, peptide compounds with 3 to 4 aminocarboxylic acids are also possible.

According to a preferred embodiment, the peptide from 2 to 4 aminocarboxylic acids it is about the glycine-glycine dimer, and preferably is the glycine-glycine-glycine trimer and/or is the glycine-glycine-glycine-glycine tetramer.

When using the reagent in the method according to the invention for isolation and/or purification of nucleic acids according to one embodiment in the reaction mixture of sample material and the reagent used in step (a.) for the pretreatment, the total concentration of the compound comprising an amino group and/or of combinations of various of these compounds is 2.5 mM to 400 mM, preferably 12.5 mM to 280 mM, especially preferably 25 mM to 200 mM. These concentrations have proved especially advantageous with a reaction mixture of sample material and reagent in a size from 200 µl to 1000 µl. Here, a quantitative isolation of the nucleic acids was possible, even if the reaction mixture of reagent according to the invention and sample material only contained small amounts of nucleic acids in the order of only 1 pg of nucleic acid. Recovery rates of more than 50% were achieved. The reagent used according to the invention in step (a.) preferably comprises the compound comprising an amino group and/or combinations of various of these compounds in a total concentration of 5 mM to 500 mM, preferably 25 mM to 350 mM, especially preferably 50 mM to 250 mM.

According to a preferred embodiment of the method according to the invention, a reagent is used in step (a.) that further comprises at least one or more of the following components:
  at least one detergent or mixtures of detergents,
  at least one complexing agent or mixtures of complexing agents, and/or
  at least one protein or mixtures of proteins.

If the reagent contains several components or ingredients, these can be added in the form of a homogeneous reagent, i.e. for example a solution, or alternatively the reagent can be formed by mixing two or more formulations, which are for example contacted with the sample material either together or optionally even separately from one another, for pretreating the sample material according to step (a.). The separate addition of the individual components is encompassed according to the invention by the term addition of a reagent to the sample material. Preferably, however, the components or ingredients are added in the form of one homogeneous reagent.

The detergent or the mixtures of detergents that may be contained in the reagent used for the pretreatment are preferably selected from the group of non-ionic surfactants and especially preferably are selected from the group of the alkylglucosides and/or polyoxyethylene-alkylphenyl ethers. The group of the alkylglucosides comprises in particular the group of the polysorbates, preferably polysorbate 20, polysorbate 40 and polysorbate 80, and especially preferably polysorbate 20 (Tween 20). The group of the polyoxyethylene-alkylphenyl ethers preferably comprises octoxynol 9 (Triton X-100) and Nonidet P-40. The presence of a detergent or of a mixture of detergents in step (a.) can have beneficial effects on the pretreatment. Thus, the recovery rate of the nucleic acids that are to be purified and hence the efficiency of nucleic acid isolation can be increased advantageously by adding at least one detergent, as is also clearly demonstrated by the examples. The detergent is preferably a constituent of the reagent according to the invention; however, as described, it can also be added separately for pretreating the sample material. Preferably the total concentration of the detergent or mixture of detergents, in particular of the non-ionic surfactant or non-ionic surfactants in the reagent, is 0.1% (v/v) to 5% (v/v), preferably 0.2% (v/v) to 4% (v/v), and preferably 0.5% (v/v) to 3% (v/v) and also preferably 1% (v/v) to 3% (v/v). 0.2% (v/v) to 0.5% (v/v) are preferred in particular for the use of polyoxyethylene-alkylphenyl ethers such as for example Triton X-100 and preferably 1% (v/v) to 5% (v/v) in particular for the use of alkylglucosides, in particular of polysorbates such as for example Tween 20.

The total concentration of the detergent or the mixture of detergents contained in the reagent, in particular of the non-ionic surfactant or non-ionic surfactants in the reaction mixture of sample material and reagent according to the invention is according to one embodiment 0.05% (v/v) to 4% (v/v), preferably 0.1% (v/v) to 3% (v/v), and preferably 0.25% (v/v) to 2.5% (v/v) and also preferably 0.5% (v/v) to 2.5% (v/v). Preferably values from 0.1% (v/v) to 0.4% (v/v) have proved especially advantageous for the use in particular of polyoxyethylene-alkylphenyl ethers, for example Triton X-100. According to one embodiment the concentration is preferably 0.5% (v/v) to 4% (v/v). This concentration is advantageous in particular for the use of polysorbates, for example Tween 20. The aforementioned concentrations have proved especially advantageous for a reaction mixture of sample material and reagent ranging in size from 200 µl to 1000 µl. Here, a quantitative isolation of the nucleic acids was possible, even if the reaction mixture only contained 1 pg of nucleic acid or less. Recovery rates of more than 50% and even above 75% and in many cases even above 85% were achieved. Preferably the reagent used in step (a.) for the pretreatment of the sample material contains at least two detergents. According to one embodiment, one detergent is selected from the group of alkylglucosides, preferably the polysorbates, especially preferably polysorbate 20 and the other detergent is selected from the group of polyoxyethylene-alkylphenyl ethers, and is preferably Triton X-100.

According to one embodiment of the method according to the invention the reagent used in step (a.) for the pretreatment contains a complexing agent or mixtures of complexing agents. As described, the reagent can also consist of several compositions, which are first combined or mixed for the pretreatment, so that the complexing agent can also be added separately in step (a.) for pretreating the sample material. Preferably, however, the complexing agent is a constituent of a homogeneous reagent, i.e. a solution that is used for the pretreatment of the sample material. The complexing agent is preferably selected from the group comprising ethylenediamine tetraacetic acid (EDTA), ethylene glycol-bis(aminoethylether)-N,N'-tetraacetic acid (EGTA) and/or ethylenediamine disuccinic acid (EDDS). Especially preferably, EDTA is used.

According to one embodiment, the total concentration of the complexing agent(s) in the reagent is 10 mM to 500 mM, preferably 10 mM to 300 mM, 10 mM to 200 mM and more preferably 10 mM to 100 mM. According to one embodiment, the total concentration in the reaction mixture of sample and reagent according to the invention is 5 mM to 400 mM, preferably 5 mM to 80 mM for the complexing agent(s) comprised in the reagent. These concentrations proved especially advantageous in the method according to the invention if the reaction mixture of reagent according to the invention and sample material had a size from 200 µl to 1000 µl and only contained 1 pg of nucleic acid. Here, recovery rates of more than 75% and sometimes even above 85% were achieved.

In a special embodiment, the reagent contains the compound Tris(hydroxymethyl)-aminomethane (Tris), but no EDTA and/or EGTA.

According to one embodiment of the method according to the invention the reagent used in step (a.) for the pretreatment contains at least one protein, preferably a globular protein or mixtures of globular proteins. As described, the reagent can also consist of several compositions, which are first combined or mixed for the pretreatment, so that the protein can also be added separately in step (a.) for pretreating the sample material. Preferably, however, the protein is a constituent of a homogeneous reagent, i.e. a solution that is used for the pretreatment of the sample material. According to one embodiment, the protein does not have any enzymatic activity. Preferably it is not an enzyme. The globular protein is preferably selected from the group of albumins and/or globulins. The albumins are selected from animal, plant and/or human albumin, preferably bovine serum albumin (BSA). The globulins are selected from animal, plant, and/or human globulin, preferably they are immunoglobulins such as preferably γ-globulin is used. Surprisingly, it proved advantageous if the reagent used in step (a.) for the pretreatment of the sample material contains a corresponding protein. As a result, once again the efficiency of nucleic acid purification could be increased, especially if the sample material only had a low protein concentration. The use of a corresponding protein in the reagent used in step (a.) therefore improves the nucleic acid purification, especially if the sample materials to be processed comprise only small amounts of protein and/or show differences with respect to the protein concentration According to one embodiment of the method according to the invention, the total concentration of the protein or proteins in the reagent used in step (a.) is 1 mg/mL to 100 mg/mL, preferably 2 mg/mL to 25 mg/mL, 2 mg/ml to 10 mg/ml and more further preferably 4 mg/ml to 10 mg/ml. Concentrations of 2 mg/mL to 25 mg/mL, 2 mg/ml to 10 mg/ml and preferably 4 mg/ml to 10 mg/ml are especially suitable for globular proteins, such as in particular IgG and BSA.

According to one embodiment, the total concentration in the reaction mixture of sample and reagent according to the invention is for the protein or proteins contained in the reagent 0.5 mg/mL to 80 mg/mL, 1 mg/mL to 20 mg/mL, preferably 1 mg/mL to 8 mg/mL, preferably 2 mg/mL to 8 mg/mL. These concentrations proved especially advantageous in the method according to the invention if the reaction mixture of reagent according to the invention and sample material had a size of 200 µl to 1000 µl. Here, a quantitative isolation of the nucleic acids was possible, even if the reaction mixture only contained 1 pg of nucleic acid or less. In this case recovery rates of more than 75%, sometimes even above 85% were achieved. The concentrations stated for the protein are especially suitable for globular proteins such as in particular IgG and BSA.

According to one embodiment, the reagent used in step (a.) does not contain phosphate and/or citrate in an overall concentration ≥5 mM, wherein in particular no free phosphate is present. It has been found that in particular excessive phosphate concentrations can have an inhibitory effect on the nucleic acid isolation and/or purification, especially when purifying nucleic acids from bioprocess samples.

According to one embodiment, the reagent comprises at least one or more compounds comprising an amino group, selected from one or more of the following groups i. to viii:
  i. asparagine, cysteine, glutamine, glycine, threonine and serine,
  ii. alanine, leucine, isoleucine, methionine, proline and valine,
  iii. arginine, lysine and ornithine,
  iv. β-alanine, D-alanine, L-homoserine and D-valine,
  v. poly-L-lysine, poly-L-lysine hydrobromide, poly-L-lysine hydrochloride, poly(L-glutamine, L-alanine), poly(L-glutamine, L-lysine) hydrobromide, poly-L-ornithine,
  vi. glycine dimers, glycine trimers, glycine tetramers and the dipeptide (Ala-Glu),
  vii. N-(tri(hydroxymethyl)methyl)glycine (tricine) and N,N-bis(2-hydroxyethyl)glycine (bicine), and/or
  viii. Tris(hydroxymethyl)-aminomethane (Tris).

Especially preferred embodiments of the reagent are described below. In these preferred embodiments, the individual components of the reagent are preferably present in the concentrations stated above for the individual constituents, in this respect it is referred to the above disclosure. As described, the individual constituents of the reagent can also be added separately during the pretreatment of the sample material, wherein, however, addition in a homogeneous reagent, i.e. a solution, is preferred.

According to a preferred embodiment the reagent used in step (a.) comprises at least glycine, Gly-Gly, tricine and/or bicine as compound comprising an amino group, at least one complexing agent, preferably EDTA, and at least one, preferably at least two detergents, especially preferably a polyoxyethylene-alkylphenyl ether such as Triton X-100 and/or a polysorbate such as preferably Tween 20. Especially preferably the reagent comprises additionally at least one protein, preferably a globular protein such as IgG or BSA.

According to one embodiment, the reagent according to the invention used in step (a.) comprises one or more polar-neutral and/or basic α-aminocarboxylic acids from the group of asparagine, glutamine, arginine, lysine and ornithine. Here, experiments have shown that a pretreatment with a corresponding reagent can further improve the isolation and/or purification, especially if this/these α-aminocarboxylic acid(s) are combined with a buffer, such as in particular a Tris or sulphonic acid buffer, for example a HEPES or HEPPS buffer. Furthermore, the reagent preferably comprises at least one protein, preferably a globular protein such as IgG or BSA.

According to another preferred embodiment the reagent used in step (a.) comprises the aminocarboxylic acid compounds glutamine, proline, poly-L-lysine and/or poly(L-glutamine, L-alanine) and the dipeptide (Ala-Glu). Preferably it also comprises a complexing agent, for example EGTA, and at least one, preferably at least two detergents, especially preferably a polyoxyethylene-alkylphenyl ether such as Nonidet-P 40 and/or a polysorbate such as preferably Tween 20. More preferably, the reagent also comprises a globular protein, preferably IgG and one or more buffers, preferably one or two sulphonic acid buffers, for example HEPES and/or HEPPS.

According to another preferred embodiment the reagent used in step (a.) comprises at least one, preferably both aminocarboxylic acid compounds β-alanine and poly(L-glutamine, L-alanine). Preferably it also comprises a complexing agent, for example EDTA, and at least one, preferably at least two detergents, especially preferably a polyoxyethylene-alkylphenyl ether such as Triton X-100 and/or a polysorbate such as preferably polysorbate 40. Preferably the reagent also comprises a globular protein, preferably IgG and one or more buffers, preferably one or two sulphonic acid buffers, for example HEPES and/or HEPPS.

According to another preferred embodiment the reagent used in step (a.) comprises at least two, preferably all of the aminocarboxylic acid compounds cysteine, alanine, arginine, poly-L-lysine hydrobromide and tris(hydroxymethyl)-aminomethane (Tris). Moreover, this reagent preferably comprises a globular protein, in particular an IgG.

According to another preferred embodiment the reagent used in step (a.) comprises at least two, preferably all of the aminocarboxylic acid compounds serine, methionine, lysine, D-valine and poly-L-ornithine. Preferably it also comprises a complexing agent, for example EGTA, and at least one, preferably at least two detergents, especially preferably a polyoxyethylene-alkylphenyl ether such as Triton X-100 and/or a polysorbate such as preferably Tween 20. Preferably the reagent also comprises a globular protein, preferably BSA.

According to another preferred embodiment the reagent used in step (a.) comprises at least two, preferably all of the aminocarboxylic acid compounds threonine, leucine and ornithine. Preferably it also comprises a complexing agent, for example EDDS, and at least one, preferably at least two detergents, especially preferably a polyoxyethylene-alkylphenyl ether such as Triton X-100 and/or a polysorbate such as preferably Tween 20. Preferably the reagent additionally comprises a protein, preferably a globular protein such as IgG or BSA, and further preferably one or more buffers, preferably one or two sulphonic acid buffers, for example HEPES and/or HEPPS.

The method according to the invention for the isolation and/or purification of nucleic acids is characterized by the succession of several steps from the provided sample material to the optional, preferably quantitative detection of at least a portion of the isolated nucleic acids. The individual steps and preferred embodiments are explained in detail below.

The described embodiments can also be combined with one another.

In a basic embodiment of the method, in step (a) occurs the preparation according to the invention of the sample material for the isolation and/or purification of the nucleic acids contained in the sample material. This is effected by adding the special reagent, which has already been described in detail above, to the sample material. If the reagent comprises several components, these can also be added separately from one another in the sense of a building-block system, for pretreating the sample material in step (a.) with the reagent according to the invention. Preferably, however, the components are added in the form of a homogeneous reagent, i.e. a solution. An optional mixing step (b.) is followed by the actual isolation and/or purification of the nucleic acids (step c.) and then optionally by the detection of at least a portion of the isolated nucleic acids (step d.).

The method according to the invention can have one or more of the following features:

According to one embodiment, the reagent according to the invention, which is added to the sample material in step (a.), does not contain a chaotropic agent. The term "chaotropic agent" refers according to one embodiment to chaotropic compounds and therefore compounds that have a denaturing effect on proteins and which, in particular, destroy the regular structure of liquid water, that is based on the formation of hydrogen bridge bonds. In particular, the term "chaotropic agent" refers to chaotropic salts, such as in particular sodium or guanidinium salts, preferably selected from the group comprising sodium iodide, sodium perchlorate, guanidinium hydrochloride, guanidinium thiocyanate, guanidinium isothiocyanate and/or a mixture of two or more salts thereof. This embodiment without a chaotropic agent is advantageous, because tests have shown that chaotropic compounds, such as in particular chaotropic salts, in the reagent that is used in step (a) for pretreatment, in particular in higher concentrations can have an adverse effect on the subsequent nucleic acid purification. Therefore the reagent used for pretreatment in step (a.) preferably does not contain a chaotropic agent in concentrations that disturb the subsequent nucleic acid isolation and in particular in concentrations which make the pretreatment according to the invention less effective. Preferably the reagent used in step (a.) of the method according to the invention does not contain any chaotropic agent at all or no chaotropic agent is added in step (a.) at all.

According to a second embodiment, in step (c) a chaotropic agent containing reagent is added for the first time in the absence of a branched or unbranched alkanol with 1 to 5 carbon atoms, if at least one chaotropic agent containing reagent is added in step (c.). A chaotropic agent containing reagent can be added in step (c.) e.g. in order to digest the pretreated sample material. However, following the addition of a chaotropic agent containing reagent for the first time in step (c.), which according to this embodiment occurs in the absence of a branched or unbranched alcohol, subsequently branched or unbranched alkanols with 1 to 5 carbon atoms can be used once again, for example for adjusting the binding conditions and/or in the optional washing steps. These subsequent steps can moreover take place in the presence or absence of chaotropic compounds.

According to a third embodiment, in step (c.) at least one lysis reagent is added to the sample material that has been pretreated according to step (a.), prior to binding the nucleic acids to a carrier material. Classical lysis reagents that can be used for this purpose are for example enzymes, in particular proteolytic enzymes, preferably proteases such as for example proteinase K, and lysis reagents that contain chaotropic compounds such as preferably chaotropic salts and/or detergents, preferably non-ionic detergents. Thereby a digestion of the sample material pretreated according to step (a.) occurs. According to one embodiment, the sample material pretreated according to step (a.) is contacted in step (c.) with at least one proteolytic enzyme and at least one further lysis reagent, which preferably contains a chaotropic compound, and is incubated, prior to binding the nucleic acids to a carrier material. The duration of the incubation step is, according to one embodiment, at least 3 min, preferably at least 5 min, preferably at least 10 min, especially preferably at least 15 min and is preferably carried out at a temperature at which the proteolytic enzyme used has an increased activity. Preferably the incubation step is carried out at at least 35° C., at least 40° C., at least 50° C., at least 55° C. or at least 60° C. Preferably, the incubation is carried out in a temperature range from 35° C. to 70° C., preferably from 40° C. to 65° C. Especially preferably, a combination of a proteolytic enzyme and a chaotropic agent containing lysis reagent is used. Details of this digestion step are also explained below. According to a preferred embodiment, following incubation at least one alcohol and/or at least one chaotropic compound is added for adjusting the binding conditions. This embodiment is explained in more detail below (see in particular partial steps c.1) and c.2)).

According to a fourth embodiment, the reagent used in step (a.) for the pretreatment of the sample material does not have any lysing properties and accordingly cannot lyse the sample material.

As described, the embodiments described above can also be combined with one another.

The preparation of the sample material in step (a.) according to the invention can occur in various ways, for example by adding the reagent according to the invention to the provided sample material or also in the reverse order, by adding the sample material to the provided reagent. Reagent and sample material are preferably added together in step (a.) in the following ratio: 1+4 ($V_{reagent}+V_{sample\ material}$) to 4+1 ($V_{reagent}+V_{sample\ material}$), preferably 1+2 ($V_{reagent}+V_{sample\ material}$) to 2+1 ($V_{reagent}+V_{sample\ material}$) and especially preferably 1+1 ($V_{reagent}+V_{sample\ material}$). A subsequent mixing step (b.) should preferably be carried out.

The pretreatment in step (a.) according to the invention and optionally step (b.) is then followed by step (c.) of isolation and/or purification. Optionally, the composition of the reagent according to the invention and the sample material that results from step (a.) or step (a.) and (b.) can be further processed and/or treated prior to step (c.), for example by adding further formulations or by separating individual constituents. For simplicity, compositions that result from corresponding intermediate steps, are also designated within the context of the present application as compositions of reagent according to the invention and sample material resulting from step (a.) or step (a.) and (b.).

Step (c.), which depending on the embodiment can have several sub-steps, functions basically with any kind of methods for isolating nucleic acids. According to one embodiment the isolation and/or purification of the nucleic acids in step (c.) comprises at least one of the following sub-steps c.1) and c.2), preferably both sub-steps:

c.1) Digestion of the composition of the reagent according to the invention and the sample material that results from step (a.) or step (a.) and (b.). This digestion serves in particular for the denaturation and/or degradation of any proteins that might be present in the sample material and any other contaminating sample constituents that might be present. Moreover, this step can also serve the purpose—depending on the sample material—of releasing the nucleic acids contained in the sample material from for example complexing substances. In this digestion step c.1) it is possible to use classical lysis reagents, for example proteolytic enzymes, in particular proteases such as preferably proteinase K, and lysis reagents that contain at least one chaotropic compound such as preferably a chaotropic salt and/or at least one detergent, preferably a non-ionic detergent. Preferred embodiments of suitable lysis reagents are also described below (see for example the formulation used in sub-step ii. of the preferred embodiment of step (c.) explained below). Further lysis reagents, which can preferably be used in step c.1), are for example also described in WO 2009/144182, to which reference is hereby made. According to a preferred embodiment the digestion in step c.1) is carried out using at least one proteolytic enzyme and at least one further lysis reagent, which comprises at least one chaotropic compound and/or at least one detergent, preferably at least one non-ionic detergent. For the digestion step, the sample material pretreated according to step (a.) is contacted, in step c.1), according to one embodiment with at least one proteolytic enzyme and at least one further lysis reagent, preferably containing at least one chaotropic compound, and is incubated. The duration of the incubation step is preferably at least 3 min, preferably at least 5 min, and especially preferably at least 10 min, and is preferably carried out at temperatures at which the proteolytic enzyme has increased activity. Preferably the incubation step is carried out at at least 30° C., at least 35° C., at least 40° C., at least 50° C., at least 55° C. or at least 60° C. Preferably the incubation is carried out in a temperature range from 35° C. to 70° C., preferably from 40° C. to 65° C. Especially preferably, a combination of a proteolytic enzyme and a chaotrope-containing lysis reagent is used.

c.2) Isolation of the nucleic acids, preferably by binding to a carrier material. The nucleic acid-binding carrier material is preferably a nucleic acid-binding solid phase, which can for example be selected from the group of silica-containing materials, silica gel, silicon dioxide, glass, zeolite, aluminium oxide, titanium dioxide, zirconium dioxide, kaolin, ceramics, polymeric carrier materials such as for example polyalkylenes, e.g. PE, PP or PE/PP, and polystyrene beads. Finally, what is decisive is that the carrier material is able to bind the nucleic acids under the chosen binding conditions. The carrier material can be modified with functional groups such as for example anion exchanger groups, or alternatively it can be unmodified and accordingly bears no additional functional groups on the surface. Further suitable carrier materials are also described below. The binding conditions can, according to one embodiment, be adjusted or predefined by the lysis reagent used in step c.1), for example if the latter comprises a chaotropic compound in a suitable concentration. A corresponding binding step is described in the prior art, for example in U.S. Pat. No.

5,234,809. Preferably, however, for adjusting the binding conditions, a binding reagent is added, comprising at least one alcohol, preferably a branched or unbranched alkanol with 1 to 5 carbon atoms, especially preferably isopropanol. The binding reagent can further contain at least one chaotropic compound, preferably a chaotropic salt and/or at least one detergent. The detergent is preferably a non-ionic detergent. Preferred embodiments are also described below (see for example the formulation used in sub-step iv. of the preferred embodiment of step (c.) explained below). Further binding reagents that can be used in step c.2) are described for example in WO 2009/144182, to which reference is hereby made. Binding of the nucleic acids to the carrier material is preferably followed by separation of the nucleic acids from the remaining sample. This generally takes place by separating the nucleic acids bound to the carrier material—if using magnetic silica particles, usually with the aid of a magnetic field—from the remaining sample. Optionally, the nucleic acids can then be washed and eluted.

According to an especially suitable embodiment, the isolation and/or purification of the nucleic acids in step (c.) comprises the following sub-steps:

i. optionally degradation of proteins and/or contaminating sample constituents by adding one or more enzymes, preferably proteolytic enzymes such as proteinase K, optionally in combination with a chaotropic agent containing reagent, preferably in the absence of a branched or unbranched alkanol, to the composition of sample material and reagent, which is optionally mixed, ii. adding a formulation comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety, which contains 2 to 150 ($CH_2CH_2O$) units, preferably for adjusting or predefining the binding conditions for the binding of nucleic acids, iii. optionally mixing and/or incubating, preferably at temperatures at which the enzyme added according to i. has increased activity, preferably at temperatures above 35° C. (suitable temperatures for proteolytic enzymes are also described above), iv. adding a formulation comprising at least one branched or unbranched alkanol with one to five carbon atoms, and optionally additionally a chaotropic compound and/or optionally a detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, for adjusting the binding conditions for binding nucleic acids, v. binding the nucleic acids to a carrier material, preferably containing silica, glass fibre, polyalkylenes, e.g. PP, PE/PP, PE, wherein the carrier material is used in particle form, as non-woven fabric, as fibres, as gel matrix or as membrane, preferably as column packing material, wherein the particles are preferably in the form of beads, preferably as magnetic particles, and preferably as magnetic beads; further suitable embodiments of carrier materials are described both above and below, vi. optionally washing the bound nucleic acids with one or more formulation(s), which serve as washing reagent, preferably comprising at least one branched or unbranched alcohol with one to five carbon atoms, and optionally in addition a chaotropic compound, and/or optionally a detergent from the group of non-ionic surfactants, vii. optionally eluting with one or more formulation(s), which serve as elution reagent, preferably comprising at least one complexing agent in a buffered medium.

If the composition of sample material and reagent according to the invention contains proteins and/or contaminating sample constituents, which might disturb the subsequent nucleic acid isolation and/or purification, optionally a degradation of the proteins and/or other contaminating constituents of the sample can occur in step i. (referred to as lysis hereinafter, regardless of whether the sample material contains cells or not). The composition of sample material and reagent according to the invention can be used mixed or unmixed for this step, wherein the degradation is carried out for example by adding one or more enzymes, for example with proteolytic enzymes such as lysozyme and/or a protease, and preferably with proteinase K. Optionally the degradation can be supported by adding denaturing compounds, for example a chaotropic reagent, to the reaction mixture, wherein preferably there is no branched or unbranched alkanol in the resultant lysis reaction mixture. Generally this also results in a further digestion of the sample. Therefore the performance of step i. is preferred.

A formulation that preferably serves for adjusting and/or for predefining the binding conditions for binding nucleic acids to a carrier material, is added in step ii. to the composition of the lysis reaction mixture of sample material and reagent according to the invention, or of sample material, reagent according to the invention and protein degrading enzyme, or of sample material, reagent according to the invention, protein degrading enzyme and chaotropic agent containing reagent. This formulation comprises at least one chaotropic compound and/or at least one detergent from the group of non-ionic detergents, preferably selected from the group of polyoxyethylene-fatty alcohol ethers. The molecules of this group comprise a fatty alcohol moiety that has 6 to 22 carbon atoms, and a polyoxyethylene moiety that contains 2 to 150 ($CH_2CH_2O$) units. The formulation can either be used as mixture of all the components, which is preferred, or the individual components can be added successively in any order or in the form of premixes of any combination. The formulations also usually support the degradation of the proteins and/or the further digestion of the sample. Corresponding lysis reagents can generally be used advantageously within the scope of the method according to the invention as lysis reagents (for example in the sub-step c.1) explained above).

A composition of the sample material, the reagent according to the invention, a proteolytic enzyme and optionally a chaotropic reagent, as well as a formulation that comprises a chaotropic compound and/or at least one detergent for adjusting and/or for predefining the binding conditions, can also be obtained by adding together the individual constituents in variable order or by adding mixtures of two or more constituents:

a) 1.) a proteolytic enzyme, 2.) a formulation (preferably according to ii.), which comprises a chaotropic compound and/or a detergent preferably for adjusting and/or for predefining the binding conditions, are added to the mixed or unmixed composition of sample material and reagent according to the invention, b) 1.) a proteolytic enzyme, 2.) a chaotropic reagent, 3.) a formulation (preferably according to ii.), which comprises a chaotropic compound and/or a detergent preferably for adjusting and/or for predefining the binding conditions, are added to the mixed or unmixed composition of sample material and reagent according to the invention,
c) 1.) a chaotropic reagent, 2.) a proteolytic enzyme, 3.) a formulation (preferably according to ii.), which comprises a chaotropic compound and/or a detergent preferably for adjusting and/or for predefining the binding conditions, are added to the mixed or unmixed composition of sample material and reagent according to the invention,
d) 1.) a mixture of a proteolytic enzyme and a chaotropic reagent, 2.) a formulation (preferably according to ii.), which comprises a chaotropic compound and/or a detergent preferably for adjusting and/or for predefining the binding conditions, are added to the mixed or unmixed composition of sample material and reagent according to the invention, and/or
e) a mixture of a proteolytic enzyme, optionally a chaotropic reagent, and a formulation (preferably according to ii.), which comprises a chaotropic compound and/or a detergent preferably for adjusting and/or for predefining the binding conditions, is added to the mixed or unmixed composition of sample material and reagent according to the invention.

The adding together of the individual constituents, as explained above, can for example take place in two ways: the composition of sample material and reagent according to the invention can 1. be added to the reagents used for isolation and/or purification (for example according to steps i. and ii.) or 2. can obtain these reagents by addition. The composition of sample material and reagent according to the invention can also comprise further constituents, which for example were added after the pretreatment in step (a.) but before the isolation in step (c.).

Addition of the individual formulations is optionally followed by mixing or incubation (for example according to step iii.).

According to one embodiment, for adjusting the binding conditions, another formulation according to step iv. is added to the composition obtained from the sample material, the reagent according to the invention, optionally a proteolytic enzyme, optionally a chaotropic lysis reagent, and a formulation that comprises a chaotropic compound and/or a detergent preferably for adjusting and/or for predefining the binding conditions, but which preferably does not contain a branched or unbranched alkanol. The aforesaid formulation is alkanol-containing and serves for adjusting the binding conditions for binding nucleic acids to a carrier material. According to one embodiment, the formulation comprises at least one branched or unbranched alkanol with one to five carbon atoms, and optionally additionally comprises a chaotropic compound and/or optionally a detergent from the group of non-ionic detergents. The non-ionic detergents are preferably selected from the group of polyoxyethylene-fatty alcohol ethers, which comprise a fatty alcohol moiety that has 6 to 22 carbon atoms, and comprise a polyoxyethylene moiety that contains 2 to 150 ($CH_2CH_2O$) units. Addition of the alkanol-containing formulation to the composition, which preferably still does not contain a branched or unbranched alkanol, can for example take place in two different ways: a) the alkanol-containing formulation is added to the prepared reaction mixture, b) the reaction mixture is added to the prepared alkanol-containing formulation. Corresponding alkanol-containing formulations can generally be used advantageously within the scope of the method according to the invention for adjusting the binding conditions (for example in step c.2) explained above).

Adjustment of the binding conditions is advantageously followed, in a next step, by binding to a carrier material, which preferably contains silica, glass fibres, polyalkylenes, e.g. PP, PE/PP, PE. Further suitable carrier materials that can be used in the method according to the invention have also been described above. The carrier material can be used in particle form, as non-woven fabric, as fibres, as gel matrix, as membrane and preferably as column packing material. The particles are preferably in the form of beads, and thereby preferably as magnetic particles, preferably as magnetic beads. Especially preferably, silica materials are used. It is then preferable to use magnetic particles that have a silica or glass surface. These can essentially be bead-shaped or spherical and preferably have a particle size in the range 0.02-30 µm, preferably 0.05-15 µm and especially preferably 0.1-10 µm. Magnetic silica particles, which can be used advantageously in the method according to the invention, are described e.g. in international patent application WO 01/71732, to which reference is hereby made in its entirety. Magnetic silica particles advantageously permit easy automation of the method according to the invention. Addition of the carrier material to the reaction mixture prepared for binding can for example be effected in two different ways: a) the carrier material is added to the prepared reaction mixture, b) the reaction mixture is added to the prepared carrier material.

After binding of the nucleic acids from the sample material to the carrier material occured, optionally washing (for example according to step vi.) of the bound nucleic acids is carried out in one or more step(s) with one or more formulation(s), which serve as washing reagent. Preferably these formulations comprise at least one branched or unbranched alcohol with one to five carbon atoms, and optionally additionally a chaotropic compound, and/or optionally a detergent from the group of non-ionic surfactants.

This is optionally followed (for example in step vii.) by elution of the bound and optionally washed nucleic acids with one or more formulation(s) that serve as elution reagent. Elution reagents are well-known known in the prior art. Preferably they comprise at least one complexing agent in a buffered milieu. As some methods, for example some methods based on the polymerase chain reaction, permit nucleic acid detection even if the nucleic acids are bound to the carrier material, the elution with an elution reagent can be omitted in such cases.

The especially preferred embodiment of step (c.) described above—isolation and/or purification—is based on binding the nucleic acids to a carrier material. Methods for nucleic acid isolation and/or purification that differ from this method can also be used, for example methods are also included in which the contaminants are bound to the carrier material and methods for nucleic acid isolation based on nucleic acid precipitation.

The method according to the invention for the isolation and/or purification of nucleic acids comprises, as the last procedural step (d.), an optional step for quantitative and/or qualitative detection of at least a portion of the isolated nucleic acids. For detection it is usually sufficient to detect a suitable nucleic acid segment of the isolated nucleic acid. This step is preferably carried out as quantitative detection, by a method of nucleic acid amplification, of a nucleic acid segment that is specifically to be detected. Corresponding methods of detection are sufficiently known in the prior art and require no further explanation.

According to one embodiment, at least a part of the isolated target nucleic acid is detected, wherein preferably quantitative detection takes place. The method according to the invention, according to this embodiment, suitably has an LOD (Limit of Detection) of 1 pg, preferably 0.1 pg, especially preferably 0.01 pg of target nucleic acid in the sample, from which the target nucleic acid is detected.

Owing to the pretreatment according to the invention, it is possible to isolate even such small amounts of target nucleic acids from very different sample materials efficiently, effectively and reliably and thus allow a quantitative determination of the amount of target nucleic acids in the sample being investigated. Of course, the sample can also contain much larger amounts of the target nucleic acid. The advantage of the low limit of detection of the method according to the invention is in particular that even such small amounts can be detected and therefore it can be ensured that the method leads to reliable results in the pg region (or higher), even if the sample materials differ considerably.

In the subsequent detection of the isolated target nucleic acid, the recovery rate of the isolated target nucleic acid is advantageously at least 50%, preferably at least 75%, especially preferably at least 85%.

Besides the basic steps (a.) to (d.) described above, according to the invention it is also possible to perform further steps before or after the described steps (a.) to (d.) (and for example before and after the already described partial steps of step (c.) According to one embodiment, at least one of the subsequent method steps can be carried out additionally in the method according to the invention. If the nucleic acids of the sample material to be isolated are enclosed inside cells, it is generally necessary to start with the lysis of the cells as the first procedural step, in order to release the nucleic acids and thus permit an effective pretreatment with the reagent according to the invention in step (a.). Cell lysis can be carried out by methods known in the prior art. A typical method envisages adding a chaotropic agent containing aqueous formulation and/or a protein-lysing enzyme to the sample material for degradation of the cell constituents. However, other methods can also be used for releasing the nucleic acids from the cells, including mechanical methods. According to one embodiment, lysis of cells contained in the sample material is therefore carried out. Here, the lysis is preferably carried out before adding the reagent according to the invention to the sample material and therefore before step (a.).

After cell lysis one or more subsequent purification steps can be performed in particular for removing cellular debris, before the reagent according to the invention is added in step (a.) to the correspondingly pretreated sample material comprising the released nucleic acids. Coarse separation of cell fragments can for example be effected by filtration. According to one embodiment, the sample material is cleared of cell fragments and/or molecular and/or ionic constituents of the sample material in one or more successive steps, before the reagent according to the invention is added to the sample material in step (a.).

Upon adding the reagent according to the invention to the sample material, preferably an incubation step is carried out, to ensure a proper impact of the reagent on the sample material. Preferably, the reagent was mixed with the sample material prior to incubation.

A specific application of the method according to the invention is in the purification of nucleic acids from a sample material that was obtained in the course of the biotechnological production of a product, in particular a biopharmaceutical. The purification of a biotechnological product such as in particular a biopharmaceutical requires for example, as described at the beginning, one or more successive purification steps, which are generally chromatographic steps, by which for example cell fragments, molecular and/or ionic constituents and other contaminants are separated, to obtain the biopharmaceutical in a form as pure as possible. It is in particular important to considerably reduce the residual constituents of the host organisms and/or other contaminants, for example in order to comply with the guidelines for medicinal products. For this reason, the bioprocess samples obtained in the course of the purification process and in particular the final purified biopharmaceutical are analysed for example for contaminating nucleic acids of the host cells that were used for production of the purification requires, among other things, quantitative detection of the nucleic acid contaminants that may be still contained, for example, residual amounts of host cell nucleic acids. The method according to the invention enables, for example, the effective and reliable purification of host cell nucleic acids or other nucleic acid contaminants, even if these have to be isolated from very different bioprocess samples, such as in particular various purification fractions obtained from a purification process for a biotechnological product, and/or are only present in small amounts in the sample material. According to a preferred embodiment of the method according to the invention, the reagent according to the invention is added in step (a.) to a purification fraction, before the subsequent steps (b.) (optional), (c.) and (d.) (optional) of the method according to the invention are carried out. The purification fraction can also comprise the final, purified end product.

The method according to the invention enables isolating nucleic acids such as in particular DNA and RNA from various sample materials, in which the nucleic acids are in particular present in small amounts. Suitable sample materials are mentioned in the above description, and examples are described in detail below. According to the invention, already processed sample materials can also be used as sample materials, for example samples that have been lysed, filtered and/or pretreated in some other way, in particular pre-purified samples, in which the nucleic acids that are to be purified are preferably not enclosed in cells. These processed sample materials are pretreated in step (a.) of the method according to the invention with the special reagent, so that the subsequent nucleic acid isolation and/or purification, as explained, is improved considerably especially in the case of difficult sample materials.

Preferred sample materials comprising nucleic acids to be isolated, which in most cases are present in small amounts in the sample material, comprise in particular the following groups:

The first group of suitable sample materials comprises a sample material that has an aqueous composition and is preferably a purification fraction from a purification process. The purification fraction is, according to one embodiment, an aqueous sample material, which in addition to the nucleic acid to be isolated comprises one or more buffer substances and/or salts. Examples of buffering agents often contained in purification fractions are acetate buffer, carbonate buffer, sulphate buffer, phosphate buffer, citrate buffer and glycine buffer. Biological buffering agents usually employed in purification buffers are ACES, ADA, BES, BICINE, BIS-TRIS, CHES, citrate, glycine, Gly-Gly, HEPES, HEPPS, imidazole, MES, MOPS, PIPES, phosphate, TAPS, TES, TRICINE and TRIS. Common salts that occur in particular in purification fractions are chlorides, sulphates, phosphates with metal ions of the alkali and alkaline earth group and ammonium as cation optionally also Zn, Cu, Ni, Co, Fe salts (if IMAC such as Ni-NTA was used as purification step). According to one embodiment, the sample material is a chromatographic eluate, which optionally also is provided in a further processed form. Preferably the sample material is a purification fraction obtained in the course of a purification process for a biotechnological product, such as in particular a biopharmaceutical. The sample material can accordingly contain, for example, biomolecules and/or organisms, where biomolecules means, in the sense of this application, molecules that occur in living organisms. The biomolecules and/or organisms contained in the sample material can have at least one of the following properties:
  i. the biomolecules and/or organisms are selected from the group consisting of peptides, polypeptides, proteins, nucleic acids, viruses and/or vaccines. The nucleic acids are preferably DNA, RNA, plasmids and small non-coding RNAs such as in particular small interfering RNA (siRNA),
  ii. the biomolecules and/or organisms are pharmaceutically active substances,
  iii. the biomolecules are produced synthetically or biotechnologically and/or
  iv. the biomolecules and/or organisms are biopharmaceuticals.

This group of sample materials includes in particular sample materials occurring in the field of pharmaceutical and biotechnology industry. This group comprises in particular bioprocess samples such as in particular biotechnology products and sample materials obtained in the production process, in particular purification fractions obtained in a purification process for a biotechnological product. A classical example is a purification fraction obtained from a column-chromatography purification process. Corresponding bioprocess samples occur in particular in the biotechnological production of products such as for example biopharmaceuticals. Biopharmaceuticals that are used inter alia as diagnostic aids or therapeutic agents, such as in particular therapeutic peptides, oligopeptides, polypeptides and proteins, in particular recombinantly produced growth factors, hormones, cytokines and therapeutic antibodies, to name just a few typical examples of biopharmaceuticals, are of particular interest. According to one embodiment, however, the biopharmaceuticals also include viruses, vaccines and nucleic acids, such as DNA, RNA and plasmids. Further examples are also mentioned in the preamble, and reference is hereby made to the corresponding disclosure.

Owing to the biotechnological production process, the bioprocess samples usually contain both the biotechnologically produced product, for example the biopharmaceutical, and the constituents of the used culture medium and/or of the host organism respectively of the host cells such as among other things the nucleic acids of the host, which are to be separated. Moreover, bioprocess samples may also be contaminated with other nucleic acids, for example viral nucleic acids. For example, special measures are usually applied in the purification processes in order to reduce the proportion of viral nucleic acids in the biological product. In the course of the purification process, as a rule the degree of purity of the biotechnological product in the bioprocess sample increases, and one of the objectives pursued in the purification process is to reduce the amount of contaminating nucleic acids to a minimum. Remaining nucleic acids of the host that was used for the production of the biopharmaceutical and/or other nucleic acid contaminants such as for example viral nucleic acids represent potentially dangerous contaminants in the purified end product and are therefore preferably detected quantitatively in the purified end product and/or in one or more of the bioprocess samples obtained in the course of the purification process, for example so as to be able to prove to the regulatory authorities that the permissible or recommended maximum limits of contaminating nucleic acids are not exceeded. The method according to the invention is an especially suitable method of nucleic acid isolation for this purpose, on the basis of its particular sensitivity, reliability and ease of performance.

Furthermore, this group also includes sample materials that are obtained in the area of chemical synthesis, for example samples containing siRNA molecules, which after synthesis undergo for example chromatographic purification processes, and whose subsequent quantification and concentration by means of the method according to the invention is conceivable.

According to one embodiment, the sample material, such as in particular the bioprocess sample, is essentially cell-free. According to one embodiment, the sample material is not a sample that was obtained in a nucleic acid amplification process, such as in particular a PCR process.

The second group of suitable sample materials comprising nucleic acids in small amounts that are to be isolated and/or purified comprises human or animal body constituents, selected from the group comprising body fluids, body cells and/or body tissues, preferably blood, blood constituents, serum, cerebrospinal fluid, mucosal smears, sputum, urine, stool, semen and tissue samples. These body constituents preferably contain one or more of the following molecules and/or organisms:
  i. freely circulating human or animal nucleic acids (DNA, RNA), for example freely circulating fetal nucleic acids, nucleic acids from malignant and/or non-malignant tumours, nucleic acids from apoptotic cells, small non-coding RNA such as microRNA (miRNA) and siRNA,
  ii. freely circulating nucleic acids from microorganisms, preferably from pathogens, especially preferably from protozoa, bacteria and viruses,
  iii. microorganisms, preferably pathogens, especially preferably protozoa, bacteria and viruses.

This group comprises in particular sample materials that are of interest in molecular medical diagnostics, but in particular only contain small amounts of the target nucleic acids to be detected. This includes for example the following nucleic acid-containing sample materials: blood products, such as in particular maternal blood, blood plasma or blood serum comprising short-chain freely circulating fetal nucleic acids to be isolated, blood samples comprising freely circulating tumour nucleic acid, tissue samples from apoptotic tissues comprising free nucleic acids, and tissue samples for detecting small non-coding RNA such as in particular miRNA and siRNA. Moreover, for example blood samples from infected humans or animals, for which pathogens or degradation products of pathogens, in particular of their nucleic acids, are present in the blood, are also included.

The third group of suitable sample materials comprises sample materials that are analysed in forensic nucleic acid diagnostics. These samples are preferably selected from the group of liquid and solid materials containing cells and/or nucleic acids and/or organisms. If the material to be analysed is a solid, the cells and/or nucleic acids and/or organisms contained in or on this material are extracted in a liquid, so that they can be used in the method according to the invention for nucleic acid isolation and/or purification.

This group of sample materials is characterized in particular by a potentially unlimited variety of sample materials, which comprises all materials that may carry or contain nucleic acids, but in particular often only contain small traces of nucleic acids to be detected. Hence, the method according to the invention is particularly advantageous, as it can isolate nucleic acids efficiently and effectively, which are only present at very low concentrations in the sample, wherein even very diverse compositions of the sample materials do not have an adverse impact on the method. As no special individual pretreatment of the various sample materials is necessary, the method according to the invention enables a broad, standardized, automated and simultaneous nucleic acid screening of the very diverse forensic samples. Thereby, it is also conceivable that, by means of the method according to the invention, sample materials can also be used as forensic evidence, from which, owing to a very low content of nucleic acids, sufficient amounts of nucleic acids cannot be isolated with the methods known in the prior art. Therefore a more extensive and molecular diagnostics is conceivable, that is based on a larger number and type of samples, which can lead to new and/or further results and can therefore provide an increased reliability of the forensic investigation results.

The fourth group of suitable sample materials comprises a composition with a sample component and optionally organisms. The sample component of this composition is preferably selected from the group comprising foodstuffs or constituents thereof, and constituents of the environment, preferably soil, water and vegetation, wherein it is dissolved or resuspended in the sample material. If the sample component is water, the water sample is either a constituent of the composition, or is itself the sample to be analysed. The sample materials of this group thereby comprise nucleic acid-containing samples, which are used in the area of nucleic acid analysis in food and environmental diagnostics. For example, in food production and monitoring it is important to be able to detect even slight microbial contaminations in foods on the basis of microbial nucleic acids by molecular methods. Detection of pathogens from water samples by means of a rapid method of detection on a molecular basis, instead of a classical method, such as time-consuming growing of organisms, is of great importance. This also applies to the analysis of soil and plant samples, for which analytical monitoring in terms of commensals is also of interest. Thereby, detection of nucleic acids from bacteria, viruses, fungi and/or protozoa is conceivable. Even slightly contaminated samples provide important information in particular in the area of monitoring diagnostics, so that the method according to the invention, with which small amounts of nucleic acids can be detected after digestion of the contaminating organisms, is especially suitable. The sample materials belonging to this group can also vary considerably with respect to their composition and nature, for example their pH and/or their salt content. Thus, here as well the method according to the invention is particularly advantageous, as the pretreatment according to the invention permits efficient, effective and reliable purification even of very small amounts of nucleic acids from very different samples, without requiring prior individual adaptation/adjustment of the sample material and/or of the purification process.

The biotechnologically produced products in the first group of sample materials, such as in particular biopharmaceuticals, are preferably produced by genetically modified or unmodified organisms and/or cells. Biotechnological products are produced both in prokaryotic and in eukaryotic cells. Cells of lower and higher eukaryotes are used as eukaryotic cells. These organisms and/or cells are preferably selected from the group comprising cell lines from mammals, cell lines from birds, cell lines from insects, cell lines from fishes, cell lines from plants and microorganisms, wherein the cell lines from mammals preferably comprise the following cell lines: human cell lines, cell lines from horse cells, cell lines from bovine cells, cell lines from pig cells, cell lines from kangaroo cells, cell lines from sheep cells, cell lines from monkey cells, cell lines from dog cells, cell lines from cat cells, cell lines from marten cells, cell lines from rabbit cells, rodent cell lines, cell lines from hamster cells, cell lines from rat cells and cell lines from mouse cells, and especially preferably the cell lines Hek293 (human embryonic kidney), HeLa (human cervical cancer), Vero (kidney of a normal adult African green monkey), MDCK (canine Cocker Spaniel kidney), CHO (Chinese hamster ovary cells), SP2 (mouse myeloma), NSO (mouse myeloma), hybridoma cell lines and *Saccharomyces cerevisiae*. According to one embodiment, the host cells used are immortalized cells. The microorganisms preferably comprise bacteria and yeasts, and especially preferably *Escherichia coli*. As described in the introduction, respective cells can be modified using genetic engineering technologies in order to be able to produce the product of interest. E.g. a gene encoding the product of interest such as a peptide or protein can be introduced recombinantly, e.g. using a vector. The respectively modified cell can then produce the product of interest. Furthermore, cells, in particular bacteria or yeast cells, can be used to produce a desired product from a precursor molecule using the enzymatic machinery of the cell.

According to another aspect, the present invention provides a reagent for use in a method of isolation and/or purification of nucleic acids from a sample material, in particular for preparation of the sample material, wherein the reagent comprises at least the following components:

a. at least one or more compounds comprising an amino group, selected from one or more of the following groups:
  i. polar-neutral proteinogenic α-aminocarboxylic acids, preferably asparagine, cysteine, glutamine, glycine, threonine and serine,
  ii. nonpolar-hydrophobic proteinogenic α-aminocarboxylic acids, preferably alanine, leucine, isoleucine, methionine, proline and valine,
  iii. basic α-aminocarboxylic acids, preferably arginine, lysine and ornithine,
  iv. non-proteinogenic aminocarboxylic acids, selected from the group comprising β-alanine, D-alanine, L-homoserine and D-valine,
  v. aminocarboxylic acid polymers comprising at least one of the aminocarboxylic acids mentioned in (i.) to (iv.), preferably in a size from 0.5 kDa to 300 kDa, preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine, preferably the aminocarboxylic acid polymer consists of the aminocarboxylic acids mentioned in (i.) to (iv.),
  vi. peptides from 2 to 4 aminocarboxylic acids, comprising at least one of the aminocarboxylic acids mentioned in (i.) to (iv.), wherein the aminocarboxylic acids comprised in the peptide are preferably selected from identical or different aminocarboxylic acids mentioned in (i.) to (iv.), preferably glycine dimers, glycine trimers and glycine tetramers, and preferably the peptide consists of the aminocarboxylic acids mentioned in (i.) to (iv.), vii. a compound of the general formula $R^3R^4N-CR^1R^2-COOH$ (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, wherein the alkyl component has a chain length from C1 to C5, is branched or unbranched, is saturated or unsaturated, and wherein at least one of $R^1$, $R^2$, $R^3$ and $R^4$ is not hydrogen. One, two, three, four or five hydroxyl groups can be present in the hydroxyalkyl group. Di(hydroxyalkyl) groups and tri(hydroxyalkyl) groups are also suitable. The compound of general formula (I) is preferably selected from the group N-(tri(hydroxymethyl)methyl)glycine (tricine) and N,N-bis(2-hydroxyethyl)glycine (bicine), viii. a compound of general formula $R^3R^4N-CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated. One, two, three, four or five hydroxyl groups can be present in the hydroxyalkyl group. Di(hydroxyalkyl) groups and tri(hydroxyalkyl) groups are also suitable. Compound (II) is preferably Tris(hydroxymethyl)-aminomethane (Tris), and at least one or more of the following components:

b. at least one detergent or mixtures of detergents, preferably selected from the group of non-ionic surfactants comprising alkylglucosides and/or polyoxyethylene-alkylphenyl ethers, c. at least one complexing agent or mixtures of complexing agents, d. at least one protein or mixtures of proteins, preferably the protein is a globular protein that is preferably selected from the group of albumins and/or globulins, wherein, if the reagent contains one or more components of groups (i.), (ii.), (iii.) and/or (vi.), the reagent comprises additionally at least one protein or mixtures of proteins, wherein the protein is preferably a globular protein, preferably selected from the group of albumins and/or globulins.

Thus, the reagent according to the invention is accordingly suitable in various embodiments for preparing the sample for subsequent nucleic acid isolation and/or purification. The pretreatment with the reagent permits effective and even quantitative isolation of nucleic acids from very different sample materials, even if the sample material only contains very small amounts of the nucleic acids. For some sample materials, nucleic acid purification only becomes possible when performing the pretreatment with the reagent according to the invention, as is also shown in the examples.

In a special embodiment of the reagent according to the invention, which contains the compound Tris(hydroxymethyl)-aminomethane (Tris), the formulation does not contain EDTA and/or EGTA.

The reagent contains at least one compound comprising an amino group, but can also contain several of the respective compounds. If two or more compounds comprising an amino group are present, preferably mixtures of the components within and/or between the groups (i.) to (viii.) are present.

For example, one or more polar-neutral proteinogenic α-aminocarboxylic acids such as asparagine and/or cysteine and/or glutamine and/or glycine and/or threonine and/or serine can be comprised. Moreover, one or more nonpolar-hydrophobic proteinogenic α-aminocarboxylic acids, such as for example alanine and/or leucine and/or isoleucine and/or methionine and/or proline and/or valine can also be comprised in the reagent, as well as one or more basic α-aminocarboxylic acids such as for example arginine and/or lysine and/or ornithine. One or more non-proteinogenic aminocarboxylic acids, for example β-alanine and/or D-alanine and/or L-homoserine and/or D-valine can also be comprised. Aminocarboxylic acid polymers may preferably be formed from identical, or two or more different aminocarboxylic acid monomers from the group of polar-neutral proteinogenic α-aminocarboxylic acids and/or the group of nonpolar-hydrophobic proteinogenic α-aminocarboxylic acids and/or the group of basic α-aminocarboxylic acids and/or the group of non-proteinogenic aminocarboxylic acids can also be comprised in the reagent. Peptides from 2 to 4 aminocarboxylic acids, preferably selected from identical or different aminocarboxylic acids from the group of polar-neutral proteinogenic α-aminocarboxylic acids and/or the group of basic α-aminocarboxylic acids and/or the group of nonpolar-hydrophobic proteinogenic α-aminocarboxylic acids and/or the group of non-proteinogenic aminocarboxylic acids can also be comprised in the reagent. Moreover, one or more compounds of the general formula $R^2R^4N-CR^1R^2-COOH$ (I) can also be comprised in the reagent, wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl and hydroxyalkyl, wherein the alkyl component has a chain length from C1 to C5, is branched or unbranched, is saturated or unsaturated, and wherein at least one of the residues of $R^1$, $R^2$, $R^3$ and $R^4$ is not hydrogen. One, two, three, four or five hydroxyl groups can be present in the hydroxyalkyl group. Di(hydroxyalkyl) groups and tri(hydroxyalkyl) groups are also suitable. The compound of general formula (I) is preferably selected from the group N-(tri(hydroxymethyl)methyl)glycine (tricine) and/or N,N-bis(2-hydroxyethyl)glycine (bicine). Moreover, one or more compounds of general formula $R^2R^4N-CR^5R^6R^7$ (II) can also be comprised in the reagent, wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of the residues of $R^5$, $R^6$ and $R^7$ is a hydroxyalkyl, and wherein the alkyl component has a chain length from C1 to C5, is branched or unbranched, and is saturated or unsaturated. One, two, three, four or five hydroxyl groups can be present in the hydroxyalkyl group. Di(hydroxyalkyl) groups and tri(hydroxyalkyl) groups are also suitable. A preferred compound corresponding to this formula is the compound Tris(hydroxymethyl)-aminomethane (Tris). Examples of suitable saturated or unsaturated, branched or unbranched alkyl components have been described above in connection with the reagent. These should apply here analogously.

The reagent according to the invention contains, beside one or more of the described compounds comprising an amino group, at least one or more of the following components: at least one detergent and/or at least one complexing agent and/or at least one protein, preferably a globular protein, wherein each of the components can be present in the form of a pure compound or as a mixture of several compounds, i.e. in the form of a mixture of detergents and/or mixture of complexing agents and/or mixture of proteins. As described above, these additional components have a positive influence on the pretreatment, because they increase the recovery rate of the nucleic acid to be purified. Reference is made to the above disclosure.

The pH of the reagent is preferably in the range from pH 3 to pH 9.

In embodiments of the reagent, additionally at least one protein or mixtures of proteins is/are contained, if the reagent contains one or more components of groups (i.), (ii.), (iii.) and/or (vi.). That is, if the reagent contains for example one or more polar-neutral proteinogenic α-aminocarboxylic acids such as for example asparagine and/or cysteine and/or glutamine and/or glycine and/or threonine and/or serine, and/or one or more nonpolar-hydrophobic proteinogenic α-aminocarboxylic acids, for example alanine and/or leucine and/or isoleucine and/or methionine and/or proline and/or valine, and/or one or more basic α-aminocarboxylic acids such as for example arginine and/or lysine and/or ornithine, and/or peptides from 2 to 4 aminocarboxylic acids, preferably selected from identical or different aminocarboxylic acids from the group of polar-neutral proteinogenic α-aminocarboxylic acids (i.) and/or the group of nonpolar-hydrophobic proteinogenic α-aminocarboxylic acids (ii.) and/or the group of basic α-aminocarboxylic acids (iii.) and/or the group of non-proteinogenic aminocarboxylic acids (iv.) such as for example β-alanine and/or D-alanine and/or L-homoserine and/or D-valine. The protein comprised in the reagent is preferably a globular protein, which is preferably selected from the group of albumins and/or globulins.

The addition of a protein to the reagent according to the invention, which for the pretreatment of the sample material is contacted with the sample material, surprisingly proved advantageous. This increased the efficiency of nucleic acid purification, especially if the sample material only had a low concentration of protein. The use of a corresponding protein in the reagent according to the invention therefore improves nucleic acid purification, especially if the sample materials to be processed only comprise small amounts of protein and/or have differences with respect to the comprised protein concentration.

Embodiments that contain the components Tris and/or bicine and/or tricine, according to one embodiment of the reagent according to the invention do not contain a chaotropic compound in the formulation. The advantages of this embodiment have already been explained in connection with the use of a corresponding reagent in the method according to the invention; reference is made to the above disclosure.

According to one embodiment, the reagent according to the invention contains one or more aminocarboxylic acid polymers in a size of 0.5 kDa to 300 kDa. The aminocarboxylic acid polymers can be present as homopolymers from identical aminocarboxylic acid monomers or as copolymers from two or more different aminocarboxylic acid monomers, wherein the monomers are arranged alternating, randomly distributed, in gradients or block form in the polymer chain. Both polymer types are preferably formed from aminocarboxylic acid monomers from the groups (i.) polar-neutral proteinogenic α-aminocarboxylic acids and/or (ii.) nonpolar-hydrophobic proteinogenic α-aminocarboxylic acids and/or (iii.) basic α-aminocarboxylic acids and/or (iv.) non-proteinogenic aminocarboxylic acids, preferably in conjunction with hydrohalides such as for example hydrobromide or hydrochloride. Compounds that are preferably selected are poly-L-lysine, poly-L-lysine hydrobromide, poly-L-lysine hydrochloride, poly(L-glutamine, L-alanine), poly(L-glutamine, L-lysine) hydrobromide, poly-L-ornithine. Polymers that are formed from non-proteinogenic enantiomeric forms are also included, for example poly-D-lysine, poly-D-lysine hydrobromide, poly(D-glutamine, D-lysine) hydrobromide.

If an embodiment of the reagent according to the invention contains peptides from 2 to 4 aminocarboxylic acids, these are preferably selected from identical or different aminocarboxylic acids of groups (i.) polar-neutral proteinogenic α-aminocarboxylic acids and/or (ii.) nonpolar-hydrophobic proteinogenic α-aminocarboxylic acids and/or (iii.) basic α-aminocarboxylic acids and/or (iv.) non-proteinogenic aminocarboxylic acids. Peptide compounds are preferred between the preferably stated molecules asparagine, cysteine, glutamine, glycine, threonine, serine, alanine, leucine, isoleucine, methionine, proline, valine, arginine, lysine, ornithine, β-alanine, D-alanine, L-homoserine and D-valine, wherein any combination of these molecules as dimer, trimer or tetramer is possible. Suitable examples of peptide compounds from 2 aminocarboxylic acids have already been presented in connection with the use of the reagent according to the invention within the scope of the method according to the invention. Reference is made to the above disclosure. Analogously to the described peptide compounds, which are combined from 2 aminocarboxylic acids, peptide compounds with 3 to 4 aminocarboxylic acids are possible.

Preferably the peptides from 2 to 4 aminocarboxylic acids are the glycine-glycine dimer, and preferably the glycine-glycine-glycine trimer and preferably the glycine-glycine-glycine-glycine tetramer.

The total concentration of the compound comprising an amino group and/or combinations of various of these compounds in the reagent is, according to one embodiment, 5 mM to 500 mM, preferably 25 mM to 350 mM, especially preferably 50 mM to 250 mM.

One embodiment of the reagent according to the invention with detergent contains a detergent or mixtures of detergents, which are preferably selected from the group of non-ionic surfactants, preferably selected from the group of alkylglucosides and/or polyoxyethylene-alkylphenyl ethers. The alkylglucoside is preferably selected from the group of polysorbates, preferably from polysorbate 20, polysorbate 40 and polysorbate 80, and is especially preferably polysorbate 20 (Tween 20). The group of polyoxyethylene-alkylphenyl ethers preferably comprises octoxynol 9 (Triton X-100) and Nonidet P-40.

According to one embodiment, the total concentration of the detergent, preferably of the non-ionic surfactant or the non-ionic surfactants, in the reagent is 0.1% (v/v) to 5% (v/v), preferably 0.2% (v/v) to 4% (v/v), and preferably 0.5% (v/v) to 3% (v/v) and also preferably 1% (v/v) to 3% (v/v). Values of 0.2% (v/v) to 0.5% (v/v) have proved especially advantageous for the use of polyoxyethylene-alkylphenyl ethers, for example Triton X-100. According to one embodiment, concentrations at a level of approx. 1% (v/v) to 5% (v/v) are used when using alkylglucosides, such as in particular polysorbates such as for example Tween 20. Preferably at least two detergents are used, wherein one detergent is preferably selected from the group of polyoxyethylene-alkylphenyl ethers and the other detergent is selected from the group of alkylglucosides, for example the polysorbates. Especially preferably the reagent according to the invention contains a combination of Triton X-100 and Tween 20.

According to one embodiment, the reagent according to the invention contains a complexing agent or mixtures of complexing agents, selected from the group comprising ethylenediamine tetraacetic acid (EDTA), ethylene glycol-bis(aminoethylether)-N,N'-tetraacetic acid (EGTA) and/or ethylenediamine disuccinic acid (EDDS). Especially preferably, EDTA is used. In this embodiment with complexing agent, the total concentration of the complexing agent(s) in the reagent is preferably 10 mM to 500 mM, preferably 10 mM to 300 mM, 10 mM to 200 mM and more preferably 10 mM to 100 mM. In a special embodiment of the reagent according to the invention, which contains the compound Tris(hydroxymethyl)-aminomethane (Tris), however, the formulation does not contain EDTA and/or EGTA.

According to one embodiment, the reagent according to the invention contains a protein or mixtures of proteins. According to one embodiment, the protein does not have any enzymatic activity, preferably the protein is not an enzyme. Preferably, the protein is a globular protein, preferably selected from the group of albumins and/or globulins. The albumins are preferably selected from animal, plant, and/or human albumin, preferably bovine serum albumin (BSA). The globulins are preferably selected from animal, plant, and/or human globulin, preferably γ-globulin. The total concentration of the protein or proteins in the reagent is preferably 1 mg/mL to 100 mg/mL, preferably 2 mg/ml to 25 mg/ml, preferably 2 mg/ml to 10 mg/ml and preferably 4 mg/mL to 10 mg/mL. For the use of IgG and BSA, it is advantageous to use 2 mg/ml to 25 mg/ml, preferably 2 mg/ml to 10 mg/ml and preferably 4 mg/mL to 10 mg/mL. These concentrations are advantageous especially if using globular proteins, such as in particular IgG and/or BSA.

The reagent according to the invention preferably does not contain aqueous formulations, which contain phosphate and/or citrate in an overall concentration 5 mM, as these can have an inhibitory effect on the nucleic acid isolation and/or purification.

According to one embodiment, the reagent according to the invention comprises at least one or more compounds comprising an amino group, selected from one or more of the following groups i. to viii:
 i. asparagine, cysteine, glutamine, glycine, threonine and serine,
 ii. alanine, leucine, isoleucine, methionine, proline and valine,
 iii. arginine, lysine and ornithine,
 iv. β-alanine, D-alanine, L-homoserine and D-valine,
 v. poly-L-lysine, poly-L-lysine hydrobromide, poly-L-lysine hydrochloride, poly(L-glutamine, L-alanine), poly(L-glutamine, L-lysine) hydrobromide, poly-L-ornithine,
 vi. glycine dimers, glycine trimers, glycine tetramers and the dipeptide (Ala-Glu),
 vii. N-(tri(hydroxymethyl)methyl)glycine (tricine) and N,N-bis(2-hydroxyethyl)glycine (bicine),
 and/or
 viii. Tris(hydroxymethyl)-aminomethane (Tris),
wherein, if the reagent contains one or more compounds of groups (i.), (ii.), (iii.) and/or (vi.), additionally at least one protein or mixtures of proteins is/are contained in the reagent, wherein the protein is preferably a globular protein, which preferably is selected from the group of albumins and/or globulins.

Especially preferred embodiments of the reagent according to the invention are described below. The individual components of the reagent are present in these preferred embodiments preferably in the concentrations stated above for the individual constituents, in this respect reference is made to the above disclosure.

According to a preferred embodiment the reagent according to the invention comprises at least glycine, Gly-Gly, tricine and/or bicine as compound comprising an amino group, at least one complexing agent, preferably EDTA, and at least one, preferably at least two detergents, preferably Triton X-100 and/or Tween 20.

Advantageously, the reagent comprises additionally at least one protein, preferably a globular protein such as IgG or BSA.

In another preferred embodiment, the reagent according to the invention comprises one or more polar-neutral and/or basic α-aminocarboxylic acids from the group asparagine, glutamine, arginine, lysine and ornithine. The addition of corresponding α-aminocarboxylic acids also has a positive effect in the pretreatment of the sample material, especially if these α-aminocarboxylic acids are combined with a buffer, in particular a Tris or sulphonic acid buffer, for example a HEPES or HEPPS buffer. Moreover, the reagent preferably comprises at least one protein, preferably a globular protein such as IgG or BSA.

According to another preferred embodiment the reagent according to the invention comprises the aminocarboxylic acid compounds glutamine, proline, poly-L-lysine and/or poly(L-glutamine, L-alanine) and the dipeptide (Ala-Glu). Preferably it also comprises a complexing agent, for example EGTA, and at least one, preferably at least two detergents, especially preferably a polyoxyethylene-alkylphenyl ether such as Nonidet-P 40 and/or a polysorbate such as preferably Tween 20. The reagent also comprises a globular protein, preferably IgG, and preferably one or more buffers, preferably one or two sulphonic acid buffers, for example HEPES and/or HEPPS.

In another preferred embodiment, the reagent according to the invention comprises at least one, preferably both of the aminocarboxylic acid compounds β-alanine and poly(L-glutamine, L-alanine). Preferably it also comprises a complexing agent, for example EDTA, and at least one, preferably at least two detergents, especially preferably a polyoxyethylene-alkylphenyl ether such as Triton X-100 and/or a polysorbate such as preferably polysorbate 40. Preferably the reagent also comprises a globular protein, preferably IgG and one or more buffers, preferably one or two sulphonic acid buffers, for example HEPES and/or HEPPS.

In another preferred embodiment, the reagent according to the invention comprises at least two, preferably all of the aminocarboxylic acid compounds cysteine, alanine, arginine, poly-L-lysine hydrobromide and tris(hydroxymethyl)-aminomethane (Tris). Moreover, this reagent comprises a globular protein, in particular an IgG, if one or more of the aminocarboxylic acid compounds cysteine, alanine and/or arginine are contained in the reagent.

In another preferred embodiment, the reagent according to the invention comprises at least two, preferably all of the aminocarboxylic acid compounds serine, methionine, lysine, D-valine and poly-L-ornithine. Preferably it also comprises a complexing agent, for example EGTA, and at least one, preferably at least two detergents, especially preferably a polyoxyethylene-alkylphenyl ether such as Triton X-100 and/or a polysorbate such as preferably Tween 20. The reagent also comprises a globular protein, preferably BSA, if one or more of the aminocarboxylic acid compounds serine, methionine and/or lysine are contained in the reagent.

In another preferred embodiment, the reagent according to the invention comprises at least two, preferably all of the aminocarboxylic acid compounds threonine, leucine and ornithine. Preferably it also comprises a complexing agent, for example EDDS, and at least one, preferably at least two detergents, especially preferably a polyoxyethylene-alkyl-phenyl ether such as Triton X-100 and/or a polysorbate such as preferably Tween 20. The reagent comprises additionally at least one protein, preferably a globular protein such as IgG or BSA, and preferably one or more buffers, preferably one or two sulphonic acid buffers, for example HEPES and/or HEPPS.

According to one embodiment, the reagent according to the invention does not have any lysing properties and therefore cannot lyse the sample material with which it is brought in contact for preparation.

The use of the reagent according to the invention for the pretreatment of sample materials for nucleic acid purification enables to isolate and/or purify nucleic acids from various sample materials, even if they are only present wherein in small amounts. Furthermore, the pretreatment of the sample material with the reagent according to the invention enables to purify nucleic acids from sample materials, from which it is not possible, without the use of the reagent according to the invention, to isolate nucleic acids using conventional standard methods, as used for example in the present examples. The nucleic acids that are to be purified can be selected from the group of single-stranded and double-stranded eukaryotic, prokaryotic and viral nucleic acids, comprising RNA, DNA and plasmids. According to one embodiment, the nucleic acids that are to be purified represent at least partially a contamination of the sample material.

Furthermore, the present invention provides a method for isolating a target nucleic acid from a bioprocess sample, which preferably comprises at least one biopharmaceutical, wherein the method comprises at least the following steps:

a. pretreatment of the bioprocess sample with a reagent, wherein the reagent comprises at least one or more compounds comprising an amino group, selected from one or more of the following groups:
  i. polar-neutral proteinogenic α-aminocarboxylic acids, preferably asparagine, cysteine, glutamine, glycine, threonine and serine,
  ii. nonpolar-hydrophobic proteinogenic α-aminocarboxylic acids, preferably alanine, leucine, isoleucine, methionine, proline and valine,
  iii. basic α-aminocarboxylic acids, preferably, arginine, lysine and ornithine,
  iv. non-proteinogenic aminocarboxylic acids, selected from the group comprising β-alanine, D-alanine, L-homoserine and D-valine,
  v. aminocarboxylic acid polymers comprising at least one of the aminocarboxylic acids mentioned in (i.) to (iv.), preferably consisting of the aminocarboxylic acids stated in (i) to (iv), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine, preferably in a size from 0.5 kDa to 300 kDa,
  vi. peptides from 2 to 4 aminocarboxylic acids, comprising at least one of the aminocarboxylic acids stated in (i) to (iv), preferably consisting of the aminocarboxylic acids stated in (i) to (iv), preferably selected from identical or different aminocarboxylic acids mentioned in (i.) to (iv.), preferably glycine dimers, glycine trimers and glycine tetramers,
  vii. a compound of the general formula $R^3R^4N-CR^1R^2-COOH$ (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, wherein the alkyl component has a chain length from C1 to C5, is branched or unbranched, is saturated or unsaturated, and wherein at least one of $R^1$, $R^2$, $R^3$ and $R^4$ is not hydrogen. One, two, three, four or five hydroxyl groups can be present in the hydroxyalkyl group. Di(hydroxyalkyl) groups and tri(hydroxyalkyl) groups are also suitable. The compound of general formula (I) is preferably selected from the group N-(tri(hydroxymethyl)methyl)glycine (tricine) and N,N-bis(2-hydroxyethyl)glycine (bicine),
  viii. a compound of the general formula $R^3R^4N-CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated. One, two, three, four or five hydroxyl groups can be present in the hydroxyalkyl group. Di(hydroxyalkyl) groups and tri(hydroxyalkyl) groups are also suitable. Compound (II) is preferably Tris(hydroxymethyl)-aminomethane (Tris),
b. preferably mixing of the reagent with the bioprocess sample,
c. isolation and/or purification of nucleic acids from the bioprocess sample, which has been contacted with and/or mixed with the reagent,
d. optionally quantitative and/or qualitative detection of at least a portion of the isolated target nucleic acids, preferably quantitative detection by amplification of a nucleic acid segment that is to be detected.

The pretreatment of the bioprocess sample with the reagent defined in step (a.) has, as already mentioned in connection with the first method according to the invention, the advantage that the subsequent nucleic acid purification can be improved considerably, especially if the bioprocess sample only contains small amounts of target nucleic acid. For some bioprocess samples, isolation of the nucleic acids only becomes possible as a result of this. The pretreatment carried out in step (a.) enables, in a surprisingly simple manner, the reliable isolation of nucleic acids even from very different bioprocess samples with an essentially constant efficiency, i.e. within tolerable variations. Thus, with the method according to the invention, it is possible to isolate target nucleic acids (for example host DNA or other nucleic acid contaminants), even if they are present in an amount of only 1 pg or less in the bioprocess sample. Even amounts of 0.1 pg or even 0.01 pg can be purified effectively due to the pretreatment according to the invention. Therefore the method according to the invention is sufficiently sensitive to enable, even in this demanding field of use of bioprocess samples, a reliable isolation and even quantitative isolation of the target nucleic acids with a uniform method of isolation. The method can therefore also be automated easily, which is a considerable advantage in this area, where often large numbers of samples must be processed.

The method according to the invention for isolating a target nucleic acid from a bioprocess sample is essentially a special embodiment of the first method according to the invention, already described in detail above, for the isolation and/or purification of nucleic acids from a sample material. Especially suitable and preferred compounds comprising an amino group, which can be comprised in the reagent used in step (a.), as well as suitable and preferred concentrations of the individual components of the reagent used for the pretreatment were therefore already explained in detail above in connection with the first method according to the invention and also apply to the method for isolating a target nucleic acid from a bioprocess sample. To avoid repetitions, reference is therefore made to the above disclosure in its entirety, which is also applicable here. However, for the sake of completeness, especially preferred embodiments are once again explained in detail below. Especially preferably, the reagent according to the invention described in detail above is used for the pretreatment in step (a.), and is also described in more detail in the claims.

Suitable and preferred compounds comprising an amino group were described in detail above; reference is made to the corresponding disclosure. The total concentration of the compound comprising an amino group and/or combinations of various of these compounds, in the reaction mixture of bioprocess sample and the reagent used in step (a.) for the pretreatment is, according to one embodiment, 2.5 mM to 400 mM, preferably 12.5 mM to 280 mM, especially preferably 25 mM to 200 mM. These concentrations have proved to be particularly advantageous for reaction mixtures of sample material and reagent ranging in size from 200 µl to 1000 µl. Here, a quantitative isolation of the nucleic acids was possible, even if the reaction mixture of reagent according to the invention and sample material only contained small amounts of nucleic acids in the order of only 1 pg of nucleic acid. The reagent used according to the invention in step (a.) preferably has a total concentration of the compound comprising an amino group and/or combinations of various of these compounds of 5 mM to 500 mM, preferably 25 mM to 350 mM, especially preferably 50 mM to 250 mM.

According to a preferred embodiment of the method according to the invention for isolating nucleic acids from a bioprocess sample, the pretreatment in step (a.) is carried out with a reagent that also comprising at least one or more of the following components:
at least one detergent or mixtures of detergents,
at least one complexing agent or mixtures of complexing agents, preferably selected from the group comprising ethylenediamine tetraacetic acid (EDTA), ethylene glycol-bis(aminoethylether)-N,N'-tetraacetic acid (EGTA) and/or ethylenediamine disuccinic acid (EDDS), especially preferably EDTA
and/or
at least one protein or mixtures of proteins.

Experiments have shown that a pretreatment with a corresponding reagent, which additionally contains one or more of the corresponding components, can further improve the subsequent isolation and/or purification. If the reagent comprises several components or ingredients, they can be added in the form of a homogeneous reagent, i.e. a solution, or alternatively the reagent can be formed by mixing two or more compositions, which for example are brought in contact with the bioprocess sample either together or optionally also separately from one another, to carry out the pretreatment of the sample according to step (a.). The separate addition of the individual components is according to the invention also covered by the term pretreatment of the bioprocess sample with a reagent. Preferably a homogeneous reagent is used.

The detergent is, as described above, preferably a non-ionic surfactant, preferably an alkylglucoside and/or polyoxyethylene-alkylphenyl ether. The group of alkylglucosides comprises in particular the group of polysorbates, preferably polysorbate 20, polysorbate 40 and polysorbate 80. Especially preferably, polysorbate 20 (Tween 20) is used as alkylglucoside. The polyoxyethylene-alkylphenyl ether is preferably octoxynol 9 (Triton X-100) or Nonidet P-40. Preferably the total concentration of the detergent or the mixture of detergents, in particular of the non-ionic surfactant or the non-ionic surfactants in the reagent is 0.1% (v/v) to 5% (v/v), preferably 0.2% (v/v) to 4% (v/v), and preferably 0.5% (v/v) to 3% (v/v) and preferably as well as 1% (v/v) to 3% (v/v). 0.2% (v/v) to 0.5% (v/v) is preferred for the use of polyoxyethylene-alkylphenyl ethers such as for example Triton X-100 and preferably 1% (v/v) to 5% (v/v) for the use of alkylglucosides, in particular of polysorbates such as for example Tween 20.

The total concentration of the detergent or the mixture of detergents comprised in the reagent, in particular of the non-ionic surfactant or the non-ionic surfactants in the reaction mixture of bioprocess sample and reagent according to the invention is according to one embodiment 0.05% (v/v) to 4% (v/v), preferably 0.1% (v/v) to 3% (v/v), and preferably 0.25% (v/v) to 2.5% (v/v), and preferably as well as 0.5% (v/v) to 2.5% (v/v). Values from 0.1% (v/v) to 0.4% (v/v) have proved especially advantageous for the use of polyoxyethylene-alkylphenyl ethers, for example Triton X-100. According to one embodiment the concentration is preferably 0.5% (v/v) to 4% (v/v). This concentration is in particular advantageous for the use of polysorbates, for example Tween 20. Preferably the reagent used in step (a.) for the pretreatment of the bioprocess sample comprises at least two detergents. According to one embodiment, one detergent is selected from the group of alkylglucosides, preferably the polysorbates, especially preferably polysorbate 20 and the other detergent is selected from the group of polyoxyethylene-alkylphenyl ethers and is preferably Triton X-100.

According to one embodiment, the reagent used in step (a.) for the pretreatment comprises a complexing agent or mixtures of complexing agents. According to one embodiment, the total concentration of the complexing agent(s) in the reagent is 10 mM to 500 mM, preferably 10 mM to 100 mM. According to one embodiment, in the reaction mixture of bioprocess sample and reagent according to the invention, the total concentration of the complexing agent(s) contained in the reagent is 5 mM to 400 mM, preferably 5 mM to 80 mM. The advantages have already been explained above.

According to one embodiment of the method according to the invention, the reagent used in step (a.) for the pretreatment comprises at least one protein, preferably a globular protein or mixtures of globular proteins.

According to one embodiment, the protein does not have any enzymatic activity. Preferably it is not an enzyme. The globular protein is preferably selected from the group of albumins and/or globulins. According to one embodiment of the method according to the invention, the total concentration of the protein or proteins in the reagent used in step (a.) is 1 mg/mL to 100 mg/mL, preferably 2 mg/mL to 25 mg/mL, 2 mg/mL to 10 mg/mL and also preferably 4 mg/mL to 10 mg/mL. Concentrations of 2 mg/mL to 25 mg/mL, 2 mg/ml to 10 mg/ml and preferably 4 mg/ml to 10 mg/ml are especially suitable for globular proteins, such as in particular IgG and BSA. According to one embodiment, the total concentration of the protein or proteins from the reagent in the reaction mixture of bioprocess sample and reagent according to the invention is 0.5 mg/mL to 80 mg/mL, 1 mg/mL to 20 mg/mL, preferably 1 mg/mL to 8 mg/mL, preferably 2 mg/mL to 8 mg/mL. For details and advantages, reference is made to the above disclosure in connection with the method according to the invention.

According to one embodiment, the reagent used in step (a.) does not contain phosphate and/or citrate at an overall concentration of ≥5 mM.

According to one embodiment, the reagent used in step (a.) contains no or only small amounts of chaotropic compounds. This embodiment is advantageous, because tests have shown that chaotropic compounds such as for example chaotropic salts in the reagent used in step (a). for pretreatment, especially at higher concentrations, can have an adverse effect on the subsequent nucleic acid purification, which may for example be reflected in a lower recovery rate in the quantitative detection of the isolated target nucleic acids. Therefore the reagent used in step (a.) for the pretreatment preferably does not contain chaotropic compounds in concentrations that make the pretreatment according to the invention less effective and in particular in concentrations that disturb the subsequent isolation of the nucleic acids. Preferably the reagent used in step (a.) of the method according to the invention does not contain chaotropic salts, in particular not guanidinium salts in concentrations of more than 7M, 6M, 5M, 4M, 3M, 2M, 1M or more than 0.5M. Preferably the amount of chaotropic salts, in particular guanidinium salts, is below 0.1M. Especially preferably the reagent used in step (a.) does not contain any chaotropic salts or other chaotropic compounds. Preferably, this applies correspondingly to the pretreatment in step (a.) as such, i.e. in step (a.) preferably no chaotropic compounds are added to the bioprocess sample.

According to one embodiment, the reagent used in step (a.) for the pretreatment does not have any lysing properties.

According to one embodiment, the reagent used in step (a.) for the pretreatment comprises at least one or more compounds comprising an amino group, selected from one or more of the following groups i. to viii:
  i. asparagine, cysteine, glutamine, glycine, threonine and serine,
  ii. alanine, leucine, isoleucine, methionine, proline and valine,
  iii. arginine, lysine and ornithine,
  iv. β-alanine, D-alanine, L-homoserine and D-valine,
  v. poly-L-lysine, poly-L-lysine hydrobromide, poly-L-lysine hydrochloride, poly(L-glutamine, L-alanine), poly(L-glutamine, L-lysine) hydrobromide, poly-L-ornithine,
  vi. glycine dimers, glycine trimers, glycine tetramers and the dipeptide (Ala-Glu),
  vii. N-(tri(hydroxymethyl)methyl)glycine (tricine) and N,N-bis(2-hydroxyethyl)glycine (bicine),
  and/or
  viii. Tris(hydroxymethyl)-aminomethane (Tris).

Especially preferred embodiments of the reagent used in step (a.) are described below. In these preferred embodiments, the individual components of the reagent are preferably present in the concentrations described above for the individual constituents; in this respect reference is made to the above disclosure. As already described, the individual constituents of the reagent can also be added separately in the pretreatment of the sample material, wherein, however, addition in a homogeneous reagent, i.e. a solution, is preferred.

According to a preferred embodiment, the reagent used in step (a.) comprises at least glycine, Gly-Gly, tricine and/or bicine as compound comprising an amino group, at least one complexing agent, preferably EDTA, and at least one, preferably at least two detergents, especially preferably a polyoxyethylene-alkylphenyl ether such as Triton X-100 and/or a polysorbate such as preferably Tween 20. Especially preferably the reagent comprises additionally at least one protein, preferably a globular protein such as IgG or BSA.

According to another preferred embodiment the reagent according to the invention used in step (a.) comprises one or more polar-neutral and/or basic α-aminocarboxylic acids from the group asparagine, glutamine, arginine, lysine and ornithine. Here, experiments have shown that a pretreatment with a corresponding reagent can further improve the isolation and/or purification, especially if said α-aminocarboxylic acid(s) is/are combined with a buffer, such as in particular a Tris or sulphonic acid buffer, for example a HEPES or HEPPS buffer. Moreover, the reagent preferably comprises at least one protein, preferably a globular protein such as IgG or BSA.

According to another preferred embodiment, the reagent used in step (a.) comprises the aminocarboxylic acid compounds glutamine, proline, poly-L-lysine and/or poly(L-glutamine, L-alanine) and the dipeptide (Ala-Glu). Preferably it also comprises a complexing agent, for example EGTA, and at least one, preferably at least two detergents, especially preferably a polyoxyethylene-alkylphenyl ether such as Nonidet-P 40 and/or a polysorbate such as preferably Tween 20. Preferably the reagent also comprises a globular protein, preferably IgG and one or more buffers, preferably one or two sulphonic acid buffers, for example HEPES and/or HEPPS.

According to another preferred embodiment the reagent used in step (a.) comprises at least one, preferably both of the aminocarboxylic acid compounds β-alanine and poly(L-glutamine, L-alanine). Preferably it also comprises a complexing agent, for example EDTA, and at least one, preferably at least two detergents, especially preferably a polyoxyethylene-alkylphenyl ether such as Triton X-100 and/or a polysorbate such as preferably polysorbate 40. Preferably the reagent also comprises a globular protein, preferably IgG and as well one or more buffers, preferably one or two sulphonic acid buffers, for example HEPES and/or HEPPS.

According to another preferred embodiment the reagent used in step (a.) comprises at least two, preferably all of the aminocarboxylic acid compounds cysteine, alanine, arginine, poly-L-lysine hydrobromide and Tris(hydroxymethyl)-aminomethane (Tris). Moreover, this reagent preferably comprises a globular protein, in particular an IgG.

According to another preferred embodiment the reagent used in step (a.) comprises at least two, preferably all of the aminocarboxylic acid compounds serine, methionine, lysine, D-valine and poly-L-ornithine. Preferably it also comprises a complexing agent, for example EGTA, and at least one, preferably at least two detergents, especially preferably a polyoxyethylene-alkylphenyl ether such as Triton X-100 and/or a polysorbate such as preferably Tween 20. Preferably the reagent also comprises a globular protein, preferably BSA.

According to another preferred embodiment the reagent used in step (a.) comprises at least two, preferably all of the aminocarboxylic acid compounds threonine, leucine and ornithine. Preferably it also comprises a complexing agent, for example EDDS, and at least one, preferably at least two detergents, especially preferably a polyoxyethylene-alkyl-phenyl ether such as Triton X-100 and/or a polysorbate such as preferably Tween 20. Preferably, the reagent comprises additionally a protein, preferably a globular protein such as IgG or BSA, and preferably also one or more buffers, preferably one or two sulphonic acid buffers, for example HEPES and/or HEPPS.

According to a preferred embodiment the pH of the reagent used in step (a.) is in the range from pH 3 to pH 9.

Preferably an amount of 50 to 3000 µl, preferably 100 to 1500 µl, especially preferably 200 to 1000 µl of the particular bioprocess sample is used for the nucleic acid isolation according to the invention and is treated correspondingly in step (a.) with the reagent according to the invention. Reagent and bioprocess sample are preferably added together in step (a.) in the following ratio: 1+4 ($V_{reagent}+V_{bioprocess\ sample}$) to 4+1 ($V_{reagent}+V_{bioprocess\ sample}$) preferably 1+2 ($V_{reagent}+V_{bioprocess\ sample}$) to 2+1 ($V_{reagent}+V_{bioprocess\ sample}$) and especially preferably 1+1 ($V_{reagent}+V_{bioprocess\ sample}$). A subsequent mixing step should preferably be carried out.

The pretreatment according to the invention in step (a.) and optionally step (b.) is then followed by procedural step (c.) of isolation and/or purification of the nucleic acids. Optionally, the composition of reagent according to the invention and bioprocess sample resulting from step (a.) or step (a.) and (b.) can be further processed and/or treated before step (c.), for example by adding further formulations or by separating individual constituents. The composition of bioprocess sample and reagent according to the invention may therefore also comprise further constituents, which for example were added after the pretreatment in step (a.) but before the isolation in step (c.) or also fewer. For simplicity, compositions that result from corresponding intermediate steps are also designated, within the context of the present application, as compositions of reagent according to the invention and bioprocess sample resulting from step (a.) or step (a.) and (b.).

Step (c.), which depending on the embodiment may comprise several sub-steps, functions basically with any kind of method of isolation for nucleic acids. Non-exhaustive examples of methods of isolation with and without the use of carrier materials for binding the nucleic acids were already described above in connection with the first method according to the invention. Reference is made to the above disclosure. According to one embodiment, the isolation and/or purification of the nucleic acids in step (c.) comprises at least one of the following sub-steps c.1) and c.2), preferably both sub-steps:

c.1) Digestion of the composition of the reagent according to the invention and bioprocess sample that results from step (a). or step (a.) and (b.) by adding at least one lysis reagent. This treatment with a lysis reagent serves in particular for the denaturation and/or degradation of any proteins that might be contained in the bioprocess sample and of any other contaminating sample constituents that might be present. Moreover—depending on the bioprocess sample—this step may also serve the purpose of releasing the nucleic acids contained in the bioprocess sample, from for example complexing substances. As the method according to the invention advantageously enables the isolation of target nucleic acids from very different bioprocess samples, which may correspondingly differ with respect to their composition, treatment with a lysis reagent is advantageous, even if the target nucleic acids in the bioprocess sample are generally not contained inside cells. In this digestion step, preferably classical lysis reagents are used, for example proteolytic enzymes, preferably proteases such as proteinase K, chaotropic compounds such as preferably chaotropic salts and/or detergents, preferably non-ionic detergents. According to one embodiment, more than one lysis reagent is used in this digestion step. Thus, the bioprocess sample pretreated with the reagent in step (a.) may be treated with at least one proteolytic enzyme, preferably proteinase K, and at least one lysis reagent, which comprises at least one chaotropic compound and/or detergent. Chaotropic salts such as in particular guanidinium salts are preferably used as chaotropic compound. Non-ionic detergents are preferably used as detergent. As detergent, it is preferable to use a polyoxyethylene-fatty alcohol ether, which comprises a fatty alcohol moiety, which preferably has 6 to 22 carbon atoms and comprises a polyoxyethylene moiety which preferably has to 150 ($CH_2CH_2O$) units. Lysis reagents that can preferably be used in this digestion step are also described for example in WO 2009/144182, to which reference is hereby made. According to one embodiment, the bioprocess sample pretreated according to step (a.) is brought in contact and incubated, in the digestion step, with at least one proteolytic enzyme and at least one further lysis reagent, preferably containing a chaotropic compound. The duration of the incubation step is preferably at least 3 min, preferably at least 5 min, preferably at least 10 min, especially preferably at least 15 min and is preferably carried out at temperatures at which the proteolytic enzyme has increased activity. Preferably the incubation step is carried out at at least 35° C., at least 40° C., at least 50° C., at least 55° C. or at least 60° C. Preferably the incubation is carried out in a temperature range from 35° C. to 70° C., preferably 40° C. to 65° C. Especially preferably, a combination of a proteolytic enzyme and a chaotropic agent containing lysis reagent is used, which preferably also comprises one of the aforementioned detergents.

c.2) Isolation of the nucleic acids, preferably by binding to a carrier material. If the bioprocess sample also contains other nucleic acids in addition to the target nucleic acid, these can also be purified simultaneously. If desired, however, selective purification of the target nucleic acids can also take place. The carrier material is preferably a nucleic acid-binding solid phase from the group of silica-containing materials, silica gel, silicon dioxide, glass, zeolite, aluminium oxide, titanium dioxide, zirconium dioxide, kaolin, silica gel, ceramic, polymeric carrier materials such as for example polyalkylenes and polystyrene beads. What is finally decisive is that the carrier material is able to bind nucleic acids. The carrier material can be modified with functional groups such as for example anion exchanger groups, or alternatively can be unmodified and therefore does not bear any additional functional groups on the surface. Further embodiments of the carrier material have already been described above, and reference is made to the corresponding disclosure. Especially preferably, silica materials are used. In this case it is preferable to use magnetic particles that have a silica or glass surface. Magnetic silica particles advantageously permit easy automation of the method according to the invention, and preferred embodiments have already been described above in connection with the first method according to the invention; reference is made to the corresponding disclosure. The binding conditions necessary for binding the nucleic acids can, according to one embodiment, be adjusted by the lysis reagent used in step c.1), for example if it contains a suitable concentration of a chaotropic compound. A corresponding binding step has been described in the prior art, for example in U.S. Pat. No.

5,234,809. Preferably, however, for adjusting the binding conditions, a binding reagent is added comprising at least one alcohol, preferably a branched or unbranched alkanol with 1 to 5 carbon atoms, especially preferably isopropanol. The binding reagent can also comprise a chaotropic compound, preferably a chaotropic salt and/or at least one detergent. The detergent is preferably a non-ionic detergent. Preferred embodiments of the binding reagent were also described above in connection with the first method according to the invention. Reference is made to the corresponding disclosure. Other binding reagents that can be used in step c.2) are described for example in WO 2009/144182, to which reference is hereby made. Binding of the nucleic acids to the carrier material is preferably followed by separation of the bound nucleic acids from the remaining sample. This is preferably carried out by separating the nucleic acids bound to the carrier material—if using magnetic silica particles, usually with the aid of a magnetic field. Optionally the nucleic acids can then be washed and eluted.

The method according to the invention for isolating a target nucleic acid from a bioprocess sample further comprises an optional step (d.) for detecting at least a portion of the isolated target nucleic acids. Detection may be qualitative, but in the area of biopharmaceuticals it is preferably quantitative. For detection, it is usually sufficient to detect a nucleic acid segment of the isolated target nucleic acid. Quantitative detection preferably takes place by amplification of a segment of the target nucleic acid. Quantitative detection allows to make a quantitative statement about the amount of target nucleic acid contained in the bioprocess sample. This is important in particular in the area of biopharmaceuticals due to the regulatory requirements, as specific amounts of for example host DNA or other nucleic acid contaminants must not be exceeded.

Besides the basic steps (a.) to (d.) already described above, according to the invention further steps can also be carried out before or after said steps (a.) to (d.) (and for example before and after the described sub-steps of step (c.)). Details were also explained in connection with the first method according to the invention; reference is made to the corresponding disclosure.

The term bioprocess sample relates in particular to a sample material that was obtained or produced in the course of a biotechnological production process.

According to one embodiment, the bioprocess sample is a purification fraction obtained in a purification process. For example, it can be a purification fraction that was obtained in the course of a purification process for a biotechnologically produced product (in particular a biopharmaceutical). The methods usually employed here for purifying correspondingly produced biotechnological products were explained above; reference is made to the corresponding disclosure. The terms bioprocess sample and purification fraction also comprise the finally purified and/or formulated biotechnological product (for example the biopharmaceutical). According to one embodiment, the purification fraction is a chromatographic eluate. The eluate for example might be obtained in the course of an ion exchange chromatography, protein-A/G-affinity chromatography, hydrophobic-interaction chromatography and/or hydrophilic-interaction chromatography. The purification fraction is according to one embodiment an aqueous sample material, which comprises one or more buffer substances and/or salts in addition to the target nucleic acid to be isolated. Examples of buffer substances often contained in corresponding purification fractions are acetate buffer, carbonate buffer, sulphate buffer, phosphate buffer, citrate buffer and glycine buffer. Other buffering agents often used in purification buffers and therefore contained in purification fractions are ACES, ADA, BES, BICINE, BIS-TRIS, CHES, citrate, glycine, Gly-Gly, HEPES, HEPPS, imidazole, MES, MOPS, PIPES, phosphate, TAPS, TES, TRICINE, TRIS. Maleate, malonate, formate, trimethylamine, triethylamine are also used. Common salts, which also occur in particular in purification fractions, are for example chlorides, sulphates, phosphates of the alkali and alkaline-earth group and ammonium compounds, optionally also Zn, Cu, Ni, Co, Fe salts for example if an IMAC method such as Ni-NTA was used for purification.

The bioprocess sample and in particular the purification fraction are according to one embodiment essentially cell-free. The purification fraction to be investigated can originate from any stage of a purification process for a biotechnologically produced product. According to one embodiment, the target nucleic acids are isolated with the method according to the invention from different purification fractions obtained from a purification process. Thus, the target nucleic acid can for example be purified with the method according to the invention from various or even each purification fraction of the purification process, including the finally purified end product. This makes it possible, advantageously allows, to monitor the course of purification and for example to ensure that the amount of target nucleic acid contained in the purified end product does not exceed the desired and/or permissible amount. Based on the pretreatment of the bioprocess sample carried out in step (a.) according to the invention, the actual isolation of the nucleic acids can be effected with a uniform method, even if the bioprocess samples such as for example the various purification fractions differ with respect to their composition. Furthermore, a quantitative isolation of even very small amounts of nucleic acids is possible.

According to one embodiment, the target nucleic acid represents a contamination of the bioprocess sample, for example of the purification fraction. The nucleic acid representing a contamination can for example be a viral nucleic acid or the nucleic acid of a microorganism. According to one embodiment, the target nucleic acid is a DNA, such as in particular a genomic DNA, from a host or host cell used for the production of a biotechnological product such as in particular a biopharmaceutical. Hosts and host cells usually employed as producers were explained above in connection with the first method according to the invention. Reference is made to the corresponding disclosure. Especially when using immortalized host cells, the DNA from the host cell should not be present in greater amounts in a finally produced biopharmaceutical. Respective immortalized host cells are often used when recombinantly producing a biopharmaceutical of interest such as in particular a biopharmaceutical peptide or protein. As mentioned above, the regulatory authorities require proof that certain limits are not exceeded. Furthermore, the nucleic acid isolation methods used for providing this proof have to fulfil certain criteria, in particular they must be sufficiently sensitive and reliable, in order to guarantee a reliable result. These requirements are met by the method according to the invention. The corresponding background, further examples of bioprocess samples as well as suitable and preferred examples of biopharmaceuticals have already been explained in detail in the preamble and in connection with the first method according to the invention. Reference is made to the above disclosure, which is also relevant here. According to one embodiment, the biopharmaceutical is not a nucleic acid. According to one embodiment, the biopharmaceutical is a peptide or protein. As described above, peptides and proteins can be produced recombinantly using various host cells.

According to one embodiment, at least a portion of the isolated target nucleic acid is detected, and the detection is preferably quantitative. As already mentioned, this has the advantage that it is possible to determine whether the amount of target nucleic acids in the analysed bioprocess sample is above or below the permissible and/or desired maximum limit.

According to one embodiment, the method according to the invention has an LOD (Limit Of Detection) of 1 pg, 0.5 pg preferably 0.1 pg, 0.05 pg especially preferably 0.01 pg of target nucleic acid in the bioprocess sample, from which the target nucleic acid is isolated. Owing to the pretreatment according to the invention, it is possible to isolate even such small amounts of target nucleic acids from very different bioprocess samples efficiently, effectively and reliably and thus allow a quantitative determination of the amount of target nucleic acids in the bioprocess sample. Of course, the bioprocess sample may, however, also contain a considerably higher amount of the target nucleic acid. A particular advantage of the low limit of detection of the method according to the invention is that even such small amounts can be detected and it is thereby also ensured that the method leads to reliable results in the pg region (or higher), even if the bioprocess samples differ considerably and the purification is thus considerably impeded. On the basis of its low LOD, the method according to the invention meets the official requirements on the sensitivity of a nucleic acid purification method used for the detection of nucleic acid contaminants.

In the optional subsequent detection of the isolated target nucleic acid, the recovery rate of the isolated target nucleic acid is at least 50%, preferably at least 75%, especially preferably at least 85%.

According to a special embodiment, the present invention provides a method for detecting at least one target nucleic acid in various bioprocess samples obtained from a purification process, wherein the method is characterized in that the target nucleic acid is isolated from the bioprocess samples to be investigated according to the method described above for isolating a target nucleic acid from a bioprocess sample and at least a portion of the purified target nucleic acid is detected. Preferably the detection is quantitatively, for example by means of known amplification techniques. For details of the method for isolating a target nucleic acid from a bioprocess sample, reference is made to the above disclosure. This variant of the method has the advantage that the target nucleic acid can be isolated by the method according to the invention from various bioprocess samples that were obtained in the course of a purification process, preferably including the finally purified end product. This allows, as described above, to monitor the course of purification and for example to ensure that the purified end product does not exceed the desired and/or permissible amount of target nucleic acids. The target nucleic acid is preferably a host DNA, especially if the host cells are immortalized cells and/or a viral nucleic acid. Suitable examples of embodiments for the bioprocess samples, the biopharmaceuticals and the individual process steps were explained above in detail. Reference is made to the corresponding disclosure.

The present invention further relates to the use of a reagent for preparing a bioprocess sample preferably containing a biopharmaceutical for subsequent nucleic acid isolation and/or purification and preferably detection of the nucleic acid, wherein the reagent comprises at least the following components:

a. at least one or more compounds comprising an amino group, from one or more of the following groups:
  i. polar-neutral proteinogenic α-aminocarboxylic acids, preferably asparagine, cysteine, glutamine, glycine, threonine and serine,
  ii. nonpolar-hydrophobic proteinogenic α-aminocarboxylic acids, preferably alanine, leucine, isoleucine, methionine, proline and valine,
  iii. basic α-aminocarboxylic acids, preferably arginine, lysine and ornithine,
  iv. non-proteinogenic aminocarboxylic acids, selected from the group comprising β-alanine, D-alanine, L-homoserine and D-valine,
  v. aminocarboxylic acid polymers comprising at least one of the aminocarboxylic acids mentioned in (i.) to (iv.), preferably consisting of the aminocarboxylic acids mentioned in (i.) to (iv.), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine, preferably in a size from 0.5 kDa to 300 kDa,
  vi. peptides from 2 to 4 aminocarboxylic acids, comprising at least one of the aminocarboxylic acids mentioned in (i.) to (iv.), preferably consisting of the aminocarboxylic acids mentioned in (i.) to (iv.), preferably selected from identical or different aminocarboxylic acids mentioned in (i.) to (iv.), preferably glycine dimers, glycine trimers and glycine tetramers,
  vii. a compound of the general formula $R^2R^4N-CR^1R^2-COOH$ (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, wherein the alkyl component has a chain length from C1 to C5, is branched or unbranched, is saturated or unsaturated, and wherein at least one of $R^1$, $R^2$, $R^3$ and $R^4$ is not hydrogen. One, two, three, four or five hydroxyl groups can be present in the hydroxyalkyl group. Di(hydroxyalkyl) groups and tri(hydroxyalkyl) groups are also suitable. The compound of general formula (I) is preferably selected from the group N-(tri(hydroxymethyl)methyl)glycine (tricine) and N,N-bis(2-hydroxyethyl)glycine (bicine),
  viii. a compound of the general formula $R^3R^4N-CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated. One, two, three, four or five hydroxyl groups can be present in the hydroxyalkyl group. Di(hydroxyalkyl) groups and tri(hydroxyalkyl) groups are also suitable. Compound (II) is preferably Tris(hydroxymethyl)-5 aminomethane (Tris), and preferably at least one or more of the following components:
b. at least one detergent,
c. at least one complexing agent,
d. at least one protein.

The use of the reagent for pretreatment advantageously has the effect that the efficiency of nucleic acid purification can be increased and therefore even very small amounts of target nucleic acids can be isolated from a bioprocess sample preferably containing a biopharmaceutical. In case of some bioprocess samples, nucleic acid purification only becomes possible as a result of using the reagent according to the invention. Isolation is preferably followed by detection of the target nucleic acid. Here, the use according to the invention results in that the recovery rate of the target nucleic acid can be increased and it is therefore at least 50%, preferably at least 75%, especially preferably at least 85%.

For preferred embodiments of the individual constituents of the reagent including suitable and preferred concentrations of the individual constituents as well as combinations of constituents and preferred embodiments of the reagent according to the invention, reference is made to the above disclosure of the reagent, in particular of the reagent that has been described in the first method according to the invention for the isolation and/or purification of nucleic acids from a sample material, and of the reagent according to the invention. The bioprocess sample is preferably a purification fraction, preferably a purification fraction obtained from a chromatographic process. The bioprocess sample is preferably an aqueous sample material, which in addition to the nucleic acid to be isolated, comprises one or more buffering agents and/or salts. Further details on the composition and properties of the bioprocess sample and the preferred embodiment, the purification fraction, were explained above in connection with the method according to the invention for purification of nucleic acids from bioprocess samples. Reference is made to the above disclosure.

Moreover, the use of the reagent according to the invention and/or of the method according to the invention allows a quantitative detection of the isolated and purified nucleic acids, which preferably are contained in a purification fraction from a purification process. As a result of the pretreatment according to the invention, the LOD can be lowered advantageously. The use according to the invention enables to lower the limit of detection of nucleic acid isolation to at least 1 pg, preferably at least 0.1 pg and especially preferably 0.01 pg of nucleic acids in the sample. Even such small amounts of nucleic acids can be isolated, due to the pretreatment according to the invention. Of course, purification of larger amounts of nucleic acids is also possible and is covered by each aspect of the invention. Furthermore, the pretreatment according to the invention allows to purify and to detect the nucleic acids with a recovery rate of at least 50%, preferably at least 75%, especially preferably at least 85%. These amazingly low limits of detection and high recovery rates increase the reliability of nucleic acid purification, because they ensure that even minute amounts (and so of course also larger amounts) of nucleic acids can be purified reliably from bioprocess samples. This is of great importance, especially in connection with medicinal product authorization/approval procedures for biopharmaceuticals, to increase safety for the patient and exclude contaminations by small amounts of nucleic acids.

The kit according to the invention for use in the method for isolation and/or purification of nucleic acids from sample material comprises an embodiment of the reagent according to the invention corresponding to the above description of the reagent for use within the method of isolation and purification of nucleic acids and/or corresponding to the above description of the method according to the invention for the isolation and/or purification of nucleic acids. The kit comprises at least one or more of the following components:

i. a carrier material, preferably containing silica, glass fibre, polyalkylenes, e.g. PP, PE/PP, PE, for separating the target nucleic acids. The carrier material can be used in particle form, as non-woven fabric, as fibres, as gel matrix, as membrane, preferably as column packing, wherein the particles are preferably in the form of beads. The beads are preferably in the form of magnetic particles, preferably magnetic beads, ii. one or more formulations that serve as lysis reagent, preferably comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, iii. one or more enzymes, preferably proteinase K, DNase and/or RNase, iv. one or more formulations that serve as binding reagent, preferably comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, and optionally at least one branched or unbranched alcohol with one to five carbon atoms, v. one or more formulations that serve as washing reagent, preferably comprising at least one branched or unbranched alcohol with one to five carbon atoms, and optionally a chaotropic compound, and/or optionally a detergent from the group of non-ionic surfactants, vi. one or more formulations that serve as elution reagent, preferably comprising at least one complexing agent in a buffered milieu.

The kit is suitable both for manual uses, and for automated applications, in particular carrier materials based on membranes and/or columns as well as magnetic beads enable an automation practicable.

The term "reagent" refers within the context of the present application in particular to a chemical composition. The terms reagent, composition and formulation are used here as synonyms, unless some other meaning follows from the context in which they are used. Preferably the reagent is an aqueous composition.

The terms "nucleic acid" and "nucleic acids" and terms derived therefrom are used synonymously in the singular or plural form within the context of the present application. Nucleic acids that can be isolated with the present method are for example DNA, RNA, mRNA, plasmids, cosmids, mitochondrial, epigenetically modified, single-stranded, double-stranded, circular, freely circulating, fetal, artificial or synthetic nucleic acids, as well as cDNA and fragments thereof. According to one embodiment, the nucleic acids that are to be purified represent a contamination of the sample material, such as in particular of a bioprocess sample. Examples of corresponding contaminants in the case of bioprocess samples are in particular genomic DNA of the producer or viral nucleic acids. Depending on the performance of step (c.) of the methods according to the invention, both total nucleic acids, and specifically RNA or DNA may be purified. Moreover, short-chain nucleic acids (for example DNA and RNA of any form, including non-coding RNA such as for example miRNA or synthetic nucleic acids with a length of ≤1000 bp, ≤800 bp, ≤500 bp, ≤300 bp ≤200 bp or ≤100 bp) can be purified on setting suitable binding conditions. Corresponding conditions/methods for isolating short-chain nucleic acids are well known in the prior art and may be used correspondingly according to the invention in step (c.) of the methods according to the invention.

Particularly preferred embodiments are again described in the following:

According to a first embodiment, a method of isolation and/or purification of nucleic acids from sample material is provided, which comprises the following steps:

a. adding a reagent to the sample material, wherein the reagent comprises at least one or more compounds comprising an amino group, selected from one or more of the following groups:
  i. polar-neutral proteinogenic α-aminocarboxylic acids, preferably asparagine, cysteine, glutamine, glycine, threonine and serine,
  ii. nonpolar-hydrophobic proteinogenic α-aminocarboxylic acids, preferably alanine, leucine, isoleucine, methionine, proline and valine,
  iii. basic α-aminocarboxylic acids, preferably arginine, lysine and ornithine,
  iv. non-proteinogenic aminocarboxylic acids, selected from the group comprising β-alanine, D-alanine, L-homoserine and D-valine,
  v. aminocarboxylic acid polymers comprising at least one of the aminocarboxylic acids mentioned in (i.) to (iv.), preferably consisting of the aminocarboxylic acids mentioned in (i.) to (iv.), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine,
  vi. peptides from 2 to 4 aminocarboxylic acids, comprising at least one of the aminocarboxylic acids mentioned in (i.) to (iv.), preferably consisting of the aminocarboxylic acids mentioned in (i.) to (iv.), preferably selected from identical or different aminocarboxylic acids mentioned in (i.) to (iv.), preferably glycine dimers, glycine trimers and glycine tetramers,
  vii. a compound of the general formula $R^3R^4N—CR^1R^2—COOH$ (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, di(hydroxyalkyl) and tri(hydroxyalkyl), wherein the alkyl component has a chain length from C1 to C5, is branched or unbranched, is saturated or unsaturated, and wherein at least one of $R^1$, $R^2$, $R^3$ and $R^4$ is not hydrogen, preferably selected from the group N-(tri(hydroxymethyl)methyl)glycine (tricine) and N,N-bis(2-hydroxyethyl)glycine (bicine),
  viii. a compound of the general formula $R^3R^4N—CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated, wherein the compound is preferably Tris(hydroxymethyl)-aminomethane (Tris),
b. preferably mixing this reagent with the sample material,
c. isolating and/or purifying nucleic acids from the sample material, which has been contacted with and/or mixed with the reagent,
d. optionally quantitative and/or qualitative detection of at least a portion of the isolated nucleic acids, preferably quantitative detection by amplification of a nucleic acid segment to be detected, wherein the method comprises at least one of the following features:
  I. the reagent that according to (a.) is added to the sample material does not contain a chaotropic agent, or
  II. if in step (c.) at least one chaotropic agent containing reagent is added, the addition of a chaotropic agent containing reagent in step (c.) occurs for the first time in the absence of a branched or unbranched alkanol with 1 to 5 carbon atoms, wherein the sample material with the nucleic acids to be isolated and/or purified is selected from one of the following groups:

A. an aqueous composition, preferably a purification fraction from a purification process, comprising biomolecules and/or organisms, wherein the biomolecules and/or organisms have at least one of the following features:
  i. the biomolecules and/or organisms are selected from the group consisting of proteins, nucleic acids (preferably DNA, RNA, plasmids, small interfering RNA (siRNA)), viruses and/or vaccines,
  ii. the biomolecules and/or organisms are pharmaceutically active substances,
  iii. the biomolecules are produced synthetically or biotechnologically, and/or
  iv. the biomolecules are biotechnologically produced molecules that are produced by genetically modified or unmodified organisms,
B. human or animal body constituents selected from the group comprising body fluids, body cells and/or body tissue, preferably blood, blood constituents, serum, cerebrospinal fluid, liquor mucosal smears, sputum, urine, stool, semen and tissue samples, wherein these body constituents comprise one or more of the following molecules and/or organisms:
  i. freely circulating human or animal nucleic acids, preferably freely circulating fetal nucleic acids, nucleic acids from malignant and/or non-malignant tumours, nucleic acids from apoptotic cells, small non-coding RNA, microRNA (miRNA) and siRNA,
  ii. freely circulating nucleic acids from microorganisms, preferably from pathogens, especially preferably from bacteria and viruses, and/or
  iii. microorganisms, preferably pathogens, especially preferably bacteria and viruses,
C. forensic sample materials containing cells and/or nucleic acids and/or organisms, wherein the cells and/or nucleic acids and/or organisms are present in a liquid sample material or are present extracted from the sample material in a liquid,
and/or
D. a composition comprising a sample component and optionally organisms, wherein the sample component is selected from the group comprising foodstuffs or constituents thereof, and constituents of the environment, preferably soil, water and vegetation, and optionally is resuspended.

The method according to the first embodiment, is in a second embodiment characterized in that step c. isolation and/or purification comprises at least the following sub-steps:
  i. optionally degrading proteins and/or contaminating sample constituents by adding one or more enzymes, preferably proteinase K, optionally in combination with a chaotropic agent containing reagent, in the absence of a branched or unbranched alkanol, to the composition of sample material and reagent resulting from (a.), or (a.) and (b.) according to the first embodiment,
  ii. adding a formulation comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, preferably for adjusting or predefining the binding conditions for binding nucleic acids,
  iii. optionally mixing and/or incubating,
  iv. adding
      a formulation comprising at least one branched or unbranched alkanol with one to five carbon atoms, optionally additionally a chaotropic compound and/or optionally a detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units,
      for adjusting the binding conditions for binding nucleic acids,
  v. binding the nucleic acids to a carrier material, preferably containing silica, glass fibre or polyalkylenes, e.g. PP, PE/PP, PE, wherein the carrier material is used in particle form, as non-woven fabric, as fibres, as gel matrix or as membrane, preferably as column packing material, wherein the particles are preferably in the form of beads, preferably as magnetic particles, and preferably as magnetic beads,
  vi. optionally washing the bound nucleic acids with one or more formulation(s), which serve as washing reagent, preferably comprising at least one branched or unbranched alcohol with one to five carbon atoms, and optionally additionally a chaotropic compound, and/or optionally a detergent from the group of non-ionic surfactants,
  vii. optionally eluting with one or more formulation(s) that serve as elution reagent, preferably comprising at least one complexing agent in a buffered milieu,
wherein the formulations of steps i. and ii. according to this second embodiment or mixtures of i. and ii. according to this second embodiment can be added in variable order to the composition of sample material and reagent resulting from (a.), or (a.) and (b.) according to the first embodiment.

The method according to the first or second embodiment is in a third embodiment preferably characterized in that additionally to the aforementioned steps, at least one further step of the following steps takes place:
  i. carrying out lysis of cells that are contained in the sample material, wherein lysis is carried out before adding the reagent to the sample material according to step (a.) from the first embodiment,
  ii. purifying the sample material to remove cell fragments and/or molecular and/or ionic constituents of the sample material in one or more successive steps before adding the reagent to the sample material according to step (a.) from the first embodiment, wherein these steps preferably comprise chromatographic techniques, and/or
  iii. incubating the composition of sample material and reagent resulting from process claim (a.) according to the first embodiment, and preferably the composition of sample material and reagent after mixing resulting from process claim (a.) and (b.) according to the first embodiment.

Said method according to one or more of the first, second and third embodiment is in a fourth embodiment characterized in that the biotechnologically produced biomolecules are produced by genetically modified or unmodified organisms, preferably selected from the group comprising cell lines of mammals, cell lines of birds, cell lines of insects, cell lines of fishes, cell lines of plants and cloned microorganisms, wherein the cell lines of mammals preferably comprise the following cell lines: human cell lines, cell lines from horse cells, cell lines from bovine cells, cell lines from pig cells, cell lines from kangaroo cells, cell lines from sheep cells, cell lines from monkey cells, cell lines from dog cells, cell lines from cat cells, cell lines from marten cells, cell lines from rabbit cells, cell lines from hamster cells, cell lines from rat cells and cell lines from mouse cells, and especially preferably the cell lines Hek293 (human embryonic kidney), HeLa (human cervical cancer), Vero (kidney of a normal adult African green monkey), MDCK (canine Cocker Spaniel kidney), CHO (Chinese hamster ovary cells), SP2 (mouse myeloma), NSO (mouse myeloma) and *Saccharomyces cerevisiae*.

The method according to one or more of the embodiments one to four is in a fifth embodiment characterized in that the reagent used for the pretreatment also comprises at least one or more of the following components:
  at least one detergent or mixtures of detergents, preferably selected from the group of non-ionic surfactants comprising alkylglucosides and/or polyoxyethylene-alkylphenyl ethers,
  at least one complexing agent or mixtures of complexing agents,
  and/or
  at least one protein or mixtures of proteins, wherein the protein is preferably a globular protein, preferably selected from the group of albumins and/or globulins.

According to a sixth embodiment a reagent is provided for use in a method for isolation and/or purification of nucleic acids from a sample material, in particular for preparation of the sample material, which comprises the following components:
  a. at least one or more compounds comprising an amino group, selected from one or more of the following groups:
    i. polar-neutral proteinogenic α-aminocarboxylic acids, preferably asparagine, cysteine, glutamine, glycine, threonine and serine,
    ii. nonpolar-hydrophobic proteinogenic α-aminocarboxylic acids, preferably alanine, leucine, isoleucine, methionine, proline and valine,
    iii. basic α-aminocarboxylic acids, preferably arginine, lysine and ornithine,
    iv. non-proteinogenic aminocarboxylic acids, selected from the group comprising β-alanine, D-alanine, L-homoserine and D-valine,
    v. aminocarboxylic acid polymers comprising at least one of the aminocarboxylic acids mentioned in (i.) to (iv.), preferably consisting of the aminocarboxylic acids mentioned in (i.) to (iv.), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine, vi. peptides from 2 to 4 aminocarboxylic acids, comprising at least one of the aminocarboxylic acids mentioned in (i.) to (iv.), preferably consisting of the aminocarboxylic acids mentioned in (i.) to (iv.), preferably selected from identical or different aminocarboxylic acids mentioned in (i.) to (iv.), preferably glycine dimers, glycine trimers and glycine tetramers, vii. a compound of the general formula $R^3R^4N$—$CR^1R^2$—COOH (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, di(hydroxyalkyl) and tri(hydroxyalkyl), wherein the alkyl component has a chain length from C1 to C5, is branched or unbranched, is saturated or unsaturated, and wherein at least one of $R^1$, $R^2$, $R^3$ and $R^4$ is not hydrogen, preferably selected from the group N-(tri(hydroxymethyl)methyl)glycine (tricine) and N,N-bis(2-hydroxyethyl)glycine (bicine), viii. a compound of the general formula $R^3R^4N$—$CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated, wherein the compound is preferably Tris(hydroxymethyl)-aminomethane (Tris), and at least one or more of the following components:

b. at least one detergent or mixtures of detergents, preferably selected from the group of non-ionic surfactants comprising alkylglucosides and/or polyoxyethylene-alkylphenyl ethers, c. at least one complexing agent or mixtures of complexing agents, d. at least one protein or mixtures of proteins, wherein the protein is preferably a globular protein, preferably selected from the group of albumins and/or globulins, wherein, if the reagent comprises one or more components of groups (i.), (ii.), (iii.) and/or (vi.), additionally at least one protein or mixtures of proteins is/are comprised in the reagent, wherein the protein is preferably a globular protein, preferably selected from the group of albumins and/or globulins, wherein the reagent is not a mixture consisting of Tris and EDTA or Tris and EGTA, and wherein, if the component (a.) is Tris, bicine or tricine, the reagent does not comprise a chaotropic compound.

The method and/or reagent according to the fifth or sixth embodiment is preferably characterized in that the detergent is selected from one or more of the following groups:

a. alkylglucosides, preferably from the group of polysorbates, preferably selected from polysorbate 20, polysorbate 40 and polysorbate 80, especially preferably the detergent is polysorbate 20 (Tween 20), b. polyoxyethylene-alkylphenyl ethers, preferably octoxynol 9 (Triton X-100) and Nonidet P-40.

The method and/or reagent according to one or more of the embodiments five to seven is according to an eighth embodiment characterized in that the complexing agent(s) is/are selected from the group comprising ethylenediamine tetraacetic acid (EDTA), ethylene glycol-bis(aminoethylether)-N,N'-tetraacetic acid (EGTA) and ethylenediamine disuccinic acid (EDDS).

The method and/or reagent according to one or more of the embodiments five to eight is according to a ninth embodiment characterized in that the protein(s) is/are selected from one or more of the following groups:

a. albumin selected from animal, plant and/or human albumin, preferably bovine serum albumin (BSA), b. globulin selected from animal, plant, and/or human globulin, preferably γ-globulin.

The reagent and/or method according to one or more of the embodiments five to nine is according to a tenth embodiment characterized in that a. the reagent used for the pretreatment of the sample material has at least one of the following features:
   i. the total concentration of the compound comprising an amino group and/or combinations of various of these compounds in the reagent is 5 mM to 500 mM, preferably 25 mM to 350 mM, especially preferably 50 mM to 250 mM,
   ii. the total concentration of the detergent in the reagent is 0.1% (v/v) to 5% (v/v), preferably 0.2% (v/v) to 4% (v/v), and preferably 0.5% (v/v) to 3% (v/v) and also preferably 1% (v/v) to 3% (v/v), preferably for the use of Triton X-100 0.2% (v/v) to 0.5% (v/v), preferably for the use of Tween 20 1% (v/v) to 5% (v/v), wherein the detergent is preferably a non-ionic surfactant,
   iii. the total concentration of the complexing agent(s) in the reagent is 10 mM to 500 mM, preferably 10 mM to 100 mM,
   iv. the total concentration of the protein or proteins in the reagent is 1 mg/mL to 100 mg/mL, preferably 2 mg/mL to 25 mg/mL, 2 mg/mL to 10 mg/mL and more preferably 4 mg/mL to 10 mg/mL, preferably for the use of IgG and BSA 2 mg/mL to 25 mg/mL,
   v. the pH value of the reagent lies in the range from pH 3 to pH 9, b. the components of the reagent in the reaction mixture of sample material and reagent have at least one of the following features:
   i. the total concentration of the compound comprising an amino group and/or combinations of various of these compounds in the reaction mixture is 2.5 mM to 400 mM, preferably 12.5 mM to 280 mM, especially preferably 25 mM to 200 mM,
   ii. the total concentration of the detergent in the reaction mixture is 0.05% (v/v) to 4% (v/v), preferably 0.1% (v/v) to 3% (v/v), and preferably 0.25% (v/v) to 2.5% (v/v) and also preferably 5% (v/v) to 2.5% (v/v), preferably for the use of Triton X-100 0.1% (v/v) to 0.4% (v/v), preferably for the use of Tween 20 0.5% (v/v) to 4% (v/v), wherein preferably a non-ionic surfactant is used as detergent,
   iii. the total concentration of the complexing agent(s) in the reaction mixture is 5 mM to 400 mM, preferably 5 mM to 80 mM,
   iv. the total concentration of the protein or proteins in the reaction mixture is 0.5 mg/mL to 80 mg/mL, preferably 1 mg/mL to 20 mg/mL, 1 mg/mL to 8 mg/mL and also preferably 2 mg/mL to 8 mg/mL, preferably for the use of IgG and BSA 1 mg/mL to 20 mg/mL, c. the reagent is mixed with the sample material in the ratio 1+4 ($V_{reagent}+V_{sample\ material}$) to 4+1 ($V_{reagent}+V_{sample\ material}$), preferably 1+2 ($V_{reagent}+V_{sample\ material}$) to 2+1 ($V_{reagent}+V_{sample\ material}$), especially preferably 1+1 ($V_{reagent}+V_{sample\ material}$),
d. the reagent does not contain an aqueous formulation that contains phosphate and/or citrate in an overall concentration of ≥5 mM,
e. the method has an LOD (limit of detection) of at least 1 pg, preferably at least 0.1 pg, and/or f. the recovery rate of the isolated target nucleic acid is at least 50%, preferably at least 75%, especially preferably at least 85%.

According to an eleventh embodiment, a method is provided for isolation and/or purification of at least one target nucleic acid from a bioprocess sample, which preferably comprises at least one biopharmaceutical, characterized in that the method comprises the following steps:

a. pretreating the bioprocess sample with a reagent, wherein the reagent comprises at least one or more compounds with an amino group, selected from one or more of the following groups:
   i. polar-neutral proteinogenic α-aminocarboxylic acids, preferably asparagine, cysteine, glutamine, glycine, threonine and serine,
   ii. nonpolar-hydrophobic proteinogenic α-aminocarboxylic acids, preferably alanine, leucine, isoleucine, methionine, proline and valine,
   iii. basic α-aminocarboxylic acids, preferably arginine, lysine and ornithine,
   iv. non-proteinogenic aminocarboxylic acids, selected from the group comprising β-alanine, D-alanine, L-homoserine and D-valine,
   v. aminocarboxylic acid polymers comprising at least one of the aminocarboxylic acids mentioned in (i.) to (iv.), preferably consisting of the aminocarboxylic acids mentioned in (i.) to (iv.), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine,
   vi. peptides from 2 to 4 aminocarboxylic acids, comprising at least one of the aminocarboxylic acids mentioned in (i.) to (iv.), preferably consisting of the aminocarboxylic acids mentioned in (i.) to (iv.), preferably selected from identical or different aminocarboxylic acids mentioned in (i.) to (iv.), preferably glycine dimers, glycine trimers and glycine tetramers,
   vii. a compound of the general formula $R^3R^4N$—$CR^1R^2$—COOH (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, di(hydroxyalkyl) and tri(hydroxyalkyl), wherein the alkyl component has a chain length from C1 to C5, is branched or unbranched, is saturated or unsaturated, and wherein at least one of $R^1$, $R^2$, $R^3$ and $R^4$ is not hydrogen, preferably selected from the group N-(tri(hydroxymethyl)methyl)glycine (tricine) and N,N-bis(2-hydroxyethyl)glycine (bicine),
   viii. a compound of the general formula $R^3R^4N$—$CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated, wherein the compound is preferably Tris(hydroxymethyl)-aminomethane (Tris), b. preferably mixing of the reagent with the bioprocess sample,
c. isolation and/or purification of nucleic acids from the bioprocess sample, which is contacted with and/or mixed with the reagent,
d. optionally quantitative and/or qualitative detection of at least a portion of the isolated target nucleic acids, preferably quantitative detection by amplification of a nucleic acid segment that is to be detected.

According to a twelfth embodiment, said method according to the eleventh embodiment is characterized by one or more of the following features:

a. the bioprocess sample is a purification fraction obtained in a purification process for a biotechnologically produced product, preferably a biopharmaceutical,
b. the biopharmaceutical is a pharmaceutically active substance, preferably comprising one or more biomolecules,
c. the target nucleic acid represents a contamination of the bioprocess sample,
d. the target nucleic acid comprises DNA from a host cell and/or host organism used for the production of a biotechnologically produced product, wherein the host cell is preferably an immortalized host cell,
e. the method has an LOD (limit of detection) of at least 1 pg, preferably at least 0.1 pg,
f. the isolation and/or detection of the isolated target nucleic acid is quantitative, and/or
g. the recovery rate of the isolated target nucleic acid is at least 50%, preferably at least 75%, especially preferably at least 85%.

According to a thirteenth embodiment, the method according to the eleventh or twelfth embodiment is characterized in that the isolation in step (c.) comprises at least one, preferably both of the following steps:
   c.1) adding at least one lysis reagent to the bioprocess sample pretreated according to (a.), wherein at least one proteolytic enzyme and/or a chaotropic agent containing reagent is added as lysis reagent,
   c.2) isolating the target nucleic acid, preferably by binding to a carrier material, wherein for binding, preferably a binding reagent is added that comprises an alcohol and/or a chaotropic compound.

According to a fourteenth embodiment a method is provided for detecting at least one target nucleic acid from different bioprocess samples obtained from a purification process, characterized in that the target nucleic acid is isolated from the bioprocess samples to be investigated by the method described above and at least a portion of the isolated target nucleic acid is detected.

According to a fifteenth embodiment the method according to the fourteenth embodiment is characterized by one or more of the following features:

a. the reagent that is used for the pretreatment of the bioprocess sample comprises at least one of the following features:
   i. the total concentration of the compound comprising an amino group and/or combinations of various of these compounds in the reagent is 5 mM to 500 mM, preferably 25 mM to 350 mM, especially preferably 50 mM to 250 mM,
ii. the total concentration of the detergent in the reagent is 0.1% (v/v) to 5% (v/v), preferably 0.2% (v/v) to 4% (v/v), and preferably 0.5% (v/v) to 3% (v/v) and also preferably 1% (v/v) to 3% (v/v), preferably for the use of Triton X-100 0.2% (v/v) to 0.5% (v/v), preferably for the use of Tween 20 1% (v/v) to 5% (v/v), preferably the detergent or the detergents is/are a non-ionic surfactant and especially preferably is/are selected from the group of detergents defined in the seventh embodiment,
iii. the total concentration of the complexing agent(s) in the reagent is 10 mM to 500 mM, preferably 10 mM to 100 mM, preferably the complexing agent is selected from the group of complexing agents defined in the eighth embodiment,
iv. the total concentration of protein in the reagent is 1 mg/mL to 100 mg/mL, preferably 2 mg/mL to 25 mg/mL, 2 mg/mL to 10 mg/mL and also preferably 4 mg/mL to 10 mg/mL, preferably for the use of IgG and BSA 2 mg/mL to 25 mg/mL, preferably the protein is selected from the group defined in the ninth embodiment,
v. the pH of the reagent is in the range from pH 3 to pH 9, and/or
vi. the reagent is a reagent according to one or more of the embodiments six to ten,
b. in the reaction mixture of bioprocess sample and reagent obtained in step (a.) according to the eleventh embodiment the components of the reagent have at least one of the following features:
i. the total concentration of the compound comprising an amino group and/or the combination of various of these compounds is 2.5 mM to 400 mM, preferably 12.5 mM to 280 mM, especially preferably 25 mM to 200 mM,
ii. the total concentration of the detergent in the reaction mixture is 0.05% (v/v) to 4% (v/v), preferably 0.1% (v/v) to 3% (v/v), and preferably 0.25% (v/v) to 2.5% (v/v) and also preferably 5% (v/v) to 2.5% (v/v), preferably for the use of Triton X-100 0.1% (v/v) to 0.4% (v/v), preferably for the use of Tween 20 0.5% (v/v) to 4% (v/v), preferably the detergent is a non-ionic surfactant and especially preferably is selected from the group of detergents defined in the seventh embodiment,
iii. the total concentration of the complexing agent(s) in the reaction mixture is 5 mM to 400 mM, preferably 5 mM to 80 mM, and/or
iv. the total concentration, in the reaction mixture, of the protein contained in the reagent is 0.5 mg/ml to 80 mg/mL, preferably 1 mg/mL to 20 mg/mL, 1 mg/mL to 8 mg/mL and also preferably 2 mg/mL to 8 mg/mL, preferably for the use of IgG and BSA 1 mg/mL to 20 mg/mL,
c. in step (a.) the reagent is mixed with the bioprocess sample in the ratio 1+4 ($V_{reagent}+V_{sample\ material}$) to 4+1 ($V_{reagent}+V_{sample\ material}$), preferably 1+2 ($V_{reagent}+V_{sample\ material}$) to 2+1 ($V_{reagent}+V_{sample\ material}$), especially preferably 1+1 ($V_{reagent}+V_{sample\ material}$),
and/or
d. the reagent does not comprise an aqueous formulation that contains phosphate and/or citrate in an overall concentration of ≥5 mM.

According to a sixteenth embodiment, the invention pertains to the use of a reagent for preparing a biopharmaceutical-containing bioprocess sample for subsequent nucleic acid isolation and/or purification, characterized in that the reagent comprises the following components:
a. at least one or more compounds comprising an amino group, from one or more of the following groups:
i. polar-neutral proteinogenic α-aminocarboxylic acids, preferably asparagine, cysteine, glutamine, glycine, threonine and serine,
ii. nonpolar-hydrophobic proteinogenic α-aminocarboxylic acids, preferably alanine, leucine, isoleucine, methionine, proline and valine,
iii. basic α-aminocarboxylic acids, preferably arginine, lysine and ornithine,
iv. non-proteinogenic aminocarboxylic acids, selected from the group comprising β-alanine, D-alanine, L-homoserine and D-valine,
v. aminocarboxylic acid polymers comprising at least one of the aminocarboxylic acids mentioned in (i.) to (iv.), preferably consisting of the aminocarboxylic acids mentioned in (i.) to (iv.), preferably formed from identical, two or several different aminocarboxylic acid monomers, preferably in conjunction with halides, preferably selected from the group poly-L-lysine, poly-L-lysine hydrobromide, poly-L-lysine hydrochloride, poly(L-glutamine, L-alanine), poly(L-glutamine, L-lysine) hydrobromide, poly-L-ornithine,
vi. peptides from 2 to 4 aminocarboxylic acids, comprising at least one of the aminocarboxylic acids mentioned in (i.) to (iv.), preferably consisting of the aminocarboxylic acids mentioned in (i.) to (iv.), preferably selected from identical or different aminocarboxylic acids mentioned in (i.) to (iv.), preferably glycine dimers, glycine trimers and glycine tetramers,
vii. a compound of the general formula $R^3R^4N$—$CR^1R^2$—COOH (I), wherein $R^1$ and $R^2$ are selected independently of one another from the group consisting of hydrogen, alkyl, hydroxyalkyl, aminoalkyl and thioalkyl, and wherein $R^3$ and $R^4$ are selected independently of one another from the group consisting of hydrogen, alkyl, hydroxyalkyl, di(hydroxyalkyl) and tri(hydroxyalkyl), wherein the alkyl component has a chain length from C1 to C5, is branched or unbranched, is saturated or unsaturated, and wherein at least one of $R^1$, $R^2$, $R^3$ and $R^4$ is not hydrogen, preferably selected from the group N-(tri(hydroxymethyl)methyl)glycine (tricine) and N,N-bis(2-hydroxyethyl)glycine (bicine),
viii. a compound of the general formula $R^3R^4N$—$CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl, wherein preferably at least one of $R^5$, $R^6$ and $R^7$ is a hydroxyalkyl, and wherein the alkyl component has a chain length from C1 to C5, is branched or unbranched, is saturated or unsaturated, wherein the compound is preferably Tris(hydroxymethyl)-aminomethane (Tris), and optionally one or more of the following components:
b. at least one detergent,
c. at least one complexing agent,
d. at least one protein,
wherein the reagent is preferably a reagent according to the embodiments six to ten.

According to a seventeenth embodiment a kit is provided for the isolation and/or purification of nucleic acids from a sample material, which contains a reagent according to one or more of the embodiments six to 10.

According to an eighteenth embodiment, the kit according to the seventeenth embodiment preferably comprises at least one or more of the following components:

a. a carrier material, preferably containing silica, glass fibre, polyalkylenes, e.g. PP, PE/PP, PE, for separating the target nucleic acids, wherein the carrier material is used in particle form, as non-woven fabric, as fibres, as gel matrix, as membrane, preferably as column packing material, wherein the particles are preferably in the form of beads, preferably as magnetic particles, more preferably as magnetic beads, b. one or more formulations that serve as lysis reagent, preferably comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, c. one or more enzymes, preferably proteinase K, DNase and/or RNase, d. one or more formulations that serve as binding reagent, preferably comprising at least one chaotropic compound and/or at least one detergent from the group of non-ionic detergents, preferably selected from the group of polyoxyethylene-fatty alcohol ethers, which comprises a fatty alcohol moiety that has 6 to 22 carbon atoms, and comprises a polyoxyethylene moiety that contains 2 to 150 ($CH_2CH_2O$) units, and optionally at least one branched or unbranched alcohol with one to five carbon atoms, e. one or more formulations that serve as washing reagent, preferably comprising at least one branched or unbranched alcohol with one to five carbon atoms, and optionally a chaotropic compound, and/or optionally a detergent from the group of non-ionic surfactants, f. one or more formulations that serve as elution reagent, preferably comprising at least one complexing agent in a buffered milieu.

EXAMPLES

Possible embodiments and advantages of the present invention are described in the following section by way of examples. These examples were carried out as described below.

Example 1: Extraction of Eukaryotic DNA from Various Purification Buffers Using the Reagent According to the Invention The initial sample comprising the nucleic acid to be isolated and purified was a solution from a purification buffer, which is usually employed in column chromatography methods, and to which, for this test, a defined amount of purified chromosomal DNA from CHO cells was added. This sample is a good model system for a regular bioprocess sample. Phosphate and citrate buffers were used as purification buffers: a) PBS pH 7, b) PBS with 1 M NaCl, pH 7 and c) citrate buffer pH 3. A portion of these samples was additionally mixed with the reagent according to the invention. All the samples then underwent automated nucleic acid isolation and purification. The amounts of nucleic acids obtained were detected in a quantitative PCR (qPCR).

The following protocol was followed:

In each case 1 pg of DNA from CHO cells was added to 200 µl of purification buffer. In addition, in each case 100 µl of purification buffer was mixed with 1 pg of DNA from CHO cells and then with 100 µl of the reagent according to the invention (here: 0.1 M glycine solution, pH 3.2). The samples obtained were used in the subsequent automated nucleic acid isolation and purification, which was carried out using the QIAsymphony Virus/Bacteria Kit (QIAGEN) on the QIAsymphony automatic laboratory automat (QIAGEN). Then the isolated DNA in the eluates was detected by quantitative real-time qPCR.

FIG. 1 shows a graphical representation of the result of the experiment:

By adding the reagent according to the invention to the sample consisting of a purification buffer (PBS, PBS+1 M NaCl or citrate buffer) and eukaryotic DNA before nucleic acid isolation and purification, the nucleic acid yield was increased significantly. This can be seen from the considerably lower ct (cycle of threshold) values of these samples (ct=35.5-36.5) compared to the samples that were not pretreated with the reagent according to the invention (ct=39.6-40). The DNA in the fraction containing citrate buffer showed a signal in the PCR-negative-control/non-template control (NTC) region, i.e. no nucleic acid could be isolated and therefore detected. Nucleic acid could only be extracted and detected from the sample containing a citrate buffer after treatment with the reagent according to the invention. The results show that despite the very different nature of the initial samples, pretreatment according to the invention not only had the effect that in some cases isolation of the nucleic acids became possible at all, but in addition similarly good results were achieved with all the samples.

Example 2: Extraction of Eukaryotic DNA from Identical Purification Buffer Aliquots with Addition of Various Reagents The initial samples with the nucleic acid to be isolated were identical solutions from a purification buffer, which is usually employed in ion exchange chromatography, and for this test a defined amount of purified chromosomal DNA from CHO cells was added thereto. A phosphate buffer was used as purification buffer: PBS with 1 M NaCl, pH 7. These samples, which can be regarded as model bioprocess samples, were additionally mixed with one of the following formulations: the reagent according to the invention in two embodiments or a phosphate buffer. All the samples then underwent automated nucleic acid isolation and purification. The amounts of nucleic acids obtained were detected in quantitative PCR.

The following protocol was followed:

In each case 1 pg of DNA from CHO cells was added to three preparations with 200 µl of purification buffer. Then these preparations were mixed with 800 µl of one of the following solutions:

1. reagent according to the invention, according to an especially preferred embodiment (0.1 M glycine-glycine, pH 3.2),
2. lysis buffer from the QIAsymphony Virus/Bacteria Kit (QIAGEN), as a possible embodiment of the reagent according to the invention,
3. PBS, pH 7.2.

Then automated nucleic acid isolation and purification was carried out, as described in example 1. It should be noted that although the lysis buffer of the purification kit had already been used for the pretreatment according to the invention, according to 2. in the subsequent nucleic acid purification the complete purification procedure as described in example 1 was carried out, i.e. the lysis buffer was used again in the nucleic acid purification. Detection and quantification of the isolated nucleic acids in the eluates was carried out by real-time qPCR and by comparison with a previously prepared standard series, for which purified DNA from CHO cells was as well used.

Figure 2:
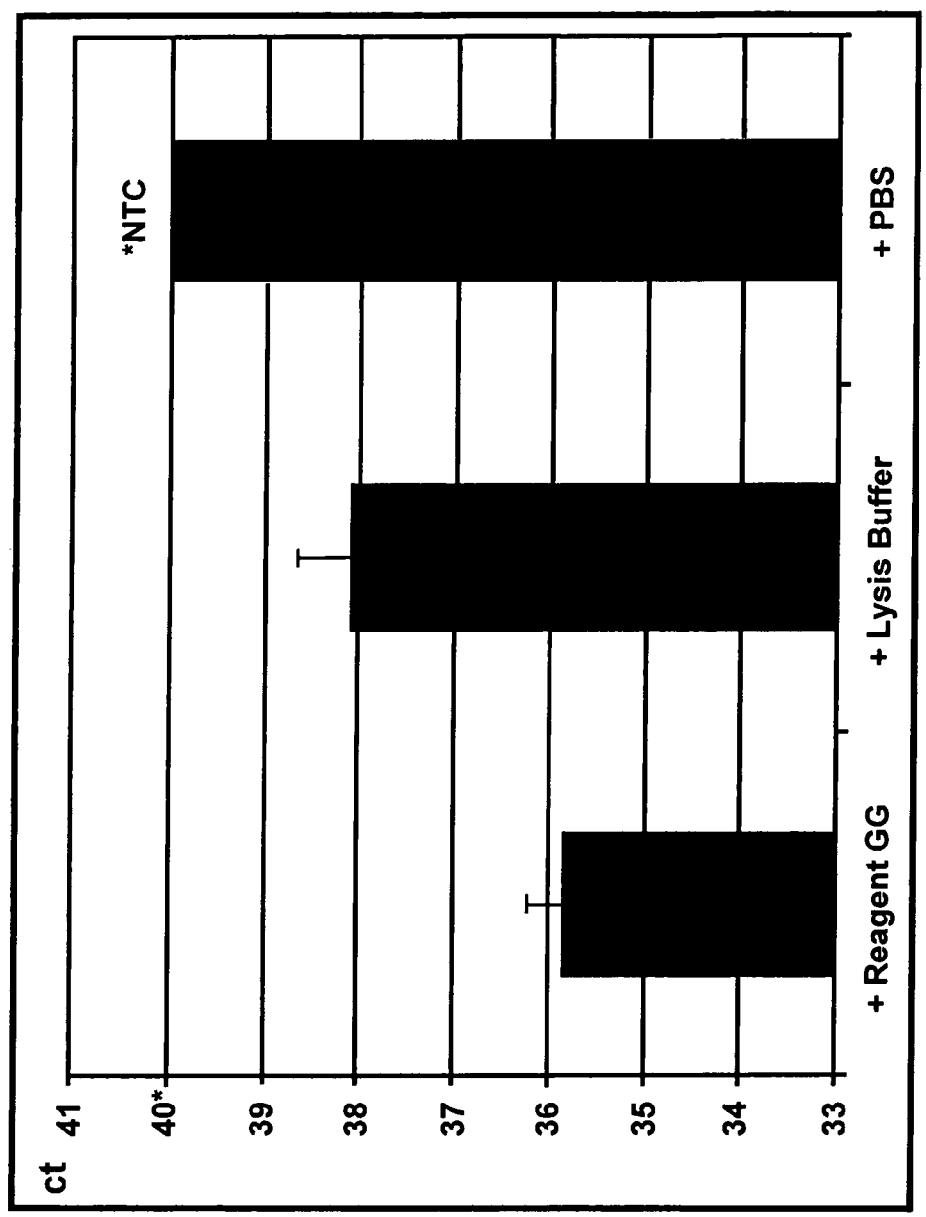
FIG. 2 is a graph showing Ct values of quantitative real-time PCR performed with DNA isolated using different reagents or buffer according to Example 2.
Figure 3:
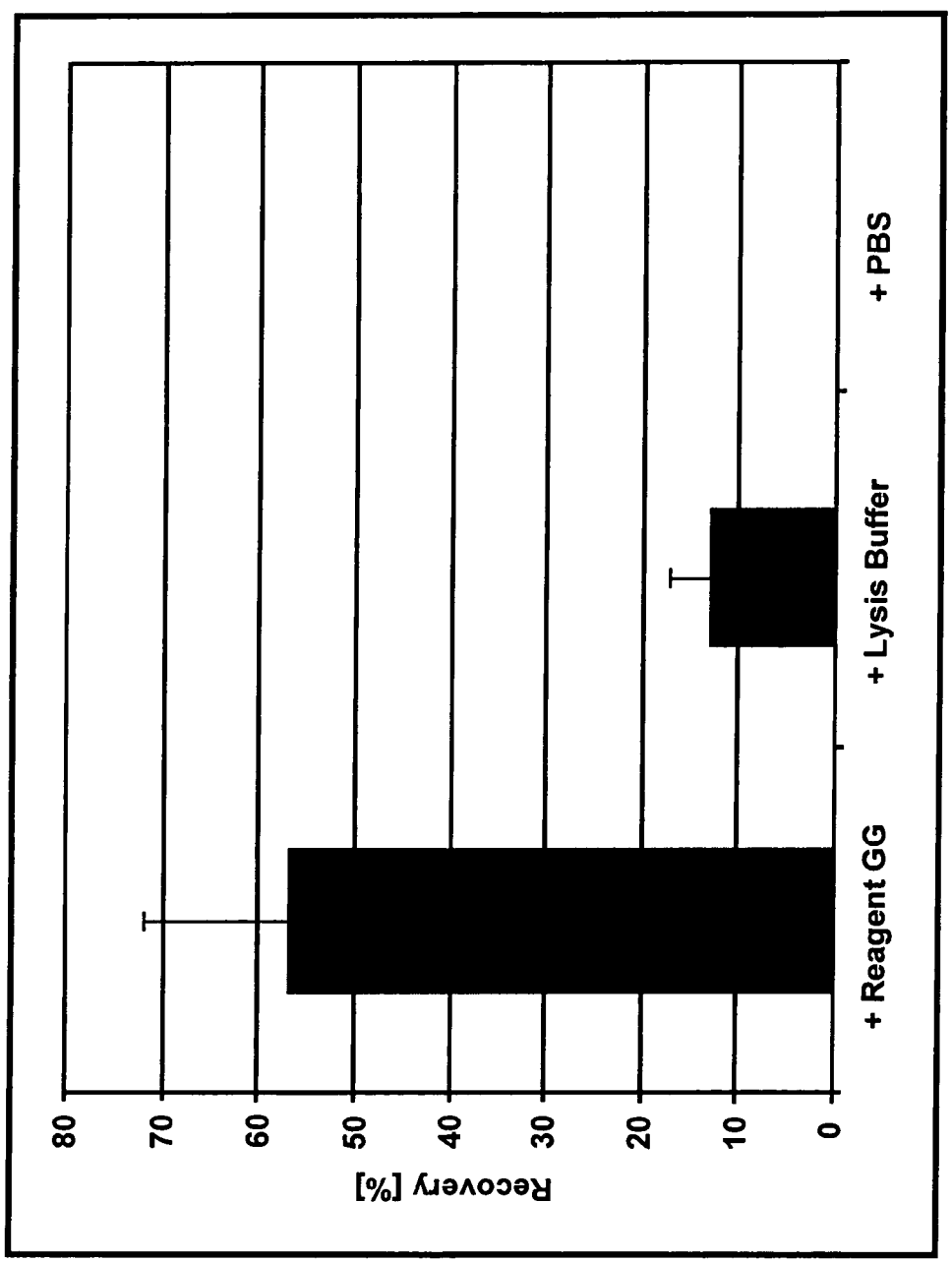
FIG. 3 is a graph showing DNA recovery [%] using different reagents or buffer according to Example 2.

FIGS. 2 and 3 show graphical representations of the result of the experiment:

FIG. 2 also shows, as in example 1 (FIG. 1), a significant increase in nucleic acid yield as a result of the pretreatment of the sample consisting of purification buffer (PBS+1 M NaCl) and eukaryotic DNA with a reagent according to the invention. Addition of the known lysis buffer for the purpose of pretreatment of the sample, before subsequently carrying out a further digestion of the sample and isolation of the nucleic acids (using the QIAsymphony Virus/Bacteria method, see above), already lowers the ct value to 38. A preferred embodiment of the reagent according to the invention led to an even more pronounced lowering of the ct value to 36. The comparatively much higher ct value (ct=40), which was detected for the sample to which PBS was added instead of the reagent according to the invention (and hence without pretreatment according to the invention), shows that a much smaller amount of nucleic acid was isolated and purified from this sample. The pure phosphate buffer (PBS) had an inhibitory effect on nucleic acid isolation, so that as in a pure citrate buffer sample (see example 1), a signal was detected in the region of the PCR-negative-control (NTC). This finding also clearly demonstrates the problems that can arise in the purification of nucleic acids from classical bioprocess samples, for example purification fractions, because based on the purification buffers commonly used, a classical purification using standard methods is not possible. The additional pretreatment with the lysis reagent from the purification kit already permitted the isolation of nucleic acids, but to a smaller extent than the pretreatment with the more preferred embodiment of the reagent according to the invention. FIG. 3 shows that addition of the lysis reagent resulted in a nucleic acid recovery rate of 13%, whereas addition of a preferred embodiment of the reagent according to the invention resulted in a recovery rate of 57%, and therefore a significant increase in DNA yield was achieved.

The results from examples 1 and 2 provide evidence that as a result of pretreatment of the sample with the reagent according to the invention prior to isolating the nucleic acid subsequently, a significant increase was achieved in the nucleic acid recovery from different purification buffers that are usually employed of purification methods applying column chromatography. Sometimes isolation of the nucleic acids was only made possible by the pretreatment according to the invention. The results also show that the use of a classical method of isolation and purification without pretreatment of the sample with the reagent according to the invention, did not enable nucleic acid isolation for samples in which the nucleic acid to be isolated was contained for example in a pure phosphate-containing or citrate-containing purification buffer. Instead, a high phosphate and citrate content had an inhibitory effect on the nucleic acid isolation and hence on the nucleic acid recovery in the eluates. Accordingly, nucleic acid purification from bioprocess samples—without special measures—is usually impossible, especially if the sample only contains small amounts of the nucleic acids.

By using the reagent and method according to the invention, there was a significant improvement in the yield of the nucleic acids isolated, which was reflected for example in a considerably increased recovery of nucleic acids that were only present in small amounts. The method according to the invention therefore provided, due to its sensitivity, far more reliable information regarding the content of residual host cell DNA and/or other nucleic acid contaminants during and after purification of biopharmaceutical active substances, especially if only very small amounts of contaminating nucleic acids (for example of the host organisms) were present in the purification fraction. The present experiments were carried out successfully with only 1 pg of DNA per sample, i.e. with a tenth of the official recommended limit of 10 pg of host cell DNA per dose of medicinal product. The use of the reagent and the method according to the invention therefore represents a very sensitive, efficient, effective and reliable method of nucleic acid isolation and purification, which is especially suitable for monitoring and assessing the purification process of bioprocess samples, with respect to small amounts of residual host cell nucleic acids quantitatively up to the end product.

Example 3: Extraction of Eukaryotic DNA from Identical Purification Buffer Aliquots by Means of the Reagent According to the Invention Under the Influence of Protein The initial samples used for this test were solutions from a purification buffer, to which a defined amount of purified chromosomal DNA from CHO cells was added. As in example 2, the purification buffer used was a phosphate buffer that is usually employed in column chromatography methods: PBS with 1 M NaCl, pH 7. These samples, which can also be regarded as model bioprocess samples, were mixed with a protein-containing reagent according to the invention, testing various embodiments of the reagent that only differed in the protein concentration.

The following protocol was followed:

In each case, 1 pg of DNA from CHO cells was added to four preparations with 200 µl of purification buffer. These preparations were then each mixed with 800 µl of 0.2 M bicine solution, which contained BSA at concentrations of 0, 5, 50 or 100 mg/ml. Then automated nucleic acid isolation and purification, as well as subsequent analysis as described in example 1, were carried out.

Figure 4:
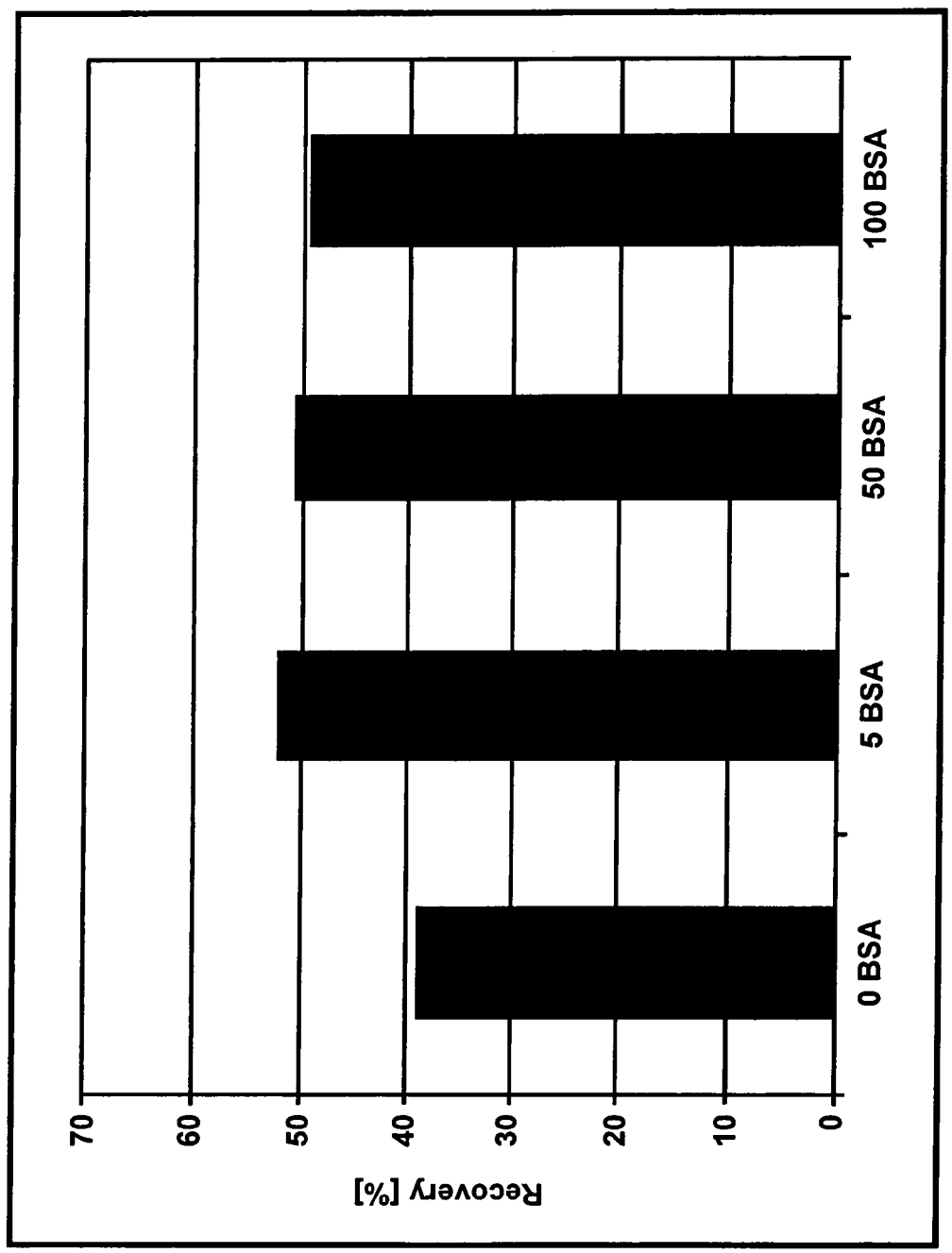
FIG. 4 is a graph showing DNA recovery [%] with or without the addition of BSA at different concentrations to an exemplary reagent according to Example 3.

FIG. 4 shows in graphical form that the addition of BSA to the reagent according to the invention brought about a marked increase in the nucleic acid recovery rate by more than 10%. A concentration of 5 mg/ml BSA in the reagent was already sufficient to achieve an effect. Further marked elevation of protein concentration did not show any further positive effect on the recovery rate. The result shows that an amino compound in combination with a protein could bring about optimization of the effectiveness of the reagent according to the invention.

Example 4: Extraction of Eukaryotic DNA from Various Purification Buffer Aliquots by Means of the Reagent According to the Invention and Various Proteins The initial samples for this test were two different purification buffers, to which a defined amount of purified chromosomal DNA from CHO cells and a defined amount of a protein were added, wherein the proteins BSA and IgG were used. The purification buffers used were phosphate and citrate buffers, which are usually employed in column-chromatographic methods: PBS with 1 M NaCl, pH 7 and citrate, pH 3.2. The prepared samples were then mixed with the reagent according to the invention for the subsequent nucleic acid isolation and purification.

The following protocol was followed:

In each case 1 pg of DNA from CHO cells was added to two preparations with 200 µl PBS with 1 M NaCl and three preparations with citrate, so that model bioprocess samples were obtained, based on the purification buffers used. Subsequently 5 mg/mL IgG was added in each case to one PBS preparation and one citrate preparation, and 5 mg/mL BSA was added to another citrate preparation. 800 µl of 0.2 M bicine solution was added to each of the so arranged test preparations. Then nucleic acid isolation and purification, as well as subsequent analysis, were carried out as described in example 1.

Figure 5:
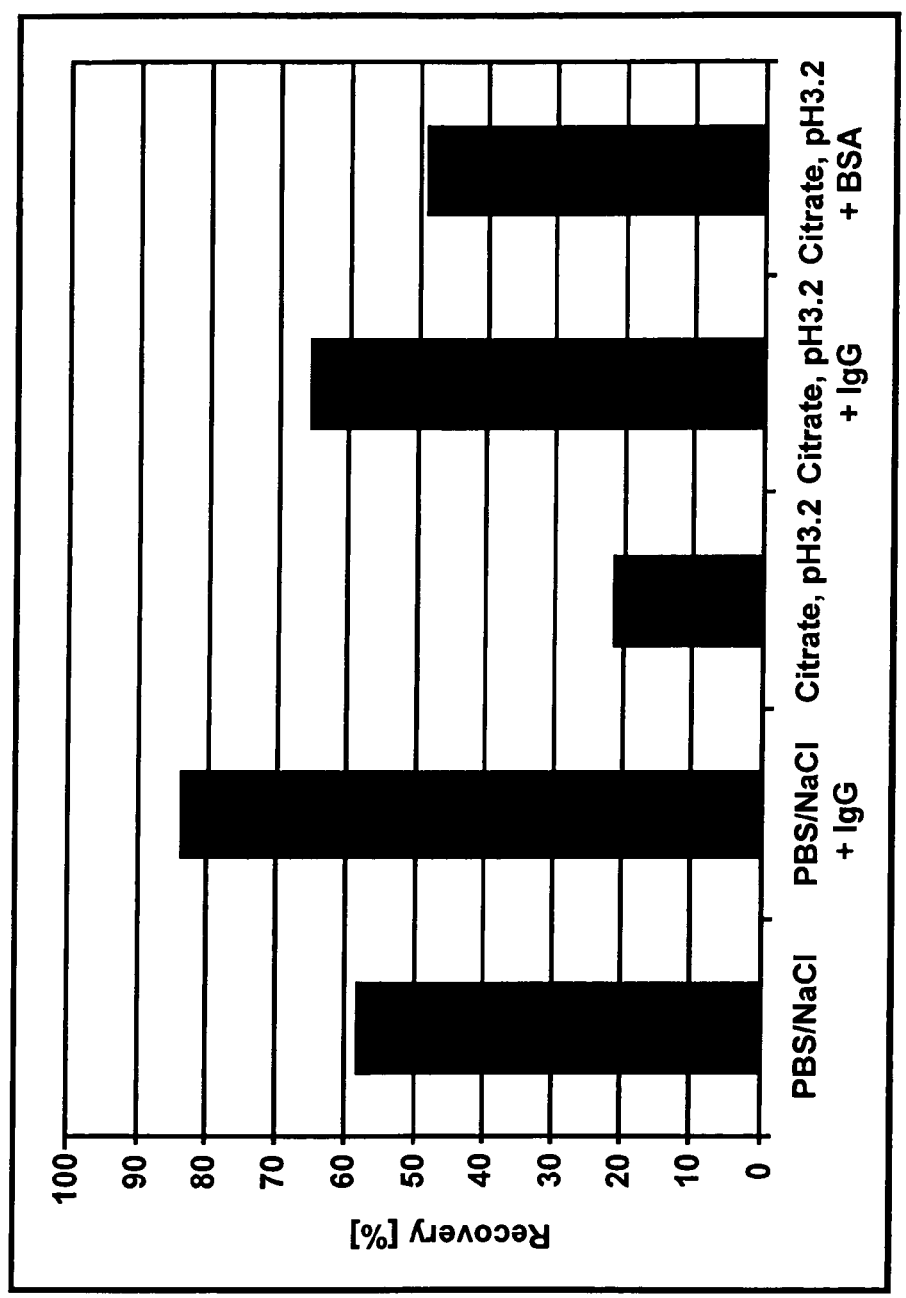
FIG. 5 is a graph showing DNA recovery [%] with the addition of BSA or IgG to a bioprocess model sample according to Example 4.

FIG. 5 confirms the result of example 3 in a graphical form. The addition of BSA, as well as of IgG, to the bioprocess model sample had a significant positive effect on the nucleic acid recovery rate of the added DNA, wherein the positive effect of IgG versus that of BSA was even somewhat greater, with more than 15% recovery rate. Moreover, the results of examples 3 and 4 show that the positive effect on the nucleic acid recovery rate could be achieved in two ways: a) by successive addition of protein and reagent according to the invention with amino compound to the model bioprocess sample (example 4), or b) by addition in one step, wherein the reagent according to the invention contained a combination of protein and amino compound.

Example 5: Extraction of Eukaryotic DNA from Identical Purification Buffer Aliquots with Addition of Various Formulations of the Reagent According to the Invention The initial samples with the nucleic acid to be isolated and purified were identical solutions from a purification buffer, to which a defined amount of purified chromosomal DNA from CHO cells was added. The purification buffer used was, as in examples 1-4, a phosphate buffer that is usually employed as purification buffer in column-chromatographic methods: PBS with 1 M NaCl, pH 7. These samples, which can be regarded as model bioprocess samples, were additionally mixed with one of the following formulations: the sample supplied with DNA itself or the reagent according to the invention in 13 different embodiments. All samples then underwent automated nucleic acid isolation and purification. The amounts of nucleic acids obtained were detected in quantitative PCR.

The following protocol was followed:

In each case 1 pg of DNA from CHO cells was added to 14 preparations, each with 500 µl of purification buffer. Then these preparations were mixed with 500 µl of one of the following solutions:
1. purification buffer PBS with 1M NaCl, pH 7, containing 1 pg of DNA from CHO cells,
2. reagent G1
3. reagent G2
4. reagent GG1
5. reagent GG2
6. reagent GG3
7. reagent B1
8. reagent B2
9. reagent B3
10. reagent B4
11. reagent T1
12. reagent T2
13. reagent T3
14. reagent T4, wherein solutions 2-14 represented various embodiments of the reagent according to the invention with the constituents listed in Table 1.

TABLE 1

Various embodiments of the reagent according to the invention

| Reagent | EDTA [mM] | Triton X-100 [% (v/v)] | Tween 20 [% (v/v)] | hIgG [mg/ml] |
|---|---|---|---|---|
| G1 - 0.2M glycine, pH 3.2 | 10 | 0.2 | 2 | 5 |
| G2 - 0.2M glycine, pH 3.2 | 30 | 0.3 | 3 | 5 |
| GG1 - 0.2M glycine-glycine, pH 3.2 | 10 | 0.2 | 2 | 5 |
| GG2 - 0.2M glycine-glycine, pH 3.2 | 30 | 0.3 | 3 | 5 |
| GG3 - 0.2M glycine-glycine, pH 3.2 | 60 | 0.4 | 4 | 5 |
| B1 - 0.2M bicine, pH 8 | 10 | 0.2 | 2 | 5 |
| B2 - 0.2M bicine, pH 8 | 30 | 0.3 | 3 | 5 |
| B3 - 0.2M bicine, pH 8 | 60 | 0.4 | 4 | 5 |
| B4 - 0.2M bicine, pH 8 | 100 | 0.5 | 5 | 5 |
| T1 - 50 mM tricine, pH 8 | 10 | 0.2 | 2 | 5 |
| T2 - 50 mM tricine, pH 8 | 30 | 0.3 | 3 | 5 |
| T3 - 50 mM tricine, pH 8 | 60 | 0.4 | 4 | 5 |
| T4 - 50 mM tricine, pH 8 | 100 | 0.5 | 5 | 5 |

Then automated nucleic acid isolation and purification was carried out as described in example 1. The isolated nucleic acids in the eluates were detected and quantified using real-time qPCR and by calculation with a used standard simultanouesly.

Figure 6:
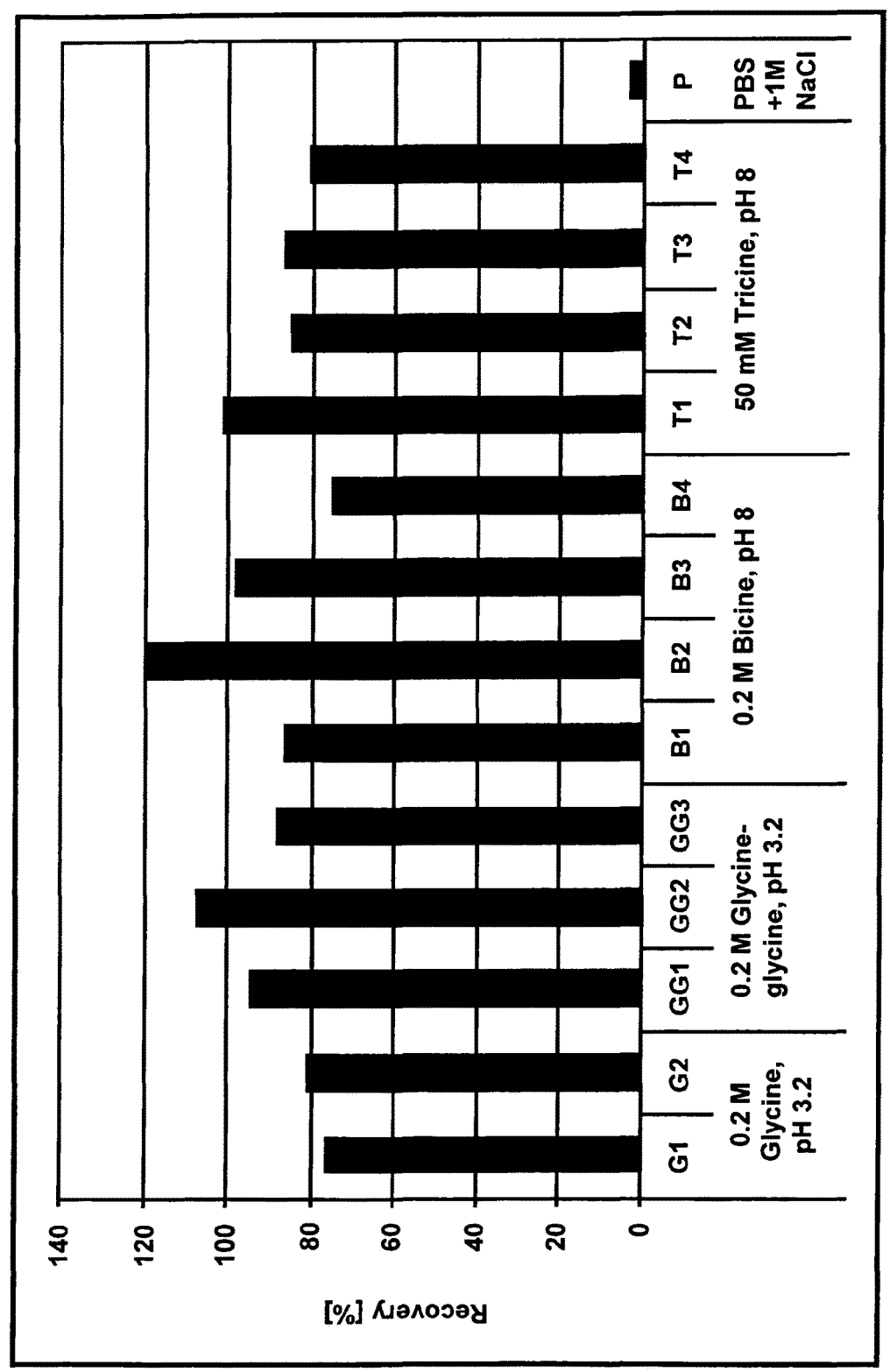
FIG. 6 is a graph showing DNA recovery [%] using different reagents according to Example 5.

FIG. 6 shows a graphical representation of the result of the experiment:

The results show that by using EDTA, Triton X-100, Tween 20 and human IgG (hIgG) as constituents of the reagent according to the invention, the DNA yield in the method of nucleic acid isolation and purification was even further improved. The smallest recovery values, at 75%, were clearly above the recovery value of 58% of example 2, for which the reagent 0.1 M glycine-glycine, pH 3.2 was used. Consequently, both the use of glycine, glycine-glycine, bicine or tricine, and different concentrations of EDTA, Triton X-100, Tween 20 and human IgG (hIgG) had a positive influence on the recovery rate, and therefore offer potential for optimization of the method according to the invention or the reagent according to the invention.

Example 6: Extraction of Eukaryotic DNA from Identical Purification Buffer Aliquots with Various Embodiments of the Reagent According to the Invention The initial samples with the nucleic acid to be isolated and purified were, for this test, solutions from a purification buffer, to which a defined amount of purified chromosomal DNA from CHO cells was added. As in examples 1-5, the purification buffer used was a phosphate buffer, which is also used in column-chromatographic methods: PBS with 1 M NaCl, pH 7. Various embodiments of the reagent according to the invention were added to these samples, which could also be regarded as model bioprocess samples, before carrying out nucleic acid isolation and purification.

The following protocol was followed: For this test, in each case 1 M NaCl (cf. example 1) and 1 pg of DNA from CHO cells were added to 200 µl of purification buffer PBS.

200 μl of this model bioprocess sample was then mixed in each case with 800 μl of the following solutions:
1. 0.2 M glycine pH 3.2
2. 0.1 M Tris pH 8
3. buffer QSL2 (QIAGEN), without detergent
4. buffer QSL2 (QIAGEN)
5. 0.1 M tricine pH 8
6. 0.1 M bicine pH 8
as well as
7. 0.2 M glycine pH 3.2
8. 0.1 M Tris pH 8
9. 0.01 M Tris, 0.075 M arginine pH 8
10. 0.01 M Tris, 0.075 M lysine pH 8
11. 0.05 M tricine pH 8
12. 0.2 M bicine pH 8

Figure 7:
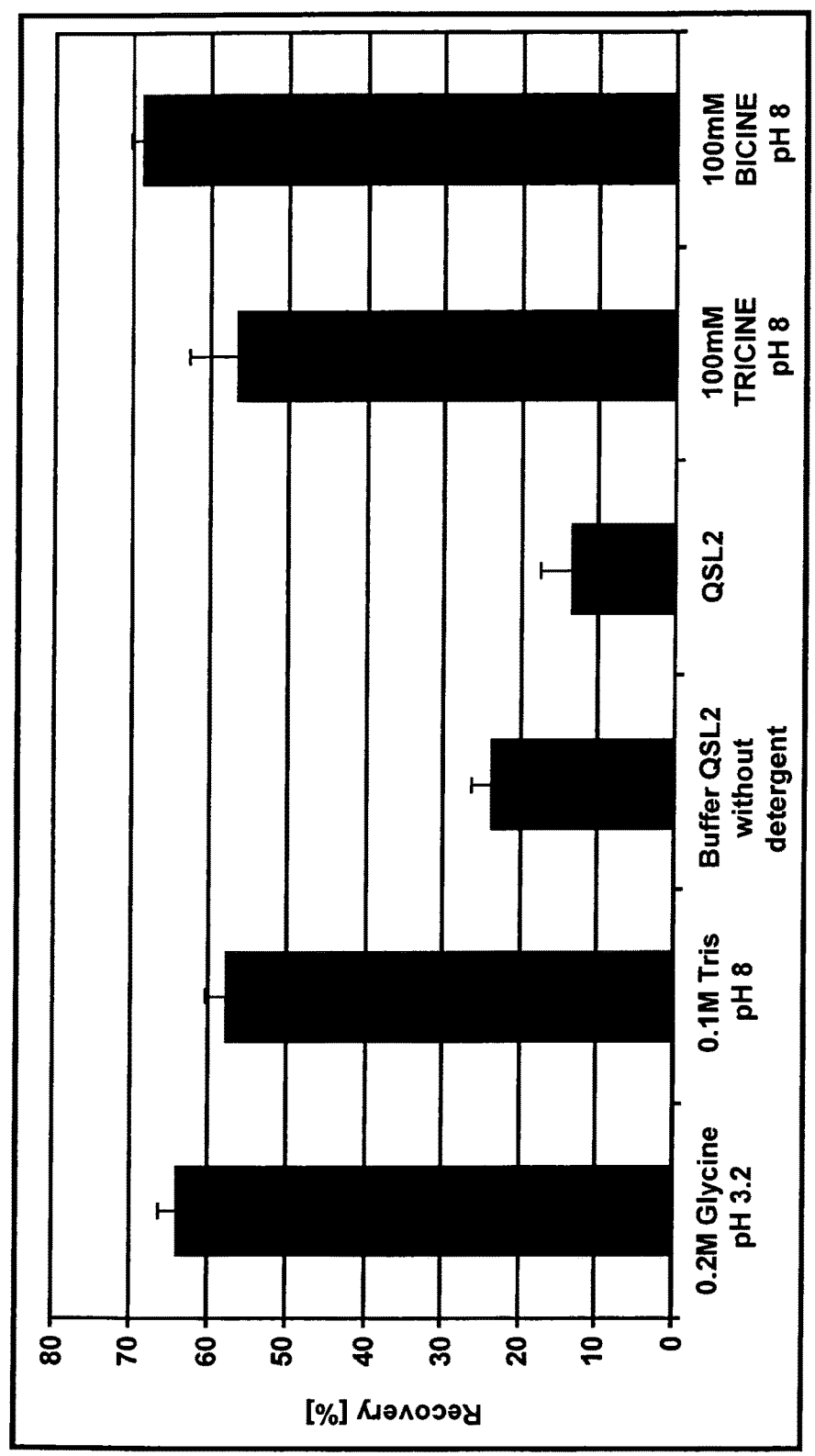
FIG. 7 is a graph showing DNA recovery [%] using different reagents (reagents 1 to 6) according to Example 6.

Isolation of the added chromosomal DNA and subsequent analysis were carried out as described in example 1. The results are shown in FIG. 7 (reagents 1 to 6) and 8 (reagents 7 to 12). The reagents according to the invention 0.2 M glycine pH 3.2, 0.1 M Tris pH 8, 0.1 M tricine pH 8 and 0.1 M bicine pH 8 (see FIG. 7) once again led to a high recovery rate of over 50% and were thus particularly suitable for the pretreatment of bioprocess samples.

Figure 8:
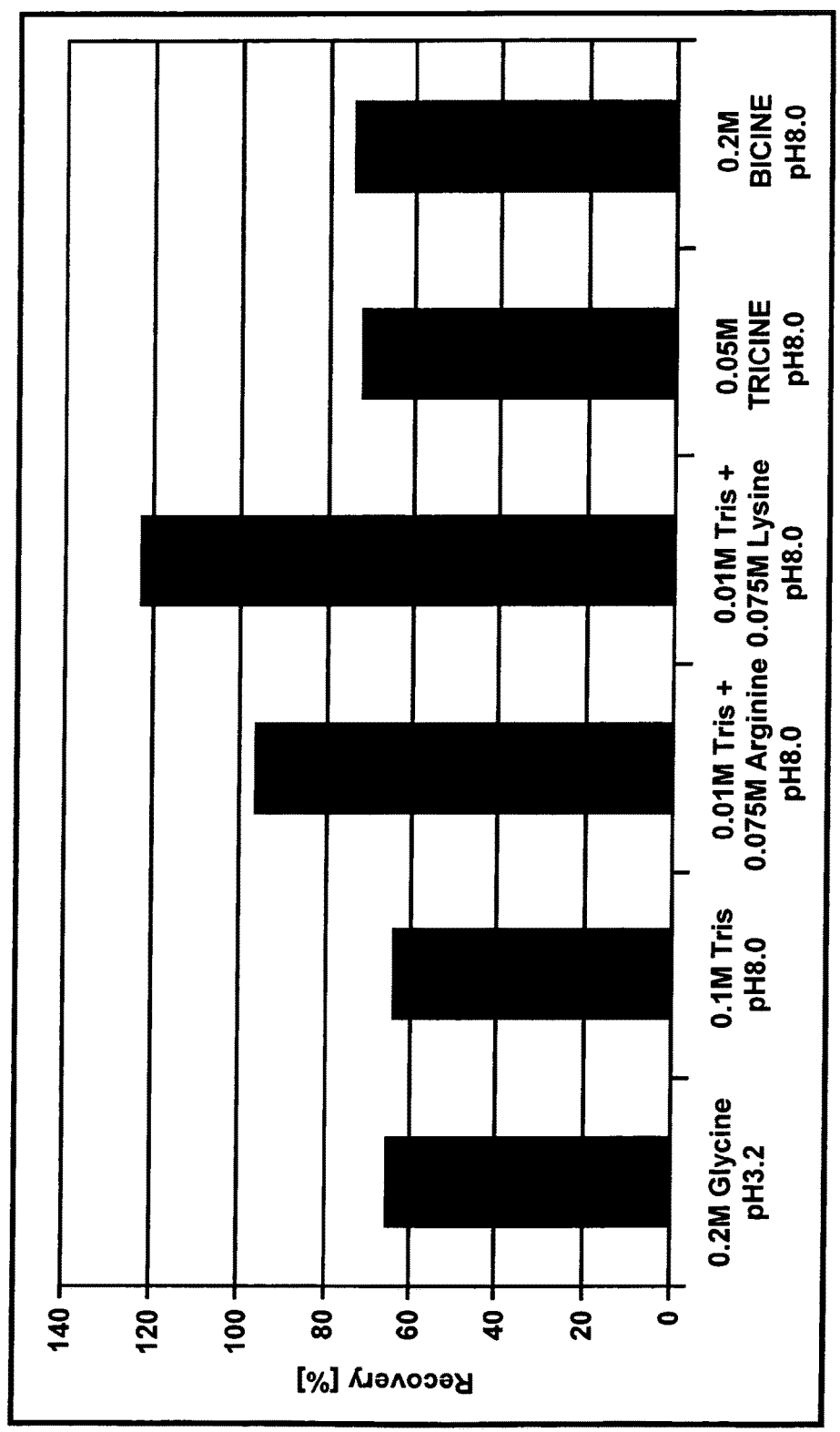
FIG. 8 is a graph showing DNA recovery [%] using different reagents (reagents 7 to 12) according to Example 6.

The results shown in FIG. 8 provide evidence that not only the treatment according to the invention of the sample with the reagents glycine, Tris, tricine and bicine improved the recovery rate, but that also amino acids such as arginine and lysine led to a marked improvement in recovery. In this embodiment, the corresponding amounts of arginine or lysine were added to a low concentration Tris buffer pH 8.

Example 7: Extraction of Eukaryotic DNA from Different Initial Samples

Figure 9:
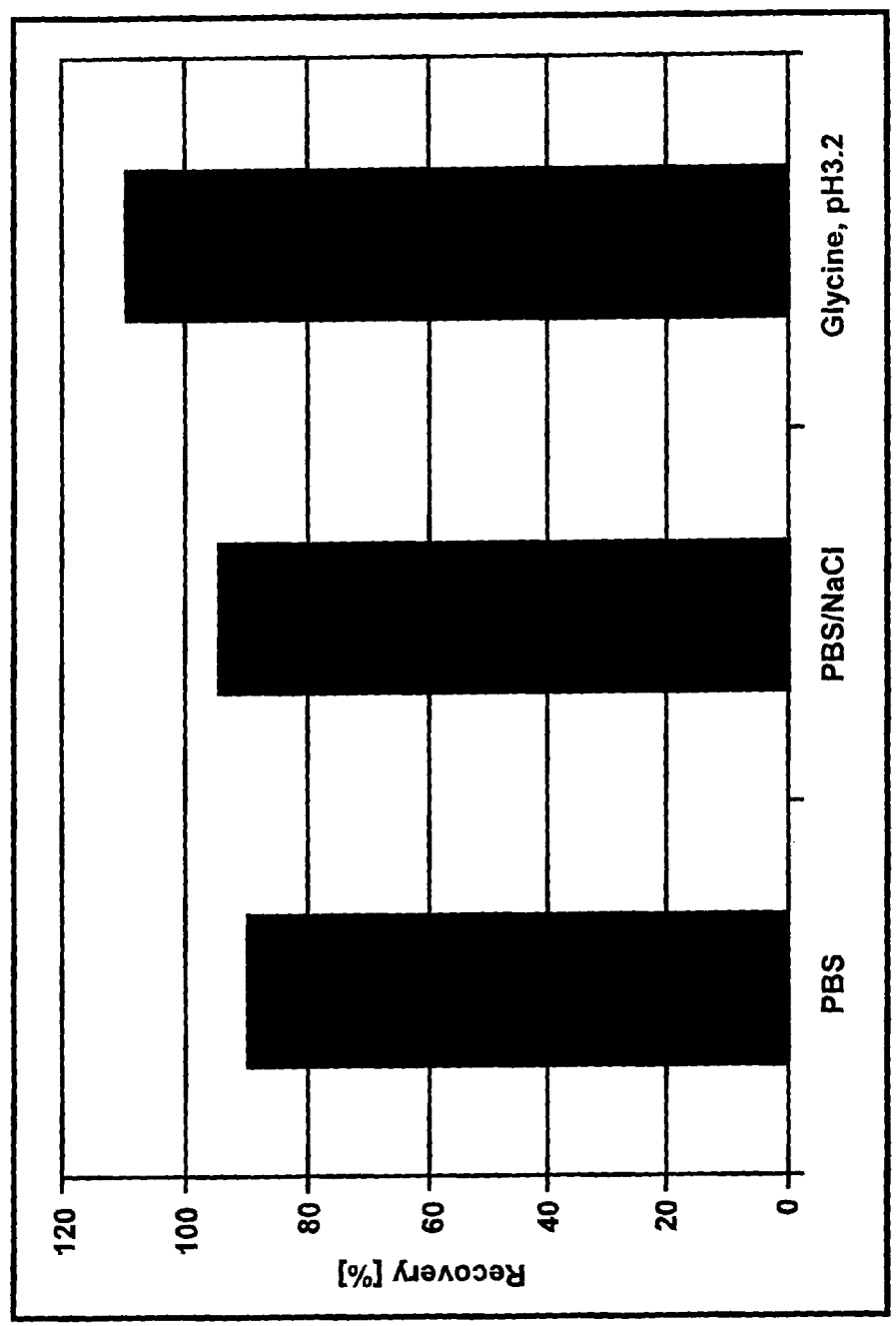
FIG. 9 is a graph showing DNA recovery [%] using different buffers with addition of an exemplary reagent according to Example 7.

The initial samples used for this test were very different purification buffers of column-chromatographic methods: 100 μl PBS, PBS with 1 M NaCl and glycine (see example 1), to which in each case 1 pg of purified chromosomal DNA from CHO cells was added. 100 μl of these model bioprocess samples were each mixed with 100 μl of the reagent according to the invention B2 (see example 3). Isolation of the added chromosomal DNA and subsequent analysis were carried out as described in example 1. The use of the reagent according to the invention again led, both with a PBS buffer and with the glycine buffer, to high recovery rates of over 90%, as shown in FIG. 9. This shows, like example 1, that the reagent according to the invention was particularly suitable for the pretreatment of bioprocess samples of varying composition, because reliable results were provided within tolerable variations, even though a uniform method of purification was used. For this reason the method according to the invention has considerable advantages compared to the prior art, because it is not only more sensitive but can easily be automated.

The invention claimed is:

1. A method of isolation and/or purification of nucleic acids from a sample material, comprising:
   (a) adding a reagent to the sample material, wherein the sample material is a bioprocess sample, wherein the bioprocess sample is a purification fraction obtained in the purification process for a biotechnological product, and wherein the reagent comprises one or more compounds comprising an amino group selected from one or more of the following groups:
      (i) polar-neutral proteinogenic α-aminocarboxylic acids,
      (ii) nonpolar-hydrophobic proteinogenic α-aminocarboxylic acids,
      (iii) basic α-aminocarboxylic acids,
      (iv) non-proteinogenic aminocarboxylic acids selected from the group consisting of β-alanine, D-alanine, L-homoserine and D-valine,
      (v) aminocarboxylic acid polymers comprising at least one of the aminocarboxylic acids of (a)(i) to (a)(iv),
      (vi) peptides from 2 to 4 aminocarboxylic acids, comprising at least one of the aminocarboxylic acids of (a)(i) to (a)(iv),
      (vii) a compound of the general formula $R^3R^4N-CR^1R^2-COOH$ (I), wherein $R^1$ and $R^2$ are selected independently of one another from the group consisting of hydrogen, alkyl, hydroxyalkyl, aminoalkyl and thioalkyl, wherein $R^3$ and $R^4$ are selected independently of one another from the group consisting of hydrogen, alkyl, hydroxyalkyl, di(hydroxyalkyl) and tri(hydroxyalkyl), wherein the alkyl component has a chain length from C1 to C5, is branched or unbranched, is saturated or unsaturated, and wherein at least one of $R^1$, $R^2$, $R^3$ and $R^4$ is not hydrogen, and
      (viii) a compound of the general formula $R^3R^4N-CR^5R^6R^7$ (II), wherein $R^3$ and $R^4$ are selected independently of one another from the group consisting of hydrogen and hydroxyalkyl, and wherein $R^5$, $R^6$ and $R^7$ are selected independently of one another from the group consisting of hydrogen, alkyl and hydroxyalkyl,
   (b) optionally mixing this reagent with the sample material,
   (c) isolating and/or purifying nucleic acid(s) from the sample material that has been contacted with and/or mixed with the reagent, wherein the nucleic acids to be isolated represent a contamination of the bioprocess sample, and
   (d) optionally quantitatively and/or qualitatively detecting at least a portion of the isolated nucleic acid(s).

2. The method of claim 1, wherein the polar-neutral proteinogenic α-aminocarboxylic acids of (a)(i) are asparagine, cysteine, glutamine, glycine, threonine and serine.

3. The method of claim 1, wherein the nonpolar-hydrophobic proteinogenic α-aminocarboxylic acids of (a)(ii) are alanine, leucine, isoleucine, methionine, proline and valine.

4. The method of claim 1, wherein the basic α-aminocarboxylic acids of (a)(iii) are arginine, lysine and ornithine.

5. The method of claim 1, wherein the aminocarboxylic acid polymers of (a)(v) consist of the aminocarboxylic acids of (a)(i) to (a)(iv).

6. The method of claim 1, wherein the aminocarboxylic acid polymer of (a)(v) are formed from an identical aminocarboxylic acid monomer.

7. The method of claim 1, wherein the aminocarboxylic acid polymer of (a)(v) are formed from two or more different aminocarboxylic acid monomers.

8. The method of claim 1, wherein the aminocarboxylic acid polymer of (a)(v) are in conjunction with halides.

9. The method of claim 1, wherein the aminocarboxylic acid polymer of (a)(v) is selected from the group consisting of poly-L-lysine, poly-L-lysine hydrobromide, poly-L-lysine hydrochloride, poly(L-glutamine, L-alanine), poly(L-glutamine, L-lysine) hydrobromide, and poly-L-ornithine.

10. The method of claim 1, wherein the peptides of (a)(vi) consist of the aminocarboxylic acids of (a)(i) to (a)(iv).

11. The method of claim 1, wherein the peptides of (a)(vi) consist of identical aminocarboxylic acids of one of (a)(i) to (a)(iv).

12. The method of claim 1, wherein the peptides of (a)(vi) consist of two or more different aminocarboxylic acids of (a)(i) to (a)(iv).

13. The method of claim 1, wherein the peptides of (a)(v) are glycine dimers, glycine trimmers, and glycine tetramers.

14. The method of claim 1, wherein the compound of (a)(vii) is N-(tri(hydroxymethyl)methyl)glycine (tricine) or N,N-bis(2-hydroxyethyl)glycine (bicine).

15. The method of claim 1, wherein at least one of $R^5$, $R^6$ and $R^7$ of the compound of (a)(viii) is a hydroxyalkyl, and wherein the alkyl component has a chain length from C1 to C5, is branched or unbranched, and is saturated or unsaturated.

16. The method of claim 1, wherein the compound of (a)(viii) is Tris(hydroxymethyl)-aminomethane (Tris).

17. The method according to claim 1, wherein the biotechnological product is a biopharmaceutical, the contaminating nucleic acid to be isolated is a nucleic acid of the host cell that was used for the production of the biopharmaceutical and/or is a viral nucleic acid, and step (d) is performed to analyse whether such contaminating nucleic acids are contained in the bioprocess sample.

18. The method of claim 1, wherein the method comprises at least one of the following features:
   I. the reagent used in step (a) is added to the sample material does not contain a chaotropic agent, or
   II. if at least one chaotropic agent containing reagent is added in step (c), the addition of the at least one chaotropic agent occurs for the first time in the absence of a branched or unbranched alkanol with 1 to 5 carbon atoms, and
   wherein the sample material with the nucleic acids to be isolated and/or purified is an aqueous composition that is a purification fraction from a purification process for a biotechnologically produced product comprising biomolecules and/or organisms, wherein the biomolecules and/or organisms have at least one of the following features:
      i. the biomolecules and/or organisms are selected from the group consisting of proteins, viruses and/or vaccines,
      ii. the biomolecules and/or organisms are pharmaceutically active substances, and
      iii. the biomolecules are biotechnologically produced molecules that are produced by genetically modified or unmodified organisms.

19. The method of claim 1, wherein step (c) comprises at least the following sub-steps:
   (i) optionally degrading proteins and/or contaminating sample constituents by adding one or more enzymes, optionally in combination with a chaotropic agent containing reagent, in the absence of a branched or unbranched alkanol, to the composition of the sample material and the reagent resulting from step (a) or from steps (a) and (b),
   (ii) adding a formulation comprising at least one chaotropic compound and/or at least one non-ionic detergent,
   (iii) optionally mixing and/or incubating the mixture of sub-step (ii),
   (iv) for adjusting the binding conditions for binding nucleic acid(s) to a carrier material, adding a formulation comprising
      at least one branched or unbranched alkanol with one to five carbon atoms,
      optionally additionally a chaotropic compound, and/or optionally a non-ionic detergent,
   (v) binding the nucleic acid(s) to the carrier material, wherein the carrier material is used in particle form, as non-woven fabric, as fibres, as gel matrix, as membrane, or as column packing material,
   (vi) optionally washing the bound nucleic acid(s) with a washing reagent, and
   (vii) optionally eluting the bound nucleic acid(s) with an elution reagent,
   wherein the one or more enzymes of sub-step (i) and the formulation of sub-step (ii) or the mixture of the one or more enzymes of sub-step (i) and the formulation of sub-step (ii) can be added in variable order to the composition of the sample material and the reagent resulting from step (a) or from steps (a) and (b).

20. The method of claim 19, wherein the one or more enzymes of sub-step (i) are proteinase K.

21. The method of claim 19, wherein the non-ionic detergent is selected from the group consisting of polyoxyethylene-fatty alcohol ethers that comprise a fatty alcohol moiety having 6 to 22 carbon atoms and a polyoxyethylene moiety containing 2 to 150 ($CH_2CH_2O$) units.

22. The method of claim 19, wherein sub-step (ii) is for adjusting or predefining the binding conditions for binding nucleic acids to the carrier material.

23. The method of claim 19, wherein the non-ionic detergents of sub-step (iv) are selected from the group consisting of polyoxyethylene-fatty alcohol ethers that comprise a fatty alcohol moiety having 6 to 22 carbon atoms and a polyoxyethylene moiety containing 2 to 150 ($CH_2CH_2O$) units.

24. The method of claim 19, wherein the carrier material of sub-step (v) contains silica, glass fibre or polyalkylene.

25. The method of claim 24, wherein the polyalkylene is PP, PE/PP, or PE.

26. The method of claim 19, wherein the carrier material is used in the form of beads.

27. The method of claim 26, wherein the carrier material is used in the form of magnetic particles or magnetic beads.

28. The method of claim 19, wherein the washing reagent of sub-step (vi) comprises at least one branched or unbranched alcohol with one to five carbon atoms, optionally additionally a chaotropic compound, and/or optionally a non-ionic surfactant.

29. The method of claim 19, wherein the elution reagent of sub-step (vii) comprises at least one complexing agent in a buffered milieu.

30. The method of claim 1, further comprising:
   (1) carrying out lysis of cells that are contained in the sample before adding the reagent to the sample material according to step (a),
   (2) purifying the sample material to remove cell fragments and/or molecular and/or ionic constituents of the sample material in one or more successive steps before adding the reagent to the sample material according to step (a), and/or
   (3) incubating the composition of the sample material and the reagent resulting from step (a) or the composition of the sample material and the reagent after mixing resulting from process steps (a) and (b).

31. The method of claim 1, wherein the biotechnological product comprises biomolecules produced by genetically modified or unmodified organisms.

32. The method of claim 31, wherein the genetically modified or unmodified organisms are selected from the group consisting of cell lines of mammals, cell lines of birds, cell lines of insects, cell lines of fishes, cell lines of plants, and cloned microorganisms.

33. The method of claim 32, wherein the cell lines of mammals are selected from the group consisting of human cell lines, cell lines from horse cells, cell lines from bovine cells, cell lines from pig cells, cell lines from kangaroo cells, cell lines from sheep cells, cell lines from monkey cells, cell lines from dog cells, cell lines from cat cells, cell lines from marten cells, cell lines from rabbit cells, cell lines from hamster cells, cell lines from rat cells, and cell lines from mouse cells.

34. The method of claim 32, wherein the cell lines of mammals are the cell lines Hek293 (human embryonic kidney), HeLa (human cervical cancer), Vero (kidney of a normal adult African green monkey), MDCK (canine Cocker Spaniel kidney), CHO (Chinese hamster ovary cells), SP2 (mouse myeloma), or NSO (mouse myeloma).

35. The method of claim 32, wherein the genetically modified or unmodified organisms are *Saccharomyces cerevisiae*.

36. The method of claim 1, wherein step (c) comprises one or both of the following steps:
   (c)(1) adding at least one lysis reagent to the bioprocess sample pretreated in step (a), wherein the lysis reagent comprises at least one proteolytic enzyme and/or a chaotropic agent, and
   (c)(2) isolating the target nucleic acid by binding the nucleic acid(s) to a carrier material.

37. The method of claim 36, wherein a binding reagent that comprises an alcohol and/or a chaotropic compound is added in step (c)(2).

38. The method of claim 1, having one or more of the following features:
   a. the biotechnologically produced product is a biopharmaceutical,
   b. the bioprocess sample comprises a biopharmaceutical, wherein the biopharmaceutical is a pharmaceutically active substance comprising one or more biomolecules,
   c. the biotechnologically produced product is a biopharmaceutical, wherein said biopharmaceutical is not a nucleic acid,
   d. the bioprocess sample comprises the purified and/or formulated biotechnologically produced product.

39. The method of claim 38, wherein the biopharmaceutical of c. is a peptide or protein.

40. The method of claim 38, wherein the purified and/or formulated biotechnologically produced product of d. is a biopharmaceutical.

41. The method of claim 1, wherein the purification fraction has one or more of the following characteristics:
   a. the purification fraction is essentially cell-free,
   b. the purification fraction is a chromatographic eluate, and/or
   c. the purification fraction comprises a biopharmaceutical as the biotechnologically produced product, one or more buffer substances and/or salts, and the target nucleic acids to be isolated.

42. The method of claim 1, having at least one of the following characteristics:
   a. the nucleic acid(s) comprises DNA from a host cell and/or host organism used for the production of the biotechnologically produced product, and
   b. the nucleic acid(s) is a nucleic acid of the host cell used for producing the biotechnologically produced product and/or is a viral nucleic acid.

43. The method of claim 42, wherein the host cell of a. is an immortalized host cell.

44. The method of claim 42, wherein the nucleic acid(s) of b. is host cell DNA.

45. The method of claim 1, having one or more of the following characteristics:
   a. the method has an LOD (limit of detection) of at least 1 pg,
   b. the isolation and/or detection of the isolated target nucleic acid is quantitative, and/or
   c. the recovery rate of the isolated target nucleic acid is at least 50%.

46. The method of claim 44, wherein the recovery rate of the isolated target nucleic acid of c. is at least 75% or at least 85%.

47. The method of claim 1, having one or more of the following characteristics:
   a. the nucleic acid(s) is isolated from different purification fractions obtained from a purification process for a biotechnologically produced product,
   b. remaining nucleic acid(s) of the cells used for the production of the biopharmaceutical and/or other nucleic acid contaminants are detected in the purified end product and/or in one or more of the bioprocess samples obtained in the course of the purification process, and/or
   c. the nucleic acid(s) is isolated from various or each purification fraction of the purification process, including the finally purified end product.

48. The method according to claim 1, having one or more the following characteristics:
   a. the method is performed for monitoring the course of the purification process for the biotechnological product,
   b. the method is performed for analysing that the amount of contaminating nucleic acid(s) contained in the purified end product does not exceed a desired and/or permissible amount, and/or
   c. at least a portion of the isolated nucleic acid(s) is detected and it is determined whether the amount of contaminating target nucleic acid in the analysed bioprocess sample is above or below a permissible and/or desired maximum limit.

49. The method of claim 1, wherein the reagent of step (a) also comprises at least one or more of the following components:
   at least one detergent or mixtures of detergents,
   at least one complexing agent or mixtures of complexing agents, and/or
   at least one protein or mixtures of proteins.

50. The method of claim 49, wherein the detergent is selected from the group of non-ionic surfactants consisting of alkylglucosides and/or polyoxyethylene-alkylphenyl ethers.

51. The method of claim 49, wherein the protein is a globular protein.

52. The method of claim 51, wherein the globular protein is albumin or globulin.

53. The method of claim 50, wherein the alkylglucoside is a polysorbate.

54. The method of claim 53, wherein the polysorbate is polysorbate 20 (Tween 20), polysorbate 40, or polysorbate 80.

55. The method of claim 50, wherein the polyoxyethylene-alkylphenyl ether is octoxynol 9 (Triton X-100) or Nonidet P-40.

56. The method of claim 49, wherein the complexing agent(s) is/are selected from the group consisting of ethylenediamine tetraacetic acid (EDTA), ethylene glycol-bis (aminoethylether)-N,N'-tetraacetic acid (EGTA), and ethylenediamine disuccinic acid (EDDS).

57. The method of claim 49, wherein the protein(s) is/are selected from one or more of the following groups:

a. albumin selected from animal, plant and/or human albumin, and
b. globulin selected from animal, plant, and/or human globulin.

58. The method of claim 57, wherein the albumin is bovine serum albumin (BSA).

59. The method of claim 57, wherein the globulin is β-globulin.

60. The method of claim 1, wherein
a. the reagent used for step (a) has at least one of the following features:
   i. the total concentration of the one or more compounds comprising an amino group in the reagent is 5 mM to 500 mM, 25 mM to 350 mM, or 50 mM to 250 mM,
   ii. the reagent comprises one or more detergents, wherein
      (a) the total concentration of the detergent(s) in the reagent is 0.1% (v/v) to 5% (v/v), 0.2% (v/v) to 4% (v/v), 0.5% (v/v) to 3% (v/v), or 1% (v/v) to 3% (v/v),
      (b) the detergent is Triton X-100 at a total concentration in the reagent of 0.2% (v/v) to 0.5% (v/v),
      (c) the detergent is Tween 20 at a total concentration in the reagent of 1% (v/v) to 5% (v/v), or
      (d) the detergent is a non-ionic surfactant.
   iii. the reagent comprises complexing agent(s), and the total concentration of the complexing agent(s) in the reagent is 10 mM to 500 mM, or 10 mM to 100 mM,
   iv. the reagent comprises protein(s), wherein
      (a) the total concentration of the protein(s) in the reagent is 1 mg/mL to 100 mg/mL, 2 mg/mL to 25 mg/mL, 2 mg/mL to 10 mg/mL, or 4 mg/mL to 10 mg/mL, or
      (b) the protein(s) are IgG and/or BSA, and the total concentration of the protein(s) is 2 mg/mL to 25 mg/mL,
   v. the pH value of the reagent is in the range from pH 3 to pH 9,
b. the components of the reagent in the reaction mixture of the sample material and the reagent have at least one of the following features:
   i. the total concentration of the one or more compounds comprising an amino group in the reaction mixture is 2.5 mM to 400 mM, 12.5 mM to 280 mM, or 25 mM to 200 mM,
   ii. the reagent comprises one or more detergents, wherein
      (a) the total concentration of the detergent(s) in the reaction mixture is 0.05% (v/v) to 4% (v/v), 0.1% (v/v) to 3% (v/v), 0.25% (v/v) to 2.5% (v/v), or 5% (v/v) to 2.5% (v/v),
      (b) the detergent is Triton X-100 at a total concentration in the reaction mixture of 0.1% (v/v) to 0.4% (v/v),
      (c) the detergent is Tween 20 at a total concentration in the reaction mixture of 0.5% (v/v) to 4% (v/v), or
      (d) the detergent is a non-ionic surfactant,
   iii. the reagent comprises complexing agent(s), and the total concentration of the complexing agent(s) in the reaction mixture is 5 mM to 400 mM, or 5 mM to 80 mM,
   iv. the reagent comprises protein(s), wherein
      (a) the total concentration of the protein(s) in the reaction mixture is 0.5 mg/mL to 80 mg/mL, 1 mg/mL to 20 mg/mL, 1 mg/mL to 8 mg/mL, or 2 mg/mL to 8 mg/mL, or
      (b) the protein(s) are IgG and/or BSA, and the total concentration of the protein(s) in the reaction mixture is 1 mg/mL to 20 mg/mL
c. the reagent is mixed with the sample material in a ratio of $V_{reagent}$ to $V_{sample\ material}$ in the range of 1:4 to 4:1, 1:2 to 2:1, or 1:1, and/or
d. the reagent does not contain an aqueous formulation that contains phosphate and/or citrate in an overall concentration of ≥5 mM.

61. The method of claim 1, wherein the reagent comprises at least one or more compounds comprising an amino group selected from one or more of the following groups i. to viii:
   i. asparagine, cysteine, glutamine, glycine, threonine, and serine,
   ii. alanine, leucine, isoleucine, methionine, proline, and valine,
   iii. arginine, lysine, and ornithine,
   iv. β-alanine, D-alanine, L-homoserine, and D-valine,
   v. poly-L-lysine, poly-L-lysine hydrobromide, poly-L-lysine hydrochloride, poly(L-glutamine, L-alanine), poly(L-glutamine, L-lysine) hydrobromide, and poly-L-ornithine,
   vi. glycine dimers, glycine trimers, glycine tetramers, and the dipeptide (Ala-Glu),
   vii. N-(tri(hydroxymethyl)methyl)glycine (tricine) and N,N-bis(2-hydroxyethyl)glycine (bicine), and/or
   viii. Tris(hydroxymethyl)-aminomethane (Tris).

62. The method of claim 1, wherein the compound comprising an amino group is N-(tri(hydroxymethyl)methyl)glycine (tricine), N,N-bis(2-hydroxyethyl)glycine (bicine), or Tris(hydroxymethyl)-aminomethane (Tris).

63. The method of claim 1, wherein the reagent used in step (a) comprises at least glycine, Gly-Gly, tricine and/or bicine as the one or more compounds comprising an amino group, at least one complexing agent, and at least one or at least two detergents, and optionally at least one protein.

64. The method of claim 63, wherein the reagent used in step (a) comprises a polyoxyethylene-alkylphenyl ether and/or a polysorbate as detergent.

65. The method of claim 63, wherein the reagent used in step (a) comprises at least one protein.

66. The method of claim 65, wherein the protein is a globular protein.

67. The method of claim 65, wherein the protein is IgG or BSA.

68. The method of claim 1, wherein the reagent used in step (a) does not have any lysing properties.

69. The method of claim 1, wherein the method has an LOD of at least 0.1 pg.

70. The method of claim 1, wherein the bioprocess sample is essentially cell-free.

* * * * *

UNITED STATES PATENT AND TRADEMARK OFFICE
CERTIFICATE OF CORRECTION

PATENT NO. : 10,407,713 B2
APPLICATION NO. : 14/130436
DATED : September 10, 2019
INVENTOR(S) : Peter Porschewski It is certified that error appears in the above-identified patent and that said Letters Patent is hereby corrected as shown below:

In the Claims

Column 75, Claim 59, Line 8:
"β-globulin"
Should be:
-- γ-globulin --.

Signed and Sealed this
Thirty-first Day of March, 2020

Andrei Iancu
*Director of the United States Patent and Trademark Office*